(12) United States Patent
Lundborg et al.

(10) Patent No.: US 11,682,473 B2
(45) Date of Patent: Jun. 20, 2023

(54) SKIN PERMEABILITY PREDICTION

(71) Applicant: ERCO PHARMA AB, Stockholm (SE)

(72) Inventors: Magnus Lundborg, Uppsala (SE); Christian Wennberg, Kista (SE); Ali Narangifard, Arsta (SE); Lars Norlén, Stockholm (SE)

(73) Assignee: ERCO PHARMA AB, Stockholm (SE)

( * ) Notice: Subject to any disclaimer, the term of this patent is extended or adjusted under 35 U.S.C. 154(b) by 1072 days.

(21) Appl. No.: 16/347,913

(22) PCT Filed: Oct. 13, 2017

(86) PCT No.: PCT/EP2017/076237
§ 371 (c)(1),
(2) Date: May 7, 2019

(87) PCT Pub. No.: WO2018/086821
PCT Pub. Date: May 17, 2018

(65) Prior Publication Data
US 2019/0279743 A1    Sep. 12, 2019

(30) Foreign Application Priority Data
Nov. 14, 2016 (EP) .................................. 16198643

(51) Int. Cl.
*G16C 20/30* (2019.01)
*G16C 20/60* (2019.01)
*G16C 10/00* (2019.01)

(52) U.S. Cl.
CPC .......... *G16C 20/30* (2019.02); *G16C 20/60* (2019.02); *G16C 10/00* (2019.02)

(58) Field of Classification Search
CPC ...... G16C 20/30; G16C 20/10; G01N 15/088; G16H 50/50
(Continued)

(56) References Cited

U.S. PATENT DOCUMENTS

2017/0321349 A1* 11/2017 Gupta et al. ............ C40B 30/02
702/19

OTHER PUBLICATIONS

The International Search Report (ISR) for PCT/EP2017/076237 dated Feb. 20, 2018, pp. 1-4.
(Continued)

*Primary Examiner* — Thinh T Nguyen
(74) *Attorney, Agent, or Firm* — McDonnell Boehnen Hulbert & Berghoff LLP

(57) ABSTRACT

The present disclosure relates to a method for predicting the permeability of a stratum corneum lipid matrix to a compound. The method includes providing a model of the stratum corneum lipid matrix including ceramides, free fatty acids, cholesterol and water. The model includes 25-45% total ceramides, based on the molar concentration of all components except water, whereof more than 90% are in extended configuration, and wherein 0-30% of the total ceramides are O-acyl ceramides and 100-70% of the total ceramides are non-O-acyl ceramides. The model also includes 25-45% fatty acid and 25-40% of cholesterol, wherein 1-40% of the cholesterol is located by the fatty acid moeity of the ceramides, and 0.2-6 water molecules per ceramide molecule. The method includes providing molecular designators of the compound and calculating, via means of computer simulations, the predicted permeability using the model and the molecular designators.

17 Claims, 9 Drawing Sheets

CEMOVIS

33/33/33/75/0/1

(58) Field of Classification Search
USPC .......................................................... 703/11
See application file for complete search history.

(56) References Cited

OTHER PUBLICATIONS

Written Opinion of the International Search Authority for PCT/EP2017/076237 dated Feb. 20, 2018, pp. 1-7.
Hoopes, Mathew I. et al. "Bilayer Structure and Lipid Dynamics in a Model Stratum Conreum with Oleic Acid" Journal of Physical Chemistry Part B (2011) vol. 115(12), pp. 3164-3171.
Akinshina, Anna et al. "Effects of monoglycerides and fatty acids on a ceramide bilayer" Physical Chemistry Chemical Physics (2016) vol. 18(26), pp. 17446-17460.
Das, Chinmay et al. "Simulation studies of stratum corneum lipid mixtures" Arxiv Org. (1999), pp. 1-14.
MacDermaid, Christopher M. et al. "Dehydration of multilamellar fatty acid membranes: Towards a computational model of the stratum corneum" Journal of Chemical Physics (2014) vol. 141(22), p. 22D526.
Wennberg, Christian Leo "Computational modeling of biological barriers" Mar. 8, 2016, retrived from the internet: URL:http://www.diva-portal.org/smash/get/diva2:910005.
Norlen, L. et al.: "Human stratum corneum lipid organization as observed by atomic force microscopy on Langmuir-Blodgett films" Journal of Structural Biology (2007) vol. 158(3), pp. 386-400.
Abraham, Michael H. et al. "Human Skin Permeation and Partition: General Linear Free-Energy Relationship Analyses" J. of Pharmaceutical Sciences (2004) vol. 93(6), pp. 1508-1523.
Abraham, Mark James et al. "GROMACS: High performance molecular simulations through multi-level parallelism from laptops to supercomputers" SofwareX 1-2 (2015), pp. 19-25.
Alder, B.J. et al. "Studies in Molecular Dynamics. L General Method" J. Chem. Phys.(1959) vol. 31(2), pp. 159-166.
Barratt, M.D. "Quantitative Structure-Activity Relationship for Skin Permeability" Toxic in Vitro (1995) vol. 9(1), pp. 27-37.
Bennett, Charles H."Efficient Estimation of Free Energy Differences from Monte Carlo Data" Journal of Computational Physics 22 (1976), pp. 245-268.
Berendsen, H.J.C et al. "Molecular dynamics with coupling to an external bath"; Journal of Chemical Physics (1984) vol. 81, 3684-3690.
Blank, Irvin H. et al. "Penetration of Benzene Through Human Skin" Journal of Investigative Dermatology (1985) vol. 35(6), pp. 522-526.
Bouwstra, J. et al. "New Apects of the Skin Barrier Organization" Skin Pharmacol Appl Skin Physiol (2001) vol. 14 (suppl 1), pp. 52-62.
Bussi, Giovanni et al. "Canonical sampling through velocity rescaling" Journal of Chemical Physics 126 (2007) 014101.
Chen, L.Y. "Nonequilibrium fluctation-dissipation theorem of Brownian dynamics" Journal of Chemical Physics 129 (2008) 144113.
Crooks, Gavin E. "Entropy production fluctuation theorem and the nonequilibrium work relation for free energy differences" Physical Review E (1999) vol. 60(3) pp. 2721-2726.
Crooks, Gavin E. "Path-ensemble averages in systems driven far from equilibrium" Physical Review E (2000) vol. 61(3), pp. 2361-2366.
Dahlén B. et al. "Molecular arrangements in sphingolipids. Thermotropic phase behaviour of etracosanoylphytosphingosine" Chemistry and Physics of Lipids (1979) vol. 24, pp. 119-133.
Das, CXhinmay et al. "Water permeation through stratum corneum lipds bilayers from atomistic simulations" Soft Matter (2009) vol. 5, pp. 4549-4555.
Daugherty (1997) Table 10.27 "Skin Permeability of Commercial Solvents".
Degim, I. Tuncer et al. "Skin permeability data anomalous results" International Journal of Pharmaceuticals (1998) vol. 170, pp. 129-133.

Essmann, Ulrich et al. "A smooth particle mesh Ewald method" Journal of Chemical Physics (1995) vol. 103, pp. 8577-8593.
Forney, Michael W. et al. "Calculating fee-energy profiles in biomolecular systems from fast nonequilibrium processes" Physical Review E 78 (2008), pp. 051913-1-051913-9.
Gupta, Rakesh et al. "Molecular Dynamics Simulation Study of Permeation of Molecules Thorough Skin Lipid Bilayers" Journal of Physical Chemistry B. (2016), pp. 1-27.
Hess, Berk et al. "Lincs: A Linear Constraint Solver for Molecular Simulations" Journal of Computational Chemistry (1997) vol. 18(12), pp. 1463-1472.
Hill, J.R. et al. "Molecular models of the intercellular lamellae from epidermal stratum corneum" Biochimica et Biophysica Acta 1616 (2003), pp. 121-126.
Idson, Bernard "Vehicle Effects in Percutaneous Absorption" Drug Metabolism Reviews (1983) vol. 14(2), pp. 207-222.
Iwai, Ichiro et al. "The human skin barrier is organized as stacked bilayers of fully extended ceramides with cholesterol molecules associated with the ceramide sphingoid moiety" Journal of Investgative Dermatology (2012) vol. 132, pp. 2215-2225.
Jorgensen, William L. et al. "Comparison of simple potential functions for simulating liquid water" Journal of Chemical Physics (1983) vol. 79, pp. 926-935.
Klauda, Jeffery B. et al. "Update of the CHARMM all-atom additive force field for lipids: validation on six lipid types" Journal of Physical Chemistry B. (2010) vol. 114, pp. 7830-7843.
Kosztin, Ioan et al. "Calculating potentials of mean force and diffusion coefficients from nonequilibrium processes without Jarzynski's equality" Journal of Chemical Physics (2006) vol. 124, pp. 064106-1-064106-11.
Kumar, Shankar et al. "The weighted histogram analysis method for free-energy calculations on biomolecules. I. The Method" Journal of Computational Chemistry (1992) vol. 13(8), pp. 1011-1021.
Lindahl, V. et al. "Accelerated weight histogram method for exploring free energy landscapes" Journal of Chemical Physics (2014) vol. 141, pp. 044110-1-044110-12.
Lundborg, Magnus et al. "Automatic GROMACS Topology Generation and Comparison of Force Fields for Solvation Free Energy Calculations" Journal of Physical Chemistry B (2014), pp. A-N.
McIntosh, Thomas "Organization of skin stratum corneum extracellular lamellae: Diffraction evidence for asymmetric distribution of cholesterol" Biophysical Journal (2003) vol. 85, pp. 1675-1681.
Mitragotri, Samir et al. "A Mechanistic Study of Ultrasonically-Enhanced Transdermal Drug Delivery" Journal of Pharmaceutical Sciences (1995) vol. 84(6), pp. 697-706.
Miyamoto, Shuichi et al. "SETTLE: An analytical version of the SHAKE and RATTLE algorithm for rigid water models" Journal of Computational Chemistry (1992) vol. 13(8), pp. 952-962.
Mojumdar, E.H. et al. "Statum corneum lipid matrix: location of acyl ceramide and cholesterol in the unit cell of the ong periodicity phase" BBA—Biomembranes (2016), pp. 1-22.
O'Boyle, Noel M. et al. "Open Babel: An open chemical toolbox" Journal of Cheminformatics (2011) vol. 3(33), pp. 1-14.
Park, Sanghyun et al. "Calculating potentials of mean force from steered molecular dynamics simulations" Journal . of Chemical Physics (2004) vol. 120(13), pp. 5946-5961.
Parrinello, M. et al. "Polymorphic transitions in single crystals: A new molecular dynamics method" Journal of Applied Physics (1981) vol. 52, pp. 7182-7190.
Pronk, Sander et al. "GROMACS 4.5: a high-throughput an highly parallel open source molecular simulation toolkit" Bioinformatics (2013) vol. 29(7), pp. 845-854.
Pronk, Sander et al. "Molecular simulation workflows as parallel algorithms: The execution of copemicus, a distributed high-performance computing platform" Journal of Chemical Teory and Computation (2015) vol. 11, pp. 2600-2608.
Roy, Samir D. et al. "Transdermal delivery of narcotic analgesics: Comparative permeabilities of narcotic analgesics through human cadaver skin" Pharmaceutical Research (1989) vol. 6(10), pp. 825-832.
Rullgård, H. et al. "Simulation of transmission electron microscope images of biological specimens" Journal of Microscopy (2011) vol. 243, pt. 3, pp. 234-256.

(56) References Cited

OTHER PUBLICATIONS

Scheuplein, Robert J. et al. "Mechanism of percutaneous absorption. IV. Penetration of nonelectrolytes (alcohols) from aqueous solutions and from pure liquids" Journal of Investigative Dermatology (1973) vol. 60(5), pp. 286-296.

Scheuplein, Robert J. "Mechanism of percutaneous adsorption I. Routes of penetration and the influence of solubility" Journal of Investigative Dermatology (1965) vol. 45(5), pp. 334-346.

Scheuplein, R. J. et al. "Percutaneous absorption of steroids" Journal of Investigative Dermatology (1969) vol. 52(1), pp. 63-70.

Schröter, Annett et al. "Basic nanostructure of stratum corneum lipid matrices based on ceramides [EOS] and [AP]: A neutron diffraction study" Biophysical Journal (2009) vol. 97, pp. 1104-1114.

Shirts, Michael R. et al. "Statistically optimal analysis of samples from multiple equilibrium states" Journal of Chemical Physics 129 (2008), pp. 124105-1-124105-10.

Swartzendruber, Donald C. et al. "Molecular models of the intercellular lipid lamellae in mammalian stratum corneum" Journal of Investigative Dermatology (1989) vol. 92(2), pp. 251-257.

Van Der Merwe, Ema et al. "Physical changes in hydrated skin" International Journal of Cosmetic Science 9 (1987), pp. 237-247.

Vanommeslaeghe, K. et al. "CHARMM General Force Field: A Force Field for Drug-Like Molecules Compatible with the CHARMM All-Atom Additive Biological Force Field" Journal of Computational Chemistry (2010) vol. 31(4), pp. 671-690.

Venable, Richard et al. "CHARMM All-Atom Additive Force Field for Sphingomyelin: Elucidation of Hydrogen Bonding and of Positive Curvature" Biophysical Journal (2014) vol. 107, pp. 134-145.

Yesselman, Joseph D. et al. "MATCH: An Atom-Typing Toolset for Molecular Mechanics Force Field" Journal of Computational Chemistry (2011), pp. 189-202.

* cited by examiner

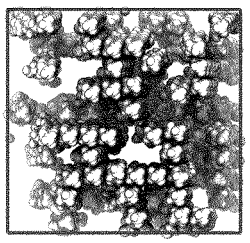 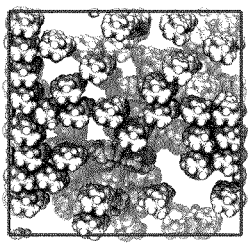 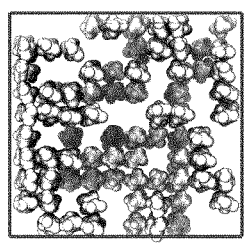 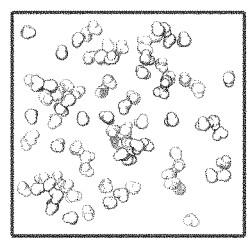
Fig.8a  Fig.8b  Fig.8c  Fig.8d
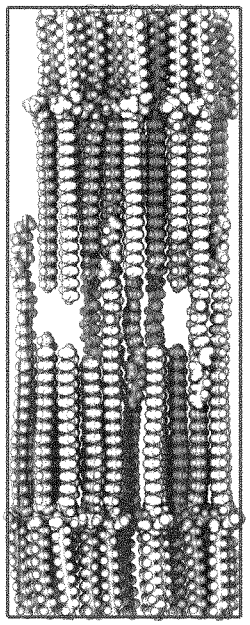 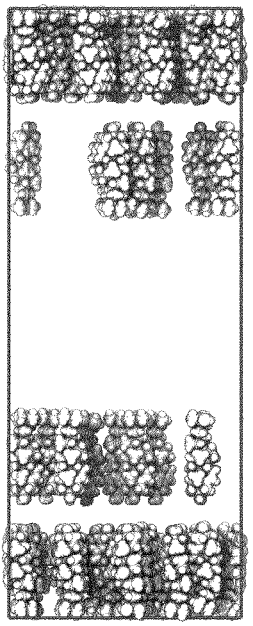 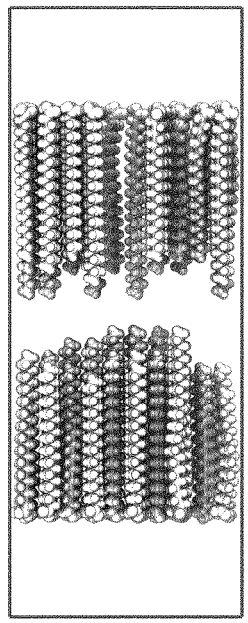 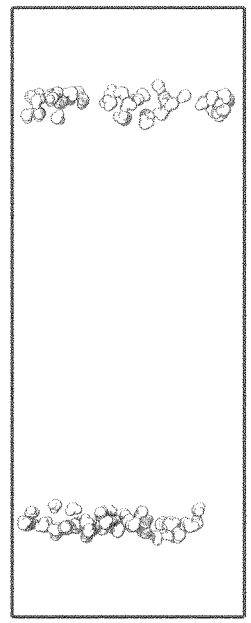
Fig.9a  Fig.9b  Fig.9c  Fig.9d
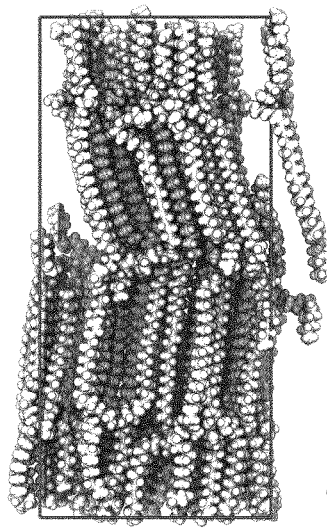 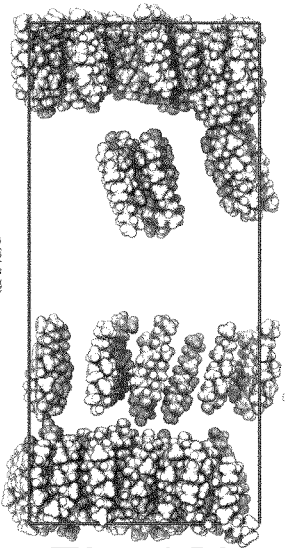 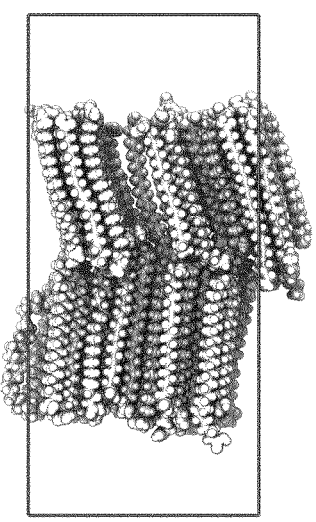 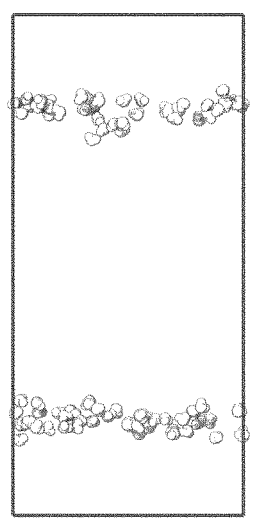
Fig.10a  Fig.10b  Fig.10c  Fig.10d

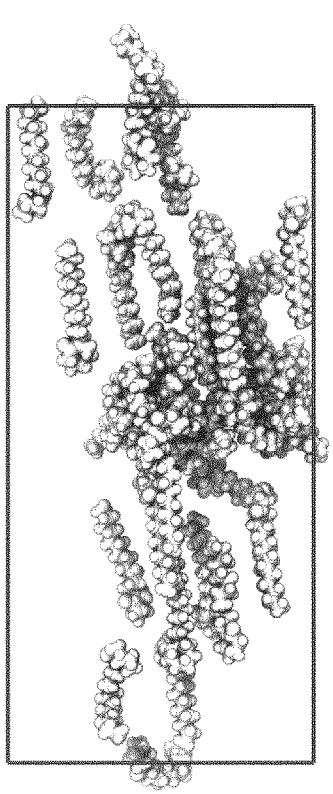
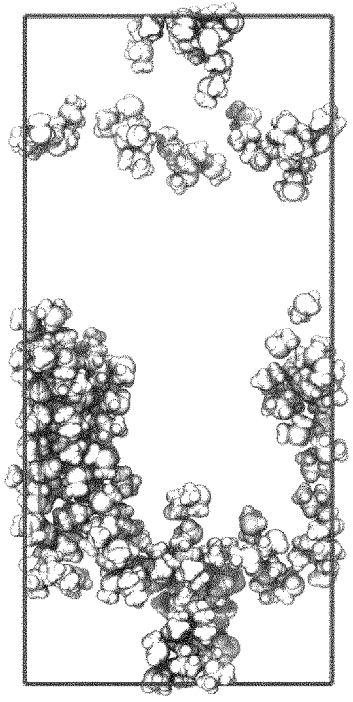
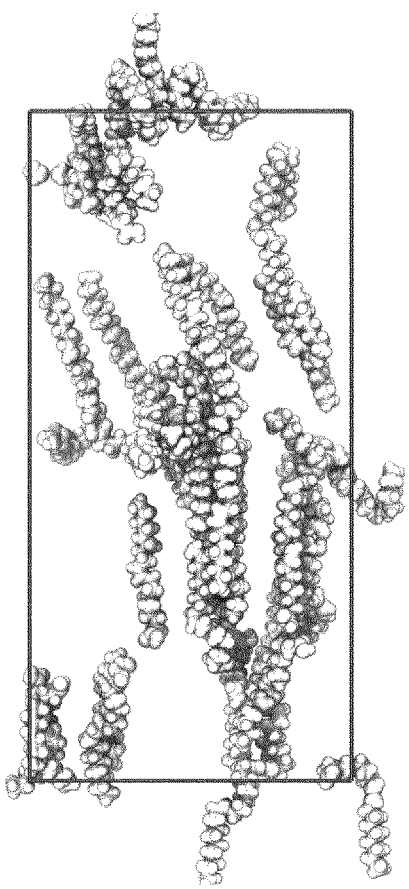
Fig. 11a    Fig. 11b    Fig. 11c
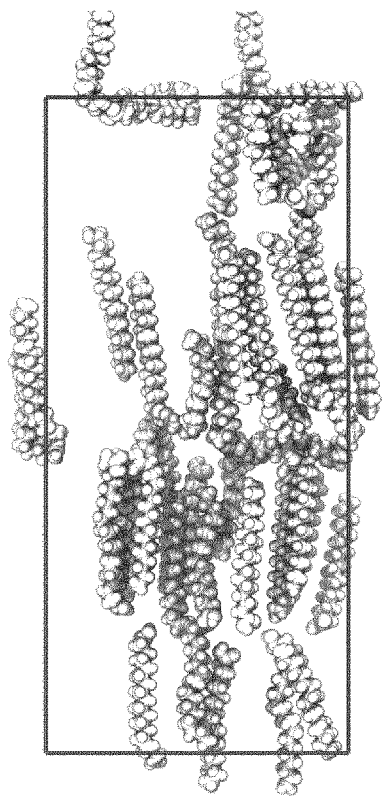
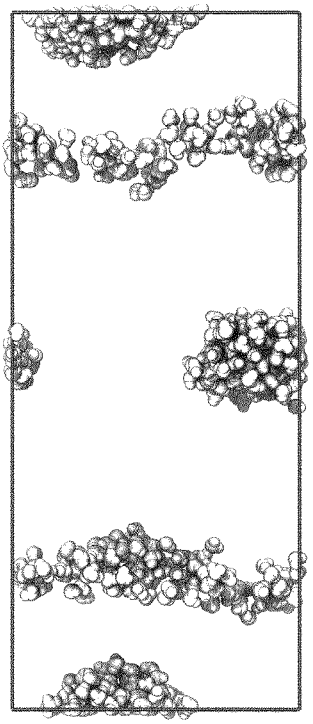
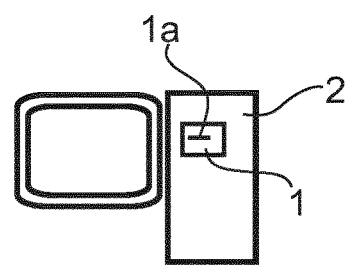
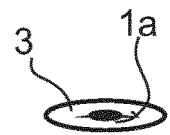
Fig. 11d    Fig. 11e    Fig. 12a
Fig. 12b

SKIN PERMEABILITY PREDICTION

CROSS-REFERENCE TO RELATED APPLICATION

This application is a U.S. national phase of International Application No. PCT/EP2017/076237, filed Oct. 13, 2017, which claims priority to European Patent Application No. 16198643.5, filed Nov. 14, 2016 both of which are incorporated by reference herein in their entirety.

FIELD OF THE INVENTION

The present disclosure relates to a method for predicting the permeability of the stratum corneum of the skin to a compound. In particular, the present disclosure relates to a method of calculating the predicted permeability to the compound via means of computer simulation using a model of a stratum corneum lipid matrix. The present disclosure also relates to methods and uses of said model for predicting the effect of permeability modifying agents on said permeability and for predicting the effect of permeability modifying agents on the organization of the stratum corneum lipid matrix.

BACKGROUND

The stratum corneum is the outer most layer of the epidermis and serves to prevent e.g. water loss and penetration of exogenous compounds through the skin. Morphologically, the stratum corneum is formed by multiple stacks of flattened cells (corneocytes), each surrounded by intercellular lipids. These lipids may be referred to as the stratum corneum lipid matrix, which includes long-chain ceramides, free fatty acid and cholesterol as its main components.

Owing to its barrier functionality, the stratum corneum may represent both a challenge and an opportunity. Exposure to chemicals may be extensive in modern society, and the risk of harm upon uptake via the skin may be significant. At the same time, administration of drugs through the skin, instead of e.g. per orally, may increase treatment control and reduce risk of adverse drug effects. Also, administration of cosmetic compounds to the skin or through the skin may be desirable.

Often, the permeability of the stratum corneum to most drug molecules/compounds is low and the stratum corneum may therefore pose an obstacle to e.g. topical administration of drugs. As a result, permeability modifying agents (PMAs) with permeability enhancing properties may be added to, or used in combination with, topical and transdermal formulations. Likewise, PMAs with permeability decreasing properties may be useful to e.g. protect toxic chemicals from entering the body through the skin.

Although many PMAs exist which are believed to affect the stratum corneum lipid matrix, the mechanisms of action for many of them are not known or only partly elucidated. As a result, the variety of PMAs which may be readily used to overcome the barrier functionality of the stratum corneum and the stratum corneum lipid matrix is limited.

Assessment of chemical safety and/or drug administration through skin has often been carried out based on animal testing, and/or by relying on quantitative structure-activity relationship (QSAR) models. Such models, relying on statistical tools to for example relate predictor variables (such as for example molecular descriptors of chemicals) to response variables (such as for example a biological activity of the chemicals), may be sensitive to multiple factors such as the quality of input data, the choice of descriptors and the statistical methods used for modeling and validation. Models created based on a training set of compounds may give sufficiently accurate results for some molecules, but may fail to give sufficiently accurate predictions for other molecules not part of such a training set.

As an alternative, models of the stratum corneum lipid matrix have been used to calculate e.g. its permeability to several compounds using molecular dynamics (MD) simulations. However, the discrepancies between the results of such models and experimental data have been shown to be high. For example, the calculated permeability of the stratum corneum lipid matrix to water was shown to differ by 1.5 log units (mean square error of 2.25 log units) when compared to experimental data (Das et al., 2009), while the calculated permeability of the stratum corneum lipid matrix to 11 different compounds (oxygen, ethanol, acetic acid, urea, butanol, benzene, dimethyl sulfoxide, toluene, phenol, styrene and ethylbenzene) was shown to differ by >2 log units on average (Gupta et al., 2016).

In light of the above, methods for more accurate assessment of the permeability of the stratum corneum to various compounds, and/or methods for studying the effects of PMAs on the stratum corneum, are required.

SUMMARY OF THE INVENTION

In general, it is an object of the present disclosure to provide new methods for overcoming or at least partly alleviating the above mentioned drawbacks of presently available methods.

It is an object of the present disclosure to provide a new method for predicting or calculating the permeability of the stratum corneum lipid matrix to a compound, which could be used to for example improve the assessment of chemical safety and/or drug administration through skin without relying on animal testing or statistical methods such as QSAR. Said method can for example be used in toxicity assessments of different compounds.

It is an object of the present disclosure to provide a new method for predicting or calculating the effect of a structural difference between a first compound and a second compound on the permeability of the stratum corneum lipid matrix to these compounds, which could be used for example to perform screening of several compounds for suitable permeant properties.

It is an object of the present disclosure to provide a new method for predicting the permeability of a stratum corneum lipid matrix, with at least one chemical permeability modifying agent (PMA), to a compound. Such a method may for example be used to screen several PMAs for suitable permeability modifying (such as enhancing or decreasing) properties, and/or to better understand their mechanisms of action.

It is an object of the present disclosure to provide a new method for identifying a PMA for a compound which has a desired effect on the permeability of a stratum corneum lipid matrix to said compound.

These and other objects which are evident to the skilled person from the present disclosure are met by different aspects of the invention as claimed in the appended claims and as generally disclosed herein.

Thus, in the first aspect of the present disclosure, a method is provided for predicting or calculating the permeability of a stratum corneum lipid matrix to a compound, comprising the steps of:

a) providing a model of the stratum corneum lipid matrix representing at least one repeating unit and comprising ceramides, free fatty acids, cholesterol and water, which model comprises the following:
   i) 25-45% total ceramides based on the molar concentration of all components except water, of which more than 90% are in extended configuration and wherein 0-30% of said total ceramides are O-acyl ceramides and 100-70% of said total ceramides are non-O-acyl ceramides;
   ii) 25-45% free fatty acid, based on the molar concentration of all components except water,
   iii) 25-40% cholesterol, based on the molar concentration of all components except water, wherein 1-40% of said cholesterol is located by the fatty acid moiety of said ceramides; and
   iv) 0.2-6 water molecules per ceramide molecule;
b) providing the molecular designators of a compound to which the permeability of the stratum corneum lipid matrix is to be predicted, and
c) calculating, via means of computer simulation, the predicted permeability of the stratum corneum lipid matrix to said compound using said model and the molecular designators of the compound.

It will be appreciated that steps a) and b) above, may be performed in any desired order.

In one embodiment, there is provided a method, wherein in step a i) 1-30% of said total ceramides are O-acyl ceramides and 99-70% of said total ceramides are non-O-acyl ceramides.

In one embodiment, the compound is a polar or a nonpolar compound, such as a nonpolar compound.

To clarify, the number of water molecules per ceramide molecule recited above can equally well be presented as the number of water molecules per lipid molecule. For example, in a system with a molar relationship of 1:1:1 of ceramide: free fatty acid:cholesterol one water molecule per ceramide molecule corresponds to one water molecule per three lipid molecules, which can be expressed as 0.3 or 0.33 water molecules per lipid molecule. For example, as illustrated in the Example section below, the lipid matrix system represented by 33/33/33/75/5/1 specifying water molecule content per ceramide molecule corresponds to the system 33/33/33/75/5/0.3 specifying water molecule content per lipid molecule. The skilled person will appreciate this conversion and knows how to apply it to other amounts of water not exemplified here.

In one embodiment, there is provided a method, wherein in step a ii) no more than, such as less than, 10% of the free fatty acids are negatively charged.

To clarify, the wording "wherein no more than 10% of the free fatty acids are negatively charged" refers to 10% or less of the free fatty acid content of the model as disclosed herein and corresponds to 2.5-4.5% total free fatty acid in the model, based on the molar concentration of all components except water.

In one embodiment, there is provided a method, wherein in step a iii) wherein no more than, such as less than, 10% of the cholesterol molecules are replaced by cholesterol sulfate molecules.

To clarify, the wording "wherein no more than 10% of the cholesterol molecules are replaced by cholesterol sulfate molecules" refers to 10% or less of the cholesterol content of the model as disclosed herein and corresponds to 2.5-4.0% total cholesterol in the model, based on the molar concentration of all components except water.

As briefly mentioned above, the present method may be useful for the assessment of chemical safety and/or drug administration through skin without relying on animal testing or statistical methods such as QSAR. The present method takes advantage of an improved model of the stratum corneum lipid matrix providing the necessary accuracy, which allows for improved prediction and assessment outcomes. It will be appreciated that the method as disclosed herein may be used for the prediction of the permeability of the stratum corneum lipid matrix to any compound provided the molecular designator of said compound can be provided. Thus, the present method is not limited to any group of compounds, size of molecules or the like.

Herein, means of computer simulation may for example include a computer or a network of computers, each including a central processing unit (CPU) and for example a storage memory (HDD) and an operating memory (RAM). Examples of such means of computer simulation may for example include a standalone computer on which program code containing instructions to perform a required simulation may run. Other examples may for example include a cluster of multiple such computers. On such a cluster, individual computing nodes may for example be instructed to each perform a limited part of the simulation, and the results of the individual nodes may at a later stage be retrieved and combined to obtain the result of the full simulation, if the simulation so allows. It is envisaged that means for computer simulation as used herein may also, or instead, include e.g. one or many graphics processing units (GPU) on which (at least part of) the simulation for each computer or computing node may run in addition to, or instead of, on a CPU.

Ceramides consist of a sphingoid moiety linked to a fatty acid via an amide bond.

As used herein, the term "extended configuration" in relation to ceramides refers to a configuration/conformation wherein the carbon backbone chains of the fatty acid moiety and the sphingoid moiety of said ceramides are arranged in substantially opposite directions, such as forming at least an angle of more than 90° between said chains, such as forming at least an angle of more than 120° between chains. In the context of the present disclosure, the term "extended configuration" in relation to ceramides refers to "splayed configuration" of ceramides and the terms are used interchangeably herein. The skilled person will appreciate that splayed configuration is opposed to hair pin configuration.

It will be appreciated that the present model may comprise an optional number of repeating units.

As used herein, the term "total lipids" refers to the total lipid content of said model independent of the identity of said lipids.

As used herein, the term "total ceramides" refers to the total ceramide content of said model independent of the identity of said ceramides.

As used herein, the term "O-acyl ceramides" encompasses all kinds of O-acyl ceramides, including ceramides EOS, EOP and EOH.

As used herein, the term "non-O-acyl ceramides" refers to any ceramides which are not O-acyl ceramides. Non-limiting examples of non-O-acyl ceramides include ceramide AS, ceramide NS, ceramide AP and ceramide NP.

As used herein, the term "free fatty acid" refers to fatty acids not comprised in ceramides or other compounds.

As used herein, the term "free fatty acids" encompasses uncharged fatty acids and deprotonated i.e. negatively charged fatty acids. The present disclosure encompasses a model wherein no more than, such as less than, 10% of the free fatty acids are negatively charged. In one embodiment of the present method, there is provided a model wherein no more than 10%, such as 0-10%, such as less than 10%, such as 0-9%, such as 0-5%, such as 0-2%, such as 0% of the free fatty acids are negatively charged.

As used herein, the wording "cholesterol (is) located by the fatty acid moiety of ceramides" refers to that the cholesterol is positioned closer to the fatty acid moiety of said ceramides than to the sphingoid moiety of said ceramides when the ceramides are in extended configuration. Conversely, the wording "cholesterol (is) located by the sphingoid moiety of ceramides" refers to that the cholesterol is positioned closer to the sphingoid moeity of said ceramides than to the fatty acid moiety of said ceramides when the ceramides are in extended, i.e. splayed, configuration.

In one embodiment of the present method, there is provided a model wherein 5-35%, such as 10-30%, such as 15-30%, such as 20-30%, such as 25% of said cholesterol is located by the fatty acid moiety of said ceramides.

In one embodiment of the present method, there is provided a model wherein 95-65%, such as 90-70%, such as 85-70%, such as 80-70%, such as 75% of said cholesterol is located by the sphingoid moiety of said ceramides.

For example in one embodiment of the present method, there is provided a model wherein 1-40% of said cholesterol is located by the fatty acid moiety of said ceramides and 99-60% of said cholesterol is located by the sphingoid moiety of the ceramides. In another embodiment, 5-35% of said cholesterol is located by the fatty acid moiety of said ceramides and 95-65% of said cholesterol is located by the sphingoid moiety of the ceramides. The skilled person will appreciate that in some embodiments, wherein X % of the cholesterol is located by the fatty acid moiety of said ceramides and 100–X % of said cholesterol is located by the sphingoid moiety of the ceramides. For example, in one embodiment about 25% of said cholesterol is located by the fatty acid moiety of said ceramides and about 75% of said cholesterol is located by the sphingoid moiety of the ceramides.

As used herein the term "cholesterol" encompasses both cholesterol and cholesterol sulfate. The present disclosure encompasses a model comprising no more than, such as less than, 10% cholesterol sulfate, i.e. no more than, such as less than, 10% of the cholesterol molecules may be replaced by cholesterol sulfate molecules. In one embodiment of the present method, there is provided a model wherein no more than 10%, such as 0-10%, such as less than 10%, such as 0-9%, such as 0-5%, such as 0-2%, such as 0% of the cholesterol molecules are replaced by cholesterol sulfate.

In the presently disclosed model the % given refers to % of compound based on the molar concentration of all components except water, unless explicitly stated otherwise.

As used herein, the term "model" refers to the molecular coordinates of the components of the system organized such that they represent the stratum corneum lipid matrix.

In one embodiment the method for predicting permeability of a stratum corneum lipid matrix to a compound, there is provided a model comprising the following:
i) 25-45% total ceramides, based on the molar concentration of all components except water, of which more than 90% are in extended configuration and
wherein 0-30% of said total ceramides are O-acyl ceramides and 100-70% of said total ceramides are non-O-acyl ceramides, such as 1-30% of said total ceramides are O-acyl ceramides and 99-70% of said total ceramides are non-O-acyl ceramides;
wherein the sphingoid moiety of said non-O-acyl ceramides has a length of 18-20 carbons and the fatty acid moiety of said non-O-acyl ceramides has a chain length distribution according to the following:
0-16%, such as 0-15%, such as 0-14% of non-O-acyl ceramides have a fatty acid chain length of 20 carbons or less;
0-16%, such as 0-15%, such as 0-14% of non-O-acyl ceramides have a fatty acid chain length of 21-22 carbons;
24-53%, such as 25-50%, such as 26-47% of non-O-acyl ceramides have a fatty acid chain length of 23-24 carbons;
19-53%, such as 20-50%, such as 21-47% of non-O-acyl ceramides have a fatty acid chain length of 25-26 carbons;
0-16%, such as 0-15%, such as 0-14% of non-O-acyl ceramides have a fatty acid chain length of 27-28 carbons;
0-21%, such as 0-20%, such as 0-19% of non-O-acyl ceramides have a fatty acid chain length of 29 carbons or more, such as of non-O-acyl ceramides have a fatty acid chain length of 29-30 carbons;
ii) 25-45% free fatty acid, based on the molar concentration of all components except water, wherein said free fatty acids have a chain length distribution according to the following:
0-16%, such as 0-15%, such as 0-14% of the free fatty acids have a fatty acid chain length of 20 carbons or less;
0-16%, such as 0-15%, such as 0-14% of the free fatty acids have a fatty acid chain length of 21-22 carbons;
24-53%, such as 25-50%, such as 26-47% of the free fatty acids have a fatty acid chain length of 23-24 carbons;
19-53%, such as 20-50%, such as 21-47% of the free fatty acids have a fatty acid chain length of 25-26 carbons;
0-16%, such as 0-15%, such as 0-14% of the free fatty acids have a fatty acid chain length of 27-28 carbons; and
0-58%, such as 0-55%, such as 0-52% of the free fatty acids have a fatty acid chain length of 29 carbons or more;
iii) 25-40% cholesterol, based on the molar concentration of all components except water, wherein 1-40% of said cholesterol is located by the fatty acid moiety of said ceramides and 99-60% of said cholesterol is located by the sphingoid moiety of the ceramides; and
iv) 0.2-6 water molecules per ceramide molecule.

In one embodiment, there is provided a method, wherein in step a ii) no more than, such as less than, 10% of the free fatty acids are negatively charged.

In one embodiment, there is provided a method, wherein in step a iii) wherein no more than, such as less than, 10% of the cholesterol molecules are replaced by cholesterol sulfate molecules.

It is to be understood that the percentages related to the chain length distribution above refer to percentages of total non O-acyl ceramides and total free fatty acids, respectively. To illustrate, for example when the model comprises 25 total ceramides, based on the molar concentration of all components except water, and 0% O-acyl ceramides, then the feature that 15% of the non-O-acyl ceramides present in the model have a fatty acid chain length of 21-22 carbons is to be interpreted as 15% out of 25%. In other words 3.75% of the total molecules or components (not counting water) are non-O-acyl ceramides having a fatty acid chain length of 21-22 carbons.

In one embodiment of said method, a model is provided wherein 0-15% of non-O-acyl ceramides have a fatty acid chain length of 20 carbons or less; 0-15 of non-O-acyl ceramides have a fatty acid chain length of 21-22 carbons; 25-50 of non-O-acyl ceramides have a fatty acid chain length of 23-24 carbons; 20-50 of non-O-acyl ceramides have a fatty acid chain length of 25-26 carbons; 0-15 of non-O-acyl ceramides have a fatty acid chain length of 27-28 carbons; 0-20 of non-O-acyl ceramides have a fatty acid chain length of 29 carbons or more. In particular embodiments, a model is provided wherein 0-10%, such as 2-8% such as 4-6%, such as 5-6%, such as 5.1% of non-O-acyl ceramides have a fatty acid chain length of 20 carbons or less; 5-15%, such as 7-13%, such as 9-11%, such as 10-11%, such as 10.3% of non-O-acyl ceramides have a fatty acid chain length of 21-22 carbons; 30-50%, such as 35-45%, such as 40-41%, such as 41% of non-O-acyl ceramides have a fatty acid chain length of 23-24 carbons; 20-40%, such as 25-35%, such as 29-31%, such as 30.8% of non-O-acyl ceramides have a fatty acid chain length of 25-26 carbons; 5-15%, such as 7-13%, such as 9-11%, such as 10-11%, such as 10.3% of non-O-acyl ceramides have a fatty acid chain length of 27-28 carbons; 0-10%, such as 0-5%, such as 1-3%, such as 2-3%, such as 2.5 or 2.6% of non-O-acyl ceramides have a fatty acid chain length of 29 carbons or more.

In one embodiment said model, the free fatty acids are present at 28-45%, such as 28-40%, such as 28-38%, such as at 30-35%, such as at 31-34%, such as 32-34%, such as 33-34%, such as 33 or 34%, based on the molar concentration of all components except water.

In one embodiment of said method, a model is provided wherein said free fatty acids have a chain length distribution according to the following: 0-15% of the free fatty acids have a fatty acid chain length of 20 carbons or less; 0-15% of the free fatty acids have a fatty acid chain length of 21-22 carbons; 25-50% of the free fatty acids have a fatty acid chain length of 23-24 carbons; 20-50% of the free fatty acids have a fatty acid chain length of 25-26 carbons; 0-15% of the free fatty acids have a fatty acid chain length of 27-28 carbons; and 0-55% of the free fatty acids have a fatty acid chain length of 29 carbons or more.

In particular embodiments, a model is provided wherein said free fatty acids have a chain length distribution according to the following: 0-10%, such as 3-7%, such as 4-5%, such as 4.5% of the free fatty acids have a fatty acid chain length of 20 carbons or less; 5-15%, such as 7-13%, such as 9-10%, such as 9.1% of the free fatty acids have a fatty acid chain length of 21-22 carbons; 30-40%, such as 32-36%, such as 34-35%, such as 34.1% of the free fatty acids have a fatty acid chain length of 23-24 carbons; 20-40%, such as 20-30%, such as 25-30%, such as 27-28%, such as 27.3% of the free fatty acids have a fatty acid chain length of 25-26 carbons; 5-15%, such as 7-13%, such as 9-10%, such as 9.1% of the free fatty acids have a fatty acid chain length of 27-28 carbons; and 0-40%, such as 0-30%, such as 10-20%, such as 15-16%, such as 15.9% of the free fatty acids have a fatty acid chain length of 29 carbons or more.

In particular embodiments, a model is provided wherein said free fatty acids have a chain length distribution according to the following 4-6% of the fatty acids have a fatty acid chain length of 20 carbons; 8-10% of the fatty acids have a fatty acid chain length of 22 carbons; 32-36% of the fatty acids have a fatty acid chain length 24 carbons; 25-29% of the fatty acids have a fatty acid chain length of 26 carbons; 8-10% of the fatty acids have a fatty acid chain length of 28 carbons; and 15-17% of the fatty acids have a fatty acid chain length of 30 carbons.

In particular embodiments, a model is provided wherein said free fatty acids have a chain length distribution according to the following 4.5% of the fatty acids have a fatty acid chain length of 20 carbons; 9.1% of the fatty acids have a fatty acid chain length of 22 carbons; 34.1% of the fatty acids have a fatty acid chain length 24 carbons; 27.3% of the fatty acids have a fatty acid chain length of 26 carbons; 9.1% of the fatty acids have a fatty acid chain length of 28 carbons; and 15.9% of the fatty acids have a fatty acid chain length of 30 carbons.

In one embodiment of said model, the cholesterol is present at 28-38%, such as at 30-35%, such as at 31-34%, such as 32-34%, such as 33-34%, such as 33 or 34%, based on the molar concentration of all components except water.

In one embodiment of said method, there is provided a model wherein said repeating unit comprises two layers of extended ceramides arranged with their fatty acid side chains interfacing with each other and with their sphingoid side chains interfacing with each other over the periodic box boundary. In one embodiment, said at least one repeating unit extends approximately 10-12 nm, such as 10.5-11 nm, such as 10.6 nm in the direction perpendicular to the membrane surface. In one embodiment, said at least one repeating unit extends approximately 10-11.2 nm, such as 10.1-11.2 nm, such as 10.3-11 nm, such as 10.4-10.8 nm, such as 10.5-10.7 nm, such as 10.6 nm in the direction perpendicular to the membrane surface.

In one embodiment of said method, said distance between the ceramide head groups via the fatty acid side chain region is approximately 6.3-6.7 nm, such as 6.4-6.6 nm, such as 6.5 nm, and the distance between the ceramide head groups via the sphingoid side chain region is approximately 4.3-4.7 nm, such as 4.4-4.6 nm, such as 4.5 nm in the direction perpendicular to the membrane surface. In one particular embodiment, there is provided a model wherein the distance between the ceramide head groups via the fatty acid side chain region is approximately 6.5 nm and the distance between the ceramide head groups via the sphingoid side chain region is approximately 4.5 nm in the direction perpendicular to the membrane surface.

As used therein, the number of water molecules per ceramide molecule refers to the number of water molecules per ceramide of said total ceramides, in other words independently of the identity of said ceramide.

In one embodiment of the present method, more than 0.2, such as more than 0.25, such as more than 0.5 water molecules are present per ceramide molecule. In one embodiment of the present method, there is provided a model of the stratum corneum lipid matrix wherein 0.2-6 water molecules are present per ceramide molecule, such as 0.25-6 water molecules are present per ceramide molecule, such as 0.5-6 water molecules are present per ceramide molecule, such as 0.5-4 water molecules are present per ceramide molecule. In one embodiment of the present method, there is provided a model of the stratum corneum lipid matrix wherein 0.2-6 water molecules are present per ceramide molecule, such as 1-3 water molecules are present per ceramide molecule, such as 1-2 water molecule per ceramide molecule is present. In particular, in one embodiment, 1 water molecule per ceramide molecule is present in said model.

As used therein, the number of water molecules per lipid molecule refers to the number of water molecules per lipid of said total lipid, in other words independently of the identity of said lipid. In one embodiment of the present method, there is provided a model of the stratum corneum lipid matrix wherein 0.05-1.3 water molecules are present per lipid molecule, such as 0.1-1.3 water molecules are present per lipid molecule, such as 0.2-1.3 water molecules are present per lipid molecule, such as 0.2-1 water molecules are present per lipid molecule, such as 0.3-1 water molecules are present per lipid molecule, such as 0.3-0.7 water molecules are present per lipid molecule, such as 0.3-0.6 water molecules per lipid molecule is present. In particular, in one embodiment, 0.3 water molecules per lipid molecule is present in said model. In one embodiment of the present method, there is provided a model of the stratum corneum lipid matrix wherein 0.05-2, water molecules are present per lipid molecule, such as 0.1-2 water molecules are present per lipid molecule, such as 0.2-2 water molecules are present per lipid molecule. In one embodiment, 0.5-1.3 or 0.3-1.3 water molecules are present per lipid molecule.

In one embodiment, said water molecules are embedded in the lipid matrix. As used herein, the term "embedded in the lipid matrix" means that said water molecules are associated with the head groups of the ceramides, free fatty acids and cholesterol, in contrast to being arranged on the outside of lipid layer or structure.

The skilled person will appreciate that the amount of water molecules in the model of the stratum corneum lipid matrix can be expressed as water molecules per ceramide molecule or as water molecules per lipid molecule.

As discussed above, the majority of ceramides in the present model are arranged in extended configuration. Thus, in one embodiment of present method, there is provided a model of the stratum corneum lipid matrix wherein in said model of the stratum corneum lipid matrix approximately 90-100%, such as approximately 95-100%, such as approximately 98-100%, such as approximately 99-100%, such as approximately 100% of the total ceramides are in extended configuration.

In one embodiment of present method, there is provided a model of the stratum corneum lipid matrix which comprises approximately 1-10% O-acyl ceramides, such as approximately 2-8% O-acyl ceramides, such as approximately 5% O-acyl ceramides, based on the molar concentration of all components except water. In one embodiment, said model comprises approximately 3-8% O-acyl ceramides based on the molar concentration of all components except water. In another embodiment, said model comprises 2-7% O-acyl ceramides based on the molar concentration of all components except water.

In one embodiment of present method, there is provided a model of the stratum corneum lipid matrix wherein approximately 1-30% of the total ceramides, such as approximately 5-20% of the total ceramides, such as approximately 13-17%, such as 13-15% or 15-17% of the total ceramides are O-acyl ceramides in said model of the stratum corneum lipid matrix. In one embodiment 15% of the total ceramides are O-acyl ceramides in said model of the stratum corneum lipid matrix. In one embodiment, said O-acyl ceramides are selected from one or more from the group consisting of ceramide EOS, ceramide EOP and ceramide EOH. In one particular embodiment, said O-acyl ceramides are ceramide EOS and/or EOP.

In one embodiment of said method, there is provided a model wherein the molar concentration of total ceramides in said model of the stratum corneum lipid matrix is approximately 30-35% based on the molar concentration of all components except water, such as 33-34% based on the molar concentration of all components except water, and wherein 10-20% of said ceramides are O-acyl ceramides, such as 10-15%, such as 11-14%, such as 12 or 13% of said ceramides are O-acyl ceramides. In one embodiment, 13-15% or 13-17% of said ceramides are O-acyl ceramides. In one particular embodiment, said molar concentration of total ceramides is 33-34% wherein 13% of total ceramides are O-acyl ceramides, for example ceramide EOS, EOP and/or EOH. In one embodiment, said O-acyl ceramides are EOS, EOP and EOH, in other words a mixture of EOS, EOP and EOH. In one embodiment, said O-acyl ceramides are selected from the group consisting of ceramide EOS and ceramide EOP; ceramide EOS and ceramide EOH; and ceramide EOP and ceramide EOH. In one particular embodiment, said O-acyl ceramides are ceramide EOS and EOP, in other words a mixture of EOS and EOP. In one embodiment said O-acyl ceramides are ceramide EOS. In one embodiment said O-acyl ceramides are ceramide EOP. In another embodiment, said O-acyl ceramides are ceramide EOH.

The skilled person will appreciate that minor changes/modifications in the structure of the ceramides comprised in the model as disclosed in the context of the present method, which changes do not exert any significant effect on the properties of said ceramides are expected not to affect the present method. Non-limiting examples of such changes include the addition of an OH group, the repositioning of an OH group to a neighboring C-atom and the repositioning of an doublebond in the carbon backbone to neighboring C-atoms. The skilled person is aware of what kind of changes are expected not to exert any significant effect on the properties of said ceramides. Thus the present disclosed encompasses methods, wherein the stratum corneum model comprises ceramides with such changes. For example such changes may involve changes similar to or corresponding to the differences between ceramide NP and ceramide AP or the above mentioned ceramide EOP and ceramide EOS.

In one embodiment of said method as disclosed herein, there is provided a model wherein said non O-acyl ceramide is selected from the group consisting of ceramide NP, ceramide NS, ceramide AP and ceramide AS, such as the group consisting of ceramide NP and ceramide NS or the group consisting of ceramide AP and ceramide AS. The skilled person will appreciate that in the model as disclosed herein the ceramides may be combined in any way. Thus, in one embodiment the non O-acyl ceramides in the model comprises ceramide NP, ceramide NS, ceramide AP and ceramide AS. In one embodiment said model comprises ceramide NP, ceramide NS, and ceramide AS. In one embodiment said model comprises ceramide NP, ceramide NS, and ceramide AP. In one embodiment said model comprises ceramide NP, ceramide NS, and ceramide AP. In one embodiment said model comprises ceramide NP, ceramide AP, and ceramide AS. In one embodiment said model comprises ceramide NS, ceramide AP, and ceramide AS. In one embodiment said model comprises ceramide NP and ceramide NS. In one embodiment said model comprises ceramide AP and ceramide AS In one embodiment said model comprises ceramide NP and ceramide AS. In one embodiment said model comprises ceramide AP and ceramide NS.

In one particular embodiment of said method, there is provided a model wherein said non O-acyl ceramides have an approximate chain length distribution of the fatty acid moiety according to the following:

0-15% of non O-acyl ceramides are ceramide NP, NS, AP and/or AS which have a fatty acid chain length of 20 carbons;

0-15% of non O-acyl ceramides are ceramide NP, NS, AP and/or AS which have a fatty acid chain length of 22 carbons;

25-50% of non O-acyl ceramides are ceramide NP, NS, AP and/or AS which have a fatty acid chain length of 24 carbons;

20-50% of non O-acyl ceramides are ceramide NP, NS, AP and/or AS which have a fatty acid chain length of 26 carbons;

0-15% of non O-acyl ceramides are ceramide NP, NS, AP and/or AS which have a fatty acid chain length of 28 carbons;

0-10% of non O-acyl ceramides are ceramide NP, NS, AP and/or AS which have a fatty acid chain length of 30 carbons.

The skilled person will appreciate that any subset of said ceramides is encompassed hereby as explained above. Additionally, the skilled person will appreciate that ceramides with different fatty acid chain length may independently from each other be represented by different subsets of ceramide NP, NS, AP and AS. For example, in the model disclosed herein, 0-15% of non O-acyl ceramides may be ceramide NP, NS, AP which have a fatty acid chain length of 20 carbons, while 25-50% of non O-acyl ceramides may be ceramide NP and AS which have a fatty acid chain length of 24 carbons.

To clarify, wherein the above mentioned non O-acyl ceramides are ceramide NP, NS, AP and AS or any subgroup thereof, the percentage given refers to the total percentage of NP, NS, AP and AS ceramides with the given fatty acid chain length.

In one particular embodiment, said non O-acyl ceramides are ceramides NP and ceramides NS. In another particular embodiment, said non O-acyl ceramides are ceramides AP and ceramides AS.

In one embodiment of said method, there is provided a model wherein the molar concentration of free fatty acids in said model of the stratum corneum lipid matrix is approximately 30-35% based on the molar concentration of all components except water, such as 32-35% based on the molar concentration of all components except water, such as 33-34% based on the molar concentration of all components except water.

In one embodiment of said method, there is provided a model wherein 0-2%, such as 0% of the free fatty acids are charged.

In one embodiment, 10-30% of said cholesterol is located by the fatty acid moiety of said ceramides and 90-70% of said cholesterol is located by the sphingoid moiety of the ceramides. In one embodiment approximately 15-35%, such as 25-30%, of said cholesterol is located by the fatty acid moiety of said ceramides and approximately 85-65%, such as 75-70%, of said cholesterol is located by the ceramide sphingoid moiety. In one embodiment, 20-30% of said cholesterol is located by the fatty acid moiety of said ceramides and 80-70% of said cholesterol is located by the sphingoid moiety of the ceramides. In one embodiment approximately 22-28%, such as 23-27%, such as 24-26% of said cholesterol is located by the fatty acid moiety of said ceramides and 78-72%, such as 77-73%, such as 76-74% of said cholesterol is located by the sphingoid moiety of the ceramides. In one embodiment, approximately 25% of said cholesterol is located by the fatty acid moiety of said ceramides and approximately 75% of said cholesterol is located by the sphingoid moiety of the ceramides.

In one particular embodiment, said cholesterol located by the fatty acid moiety of said ceramides is arranged such that its hydroxyl group can form hydrogen bonds with the polar ceramide head groups and its tail is arranged in the general orientation of the ceramide sphingoid side chains or in the general orientation of the ceramide fatty acid side chains, depending on which side of the ceramide head group said cholesterol is located.

In one embodiment of said method, there is provided a model wherein 0-2%, such as 0% of the cholesterol molecules are replaced by cholesterol sulfate molecules.

In another particular embodiment of said method, there is provided a model wherein the ratio of the molar concentration of ceramides:free fatty acids:cholesterol in said model of the stratum corneum lipid matrix is approximately 1:1:1 based on the molar concentration of all components except water. As used herein the term "approximately 1:1:1" encompasses variants of the ratio 34:33:33. Thus any one of ceramides, free fatty acids and cholesterol may be present in 33-34% based on the molar concentration of all components except water provided that the total molar concentration of ceramides, free fatty acids and cholesterol is 100%. In particular embodiment of said method, there is provided a model wherein the ratio of the molar concentration of ceramides:free fatty acids:cholesterol in said model of the stratum corneum lipid matrix is approximately 34:33:33, 33:34:33 or 33:33:34 based on the molar concentration of all components except water.

In one embodiment of the present method, the non O-acyl ceramides of said model are non ceramide EOS and non ceramide EOP and non ceramide EOH.

In one embodiment of the present method, the ceramides of said model are ceramides EOS, NS and AS or ceramides EOP, NP and AP. In other embodiments, the ceramides may be ceramides EOP, AP and NS; ceramides EOP, AS and NP; ceramides EOS, AP and NP; ceramides EOP, AS and NS; ceramides EOS, AP and NS; ceramides EOS, AS and NP; ceramides EOS, AS and NP; ceramides EOS, AP and NS; ceramides EOP, AS and NS; ceramides EOS, AP and NP; ceramides EOP, AS and NP; ceramides EOP, AP and NS; ceramide EOH, AP and NP; ceramide EOH, AS and NS; ceramide EOH, AP and NS; or ceramide EOH, AS and NP.

In one particular embodiment of said model, 0% of the free fatty acids are charged and 0% of the cholesterol molecules are replaced by cholesterol sulfate molecules.

In one particular embodiment, said model of the stratum corneum lipid matrix comprises the following:
  i) 33-34% total ceramides based on the molar concentration of all components except water, of which 95-100% are in extended configuration, and
    wherein 13% of said total ceramides are ceramide EOS and 87% of said total ceramides are non O-acyl ceramides and wherein the sphingoid moiety of said non O-acyl ceramides has a length of 18 carbons and the fatty acid moiety of said non O-acyl ceramides has a chain length distribution approximately according to the following:
      5.1% of non O-acyl ceramides are ceramide NP which have a fatty acid chain length of 20 carbons;
      10.3% of non O-acyl ceramides are ceramide NP which have a fatty acid chain length of 22 carbons;
      20.5% of non O-acyl ceramides are ceramide NP which have a fatty acid chain length of 24 carbons;
      20.5% of non O-acyl ceramides are ceramide NS which have a fatty acid chain length of 24 carbons;
      30.8% of non O-acyl ceramides are ceramide NP which have a fatty acid chain length of 26 carbons;
      10.3% of non O-acyl ceramides are ceramide NP which have a fatty acid chain length of 28 carbons; and
      2.5% of non O-acyl ceramides are ceramide NP which have a fatty acid chain length of 30 carbons, and
  ii) 33-34% fatty acid based on the molar concentration of all components except water, wherein the fatty acid chain length distribution is approximately according to the following:
      4.5% of the fatty acids have a fatty acid chain length of 20 carbons;

9.1% of the fatty acids have a fatty acid chain length of 22 carbons;

34.1% of the fatty acids have a fatty acid chain length of 24 carbons;

27.3% of the fatty acids have a fatty acid chain length of 26 carbons;

9.1% of the fatty acids have a fatty acid chain length of 28 carbons; and 15.9% of the fatty acids have a fatty acid chain length of 30 carbons;

iii) 33-34% cholesterol, based on the molar concentration of all components except water, wherein approximately 25% of said cholesterol is located by the ceramide fatty acid moiety of said ceramides and approximately 75% of said cholesterol is located by the ceramide sphingoid moiety; and iv) 1 water molecule per ceramide molecule.

In one particular embodiment of said model, 0% of the free fatty acids are charged and 0% of the cholesterol molecules are replaced by cholesterol sulfate molecules.

As used herein, the term "molecular designators" refers to properties of molecules that may be used to describe said molecules. Non-limiting examples of molecular designators include atomic coordinates and force field parameters. Thus, in one embodiment of the method as disclosed herein, the provided molecular designators are atomic coordinates; force field parameters; or atomic coordinates and force field parameters. In particular, said force field parameters may be at least one force field parameter selected from the group consisting of non-bonded interactions and bonded interactions. Non-bonded interactions may be selected from the group consisting of Van der Waals and electrostatic interactions. Bonded interactions may be selected from the group consisting of bonds, angles and dihedral angles of a compound.

In one embodiment of the method as described herein, said model of the stratum corneum lipid matrix is such that the calculated permeability coefficient log $K_{Pcalc}$ (in cm/h) calculated for water is in the range of −2.9 to −5.0, such as −3.2 to −4.6, such as −3.5 to −4.5. In one embodiment said log $K_{Pcalc}$ value is calculated as described in Example II. To clarify, the present inventive method utilizes a model which exhibits said calculated permeability coefficient log $K_{Pcalc}$ (in cm/h).

In one embodiment said log $K_{Pcalc}$ value is from total simulation time of 3 µs. In one embodiment said log $K_{Pcalc}$ value is from total simulation time of 3 µs with 30 pulls in each direction, pulling at approximately 0.2 nm/ns and with an umbrella potential of 15,000 kJ/mol/nm$^2$.

The skilled person will appreciate that the method and model as disclosed herein may have several applications in the field related to skin permeability and predictions thereof. For example, it may be of interest to predict the effect of a modification in a given compound, for example a drug candidate, on the stratum corneum permeability to said compound. It is envisioned that the permeability of the stratum corneum lipid matrix to a first unmodified compound is compared to the permeability of the stratum corneum lipid matrix to a second modified compound. Non-limited modifications include substitutions, for example substitutions of a halogen with a different halogen, changes of chirality, addition or removal of a hydroxyl group and introduction of single, double or triple bonds within said second compound. The skilled person is aware of additional modifications that may be made in order to obtain said second compound.

It is to be understood that said method is not limited to structurally related compounds, but is equally applicable to any first and any second compound.

Thus in a second aspect of the present disclosure, there is provided a method of predicting the effect of a structural difference between a first compound and a second compound on the permeability of the stratum corneum lipid matrix to said compounds, comprising the steps of a) providing a model of the stratum corneum lipid matrix as defined herein;

b) providing molecular designators as defined herein for the first compound;

c) providing molecular designators as herein for the second compound;

d) calculating the permeability of the stratum corneum lipid matrix to the first compound via means of computer simulation using the model of step a) and the molecular designators of step b);

e) calculating the permeability of the stratum corneum lipid matrix to the second compound via means of computer simulation using the model of step a) and the molecular designators of step c); and f) comparing the obtained predicted permeability to said first compound calculated in step d) and to said second compound calculated in step e).

It will be understood that the molecular designators provided in steps b) and c) of said method not have to be the same type of molecular designators. For example the molecular designators for said first compound may include force field parameters such as non-bonded interactions, while the molecular designators for said second compound may include force field parameters such as bonded interactions.

The skilled person will understand that the scope of the methods presently disclosed is not limited to the order in which the steps are performed provided the comparison of step f) can be made. For example, it will be appreciated that for example steps a)-c) above may be performed in any order. Also, steps d) and e) may be performed in any order. Additionally, it is possible to perform the steps a), b) and d) first and next the steps c), e) and f). Hence, the steps of any of the methods disclosed herein may be performed in a different order, provided that the information for the subsequent step is provided any one of the previous step. This same line of reasoning regarding the order of performance of the steps applies to all methods presently disclosed and will not be repeated for the sake of brevity.

As briefly discussed above, in one embodiment of the method of predicting the effect of a structural difference between a first compound and a second compound on the permeability of the stratum corneum lipid matrix to said compounds disclosed herein, said second compound is a modification of the first compound. Examples of such modifications that may be made to a first compound in order to obtain a second compound include, but are not limited to adding, removing or replacing functional groups, such as hydroxyl groups or other polar groups, halogens, acidic or basic moieties etc., rigidification of the structure and alkyl chain extensions.

It will be understood by the skilled person that the disclosure of the method according to the first aspect is equally relevant for the second and further aspects of the present disclosure, in particular any details regarding the model of the stratum corneum lipid layer, and such details will not be repeated in the context of the second and further aspects for the sake of brevity.

The skilled person will realize that this second aspect can also be expressed as an embodiment of the first aspect as disclosed herein. For the sake of brevity, any disclosure made in connection with the second aspect is equally relevant for this embodiment of the first aspect and the skilled person will appreciate this. Thus in one embodiment, said method according to the first aspect as disclosed herein, there is provided a method further comprises the steps of:

d) providing the molecular designators of a second compound to which the permeability of the stratum corneum lipid matrix is to be predicted;

e) calculating, via means of computer simulation, the predicted permeability of the stratum corneum lipid matrix to said second compound using said model and the molecular designators of the said second compound; and f) comparing the obtained predicted permeability to said first compound calculated in step c) and to said second compound calculated in step d) and predicting the effect of a structural difference between a first compound and a second compound on the permeability of the stratum corneum lipid matrix to said compounds.

It will be understood that the molecular designators provided in steps b) and d) of said method do not have to be the same type of molecular designators. The skilled person will understand that the scope of the method presently disclosed is not limited to the order in which the steps are performed provided the comparison of step f) can be made.

The permeability of skin is difficult to measure both in vivo and in vitro. In vivo experiments on humans are expensive and require and may require approval by an ethical committee. In vitro measurements on excised human skin is usually performed using diffusion cells, or Franz cells, usually with water as vehicle, or donor and receptor, but other solvents can be used. The experiments are usually performed over a long period of time (24 h to 48 h) during which the vehicle diffuses into the skin increasing the permeability. It has been shown that hydrated stratum corneum may increase its permeability 10-fold (Idson, 1983 and van der Merwe and Ackermann, 1987). Therefore it has been proposed that data from diffusion cells might not be representative of normal skin and should be evaluated carefully (van der Merwe and Ackermann, 1987). Also, any damages to the skin membrane, from e.g. freezing, would increase its permeability. The present invention provides a method for prediction of permeability making use of a model of the stratum corneum lipid matrix as disclosed herein. The lipid matrix is the main determinant of permeation. The lipid matrix model as defined herein is provided in a state closely resembling the native state. Therefore, the prediction methods utilizing the present model according to the aspects disclosed herein, provide high accuracy of prediction.

The permeability of the stratum corneum to most compounds is low and the stratum corneum may therefore pose an obstacle to e.g. topical administration of drugs and other compounds. However, for some compounds the permeation of the stratum corneum is undesirable, for example in the case of certain toxins. Thus, there is a need to add permeability modifying agents (PMA) to certain compounds or compositions comprising certain compounds to obtain a desirable level of permeation of said compounds. PMAs may be either permeation enhancing agents or permeation decreasing agents. There is a need in the field to be able to predict the permeability of a stratum corneum lipid matrix in the presence of at least one chemical permeability modifying agent (PMA) to a compound. Such predictions may be beneficial during development of drugs and/or pharmaceutical compositions with desired permeability properties. The ability to predict the permeability of a stratum corneum lipid matrix in the presence of at least one chemical permeability modifying agent (PMA) to a compound allows for faster and less expensive identification and development of drug candidates and pharmaceutical compositions for topical administration, such as topical administration to the skin. Advantageously, both the effect on the permeability of the system as well as how the PMA affects the system may be studied.

Thus, in a third aspect of the present disclosure there is provided a method for predicting the permeability of a stratum corneum lipid matrix with at least one chemical permeability modifying agent (PMA) to a compound, comprising the steps of:

a) providing a model of the stratum corneum lipid matrix as defined herein;

b) providing the molecular designators as defined herein of said at least one PMA;

c) providing, via means of computer simulation using the model and the molecular designators of the at least one PMA, a modified model of the stratum corneum lipid matrix with the at least one PMA;

d) providing the molecular designators as defined herein for said compound; and e) calculating the predicted permeability to said compound from step d) of the stratum corneum lipid matrix and the at least one PMA via means of computer simulation using the modified model of step c).

It may be desirable that said method allows for the comparison of the permeability of the stratum corneum lipid layer to the compound in the presence and in the absence of a PMA.

Again, the order of performance of the steps of this method may be different from above, provided that provided that the information for the subsequent step is provided any one of the previous step. For example, steps a and b may be performed in any order, however before step c). Step d) may be performed before or after any of steps a), b) and c).

Thus, in a related aspect there is provided method for predicting the effect of at least one chemical permeability modifying agent (PMA) on the permeability of a stratum corneum lipid matrix to a compound, comprising the steps of:

a) providing a model of the stratum corneum lipid matrix as defined herein;

b) providing the molecular designators as defined herein of said at least one PMA;

c) providing, via means of computer simulation using the model and the molecular designators of the at least one PMA, a modified model of the stratum corneum lipid matrix with the at least one PMA;

d) providing the molecular designators as defined herein for said compound;

e) calculating the predicted permeability of the stratum corneum lipid matrix to said compound from step d) via means of computer simulation using the model from step a);

f) calculating the predicted permeability to said compound from step d) of the stratum corneum lipid matrix and the at least one PMA via means of computer simulation using the modified model of step c); and g) comparing the obtained predicted permeability to said compound calculated in step e) and step f).

The order of performance of the steps of this method may be different from above, provided that provided that the information for the subsequent step is provided any one of the previous step. For example, steps a) and b) may be performed in any order, however before step c). Step d) may be performed before or after any of steps a), b) and c).

It will be appreciated that the calculations in the method above may be performed in parallel or in sequence. Thus, in one embodiment there is provided a method for predicting the effect of at least one PMA on the permeability to a compound of a stratum corneum lipid matrix as disclosed herein, wherein the calculations in step e) and f) are performed in parallel or in sequence.

The skilled person will realize that the third aspect and related fourth aspect can also be expressed as embodiments of the first aspect as disclosed herein. For the sake of brevity, any disclosure made in connection with the third and related fourth aspect is equally relevant for this embodiment of the first aspect and the skilled person will appreciate this. Thus in one embodiment, said method according to the first aspect as disclosed herein, there is provided a method wherein step a) further comprises the steps of
- a1) providing the molecular designators as defined herein for at least one chemical permeability modifying agent (PMA);
- a2) providing, via means of computer simulation using the model according to a) and the molecular designators of the at least one PMA according to a1), a modified model of the stratum corneum lipid matrix with the at least one PMA;

wherein said modified model according to a2) is used for predicting the permeability of a stratum corneum lipid matrix with at least one PMA to the compound in step c).

In one embodiment, said method further comprises the steps of
- d) calculating the predicted permeability of the stratum corneum lipid matrix to said compound from step b) via means of computer simulation using the model from step a); and
- e) comparing the obtained predicted permeability to said compound calculated in step c) and step d), whereby obtaining a prediction of the effect of at least one PMA on the permeability of a stratum corneum lipid matrix to a compound.

It will be understood that the molecular designators provided in steps a1) and b) of said method do not have to be the same type of molecular designators. The skilled person will understand that the scope of the method presently disclosed is not limited to the order in which the steps are performed provided that the information for the subsequent step is provided any one of the previous step.

It will be appreciated that the methods according to the second and thirds aspects are not limited to a number of PMAs and may involve one PMA, two, three, four or more PMAs. In one embodiment, there is provided said method, wherein said at least one PMA is two, three, four or more PMAs.

In one embodiment of the method for predicting the effect of at least one PMA on the permeability to a compound of a stratum corneum lipid matrix according as disclosed herein, the modified model of the stratum corneum lipid matrix in step c) is formed by addition of said at least two, three, four or more PMAs to the model followed by equilibration. In other embodiments, it may be envisaged that said at least two, three, four or more PMAs are added one by one with equilibration after the addition of each PMA.

Furthermore, the scope of the present disclosure encompasses a method for predicting the effect of at least one PMA on the organization of a stratum corneum lipid matrix. For example the method allows for predictions, such as if said PMA forms pores in the lipid matrix, forms vesicles or distorts the lipid chain packing in general, based on said molecular simulations. The prediction and understanding of the effect exerted by at least one PMA on the molecular organization is considered useful, for e.g. classification of PMAs and possibly for regulatory authorities to improve evaluating formulations and their effect.

Thus, in a fifth aspect there is provided a method for predicting the effect of at least one PMA on the organization of a stratum corneum lipid matrix, comprising the steps of:
- a) providing a model of the stratum corneum lipid matrix as defined herein;
- b) providing the molecular designators as defined herein for said PMA; and
- c) predicting, via means of computer simulation using the model of step a) and the molecular designators of step b), if said PMA mainly interacts with the head groups of the ceramides, with the sphingoid moieties or with the fatty acid moieties of said model of the stratum corneum lipid matrix.

Again, the order of performance of the steps of this method may be different from above. For example, step a) and b) can be performed in any order.

A PMA may lead to e.g. formation of pores, vesicles or disturbances in the lipid moieties of the ceramides of the said model of the stratum corneum lipid matrix.

The outcome of the prediction method provides information regarding the organization of said stratum corneum lipid matrix in the presence of the PMA. Non limiting examples of such organization include the formation of pores in the lipid matrix and/or formation of vesicles which distort the packing of lipid chains. The predicted effect of said PMA may be used to find one or more candidate PMA for modification (enhancement or decrease) of the permeability of the stratum corneum to a compound or group of compounds of interest. Using water as a PMA will also allow studying the effects of hydration of the skin and find a level of hydration that gives permeability values similar to those obtained from in vitro methods.

It will be appreciated that the identification of a suitable PMA for a compound of interest is of importance for example in the field of drug development, development of cosmetics, and composition development for pharmaceutical or cosmetic uses and development of compositions containing harmful and/or toxic compounds, just to mention a few. A method which allows for identifying a PMA for a compound which has a desired effect on the permeability of a stratum corneum lipid matrix to said compound is useful and may improve and shorten development and/or research time of compositions and decrease cost associated with said development, for example by decreasing the number of in vivo experiments needed.

Yet another aspect of the present disclosure encompasses a method of identifying a PMA for a compound, comprising the steps of
- a) providing a model of the stratum corneum lipid matrix as defined herein;
- b) providing the molecular designators as defined herein of at least one candidate PMA;
- c) providing, via means of computer simulation using the model of step a) and the molecular designators of the at least one candidate PMA of step b), a modified model of the stratum corneum lipid matrix with the at least one candidate PMA;
- d) providing the molecular designators as defined herein for said compound;

e) calculating the predicted permeability to said compound from step d) of the stratum corneum lipid matrix via means of computer simulation using the model of step a);
f) calculating the predicted permeability to said compound from step b) of the stratum corneum lipid matrix with said at least one candidate PMA from step c) via means of computer simulation using the modified model of step c) and the molecular designators of step d), and
g) comparing the obtained predicted permeability to said compound in step e) and to said compound and said at least one candidate PMA in step f).

As previously mentioned, the order of performance of the steps of this method may be different from above, provided that the information for the subsequent step is provided by any one of the previous step. The skilled person is aware of that the order may be different, for example step d) can be performed before step c).

Thus, in a related aspect encompassed by the present disclosure, there is provided a method for identifying a PMA for a compound which has a desired effect on the permeability of a stratum corneum lipid matrix to said compound, comprising the steps of
a) providing a model of the stratum corneum lipid matrix as defined herein;
b) providing the molecular designators as defined herein of each candidate PMA;
c) providing, via means of computer simulation using the model of step a) and the molecular designators of a candidate PMA of step b), a modified model of the stratum corneum lipid matrix with the candidate PMA;
d) providing the molecular designators as defined herein for said compound;
e) calculating the predicted permeability to said compound from step d) of the stratum corneum lipid matrix via means of computer simulation using the model of step a) and the molecular designators of step d);
f) calculating the predicted permeability to said compound from step d) of the stratum corneum lipid matrix with the candidate PMA from step b) via means of computer simulation using the modified model of step c) and the molecular designators of step d);
g) comparing the obtained predicted permeability to said compound calculated in step e) and f); and
h) repeating at least steps c, f and g) for said compound and each candidate PMA to be tested until the desired effect is predicted.

Thus the method allows for the identification or PMAs which are predicted to give rise to the desired effect on the permeability of a stratum corneum lipid matrix to said compound. It is envisioned that the candidate one or more PMAs may subsequently be evaluated in vivo, if required.

As previously mentioned, the order of performance of the steps of this method may be different from above, provided that the information for the subsequent step is provided by any one of the previous step. The skilled person is aware of that the order may be different, for example step d) can be performed before step c).

In the context of the above-mentioned aspects the computer simulations used comprise for example Molecular Dynamics simulations (Alder and Wainwright, 1959). The skilled person will appreciated that other computational and/or simulation methods may be used without departing from the scope of the present disclosure.

Also, in the context of the present disclosure and in embodiments of the aspects related to PMA (including aspects 3 to 7), the PMA may be permeability enhancing agent or a permeability decreasing agent. For example it may be permeability enhancing agent, such as a chemical permeability enhancing agent. Non-limiting examples of such PMAs include water; sulfoxides and related compounds, such as dimethylsulphoxide (DMSO) and dimethylformamide (DMF); azone and derivatives thereof; pyrrolidones, such as N-methyl-2-pyrrolidone (NMP) and 2-pyrrolidone (2P); fatty acids, such as oleic acid; alcohols and glycols, such as ethanol; urea analogues, such as cyclic urea; essential oils, terpenes and terpenoids, such as eucalyptus oil, I-menthol and d-limonene; and sesquiterpene. Additionally, PMA in this context may be additional free fatty acids and/or ceramides that added to compositions, such as cosmetic compositions. Such compounds are expected to affect the organization of the stratum corneum lipid matrix in a way that affects the permeability of said stratum corneum lipid matrix to a compound of interest.

Thus, in one embodiment of said aspects, said PMA is selected from the group consisting of water:sulfoxides and related compounds, such as dimethylsulphoxide (DMSO) and dimethylformamide (DMF); azone and derivatives thereof; pyrrolidones, such as N-methyl-2-pyrrolidone (NMP) and 2-pyrrolidone (2P); fatty acids, such as oleic acid; alcohols and glycols, such as ethanol; urea analogues, such as cyclic urea; essential oils, terpenes and terpenoids, such as eucalyptus oil, I-menthol and d-limonene; sesquiterpene, free fatty acids and ceramides, such as the group consisting of water:sulphoxides and related compounds, such as dimethylsulphoxide (DMSO) and dimethylformamide (DMF); azone and derivatives thereof; pyrrolidones, such as N-methyl-2-pyrrolidone (NMP) and 2-pyrrolidone (2P); fatty acids, such as oleic acid; alcohols and glycols, such as ethanol; urea analogues, such as cyclic urea; essential oils, terpenes and terpenoids, such as eucalyptus oil, I-menthol and d-limonene; and sesquiterpene. In one particular embodiment, said PMA is selected from the group consisting of azone, DMSO, ethanol, and water.

It will be appreciated that encompassed by the present disclosure are also uses of the model of the stratum corneum lipid matrix as disclosed herein, such as use of the model for predicting the permeability of a stratum corneum lipid matrix to a compound, use of the model for predicting the permeability of a stratum corneum lipid matrix with at least one chemical permeability modifying agent (PMA) to a compound, use of the model for predicting the effect of at least one PMA on the permeability of a stratum corneum lipid matrix to a compound, use of the model for predicting the effect of at least one PMA on the organization of a stratum corneum lipid matrix, use of the model for identifying a PMA for a compound which has a desired effect on the permeability of a stratum corneum lipid matrix, and use of the model for identifying a PMA for a compound.

Also encompassed are computer program products comprising computer program code which, when executed by a device having processing capability, enables the device to provide a model of the stratum corneum lipid matrix as defined herein.

Also encompassed is a computer readable medium carrying computer program code which, when executed by a device having processing capability, enables the device to provide a model of the stratum corneum lipid matrix as defined herein. Such computer readable medium can be any kind of medium through which the computer program code is made available to a device, and one example of such computer readable medium is a non-volatile storage medium.

While the invention has been described with reference to various exemplary aspects and embodiments, it will be understood by those skilled in the art that various changes may be made and equivalents may be substituted for elements thereof without departing from the scope of the invention. In addition, many modifications may be made to adapt a particular situation or molecule to the teachings of the invention without departing from the essential scope thereof. Therefore, it is intended that the invention not be limited to any particular embodiment contemplated, but that the invention will include all embodiments falling within the scope of the appended claims.

BRIEF DESCRIPTION OF THE FIGURES

FIGS. 8a-d illustrate top views of ceramides, cholesterol, free fatty acids and water, respectively, in a stratum corneum lipid matrix before computer simulation;

FIGS. 9a-d illustrate side views of ceramides, cholesterol, free fatty acids and water, respectively, in a stratum corneum lipid matrix before computer simulation;

FIGS. 10a-d illustrate side views of ceramides, cholesterol, free fatty acids and water, respectively, in a model of a stratum corneum lipid matrix in accordance with a method of the present disclosure;

FIGS. 11a-e illustrate the permeability modifying agents azone, DMSO, oleic acid, stearic acid and water, respectively and their organization within a model of a stratum corneum lipid matrix in accordance with a method of the present disclosure; and FIGS. 12a-b illustrates schematically and very simplified a computer program product and a computer readable medium according to the invention.

EXAMPLES

Summary

The following Examples disclose specific details on how to carry out methods according to the present disclosure to calculate for example the permeability of the stratum corneum lipid matrix to various compounds.

As a prerequisite, force field parameters (interaction parameters) for molecules used in the MD simulations are needed. Descriptions of most of these compounds/molecules may be found in common biochemical force fields, such as e.g. the CHARMM36 lipid force field (Klauda et al., 2010; Venable et al., 2014), with modifications as may be seen in Tables 1-6. The interaction parameters of permeants may be obtained using e.g. STaGE (Lundborg and Lindahl, 2014), which in turn uses Open Babel (O'Boyle et al., 2011) and MATCH (Yesselman et al., 2012) to generate force field parameters from a set of atomic coordinates, and/or covalent bonds, for generic organic molecules.

For a stratum corneum system (i.e. a stratum corneum lipid matrix) as described herein, the following components may be needed:

Non O-acyl ceramides, including:
Ceramide NP with sphingoid chain C18 and fatty acid chain in the following range: C20, C22, C24, C26, C28 and C30. The ceramide NP parameters may be based on ceramide NS with head group parameters optimized to improve agreement with quantum mechanical torsion scans and ceramide NP crystal structure data; and
Ceramide NS with sphingoid chain C18 and fatty acid chain C24. Head group parameters from ceramide NP that were modified and were similar in ceramide NS may be transferred from ceramide NP,
O-acyl ceramides, including Ceramide EOS with parameters based on the ceramide NS parameters (including head group modifications) and with basic CHARMM36 parameters for the introduced ester group and unsaturations;
Saturated free fatty acids in the following range: C20, C22, C24, C26, C28 and C30;
Cholesterol, and
Water, based on e.g. the TIP3P water model.

Figure 1A:
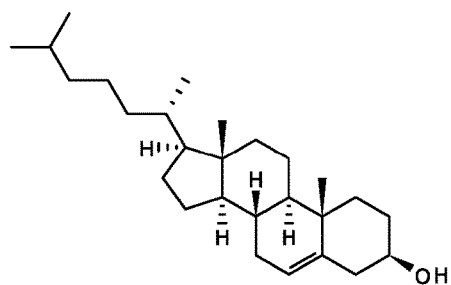
FIGS. 1a-f illustrate structural formulas for compounds included in a model of the stratum corneum lipid matrix.
Figure 1B:
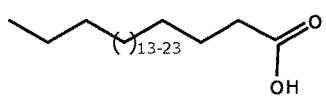
Figure 1C:
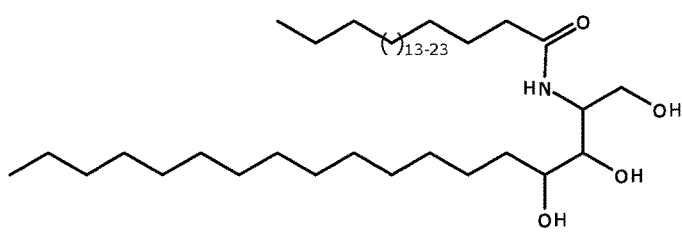
Figure 1D:
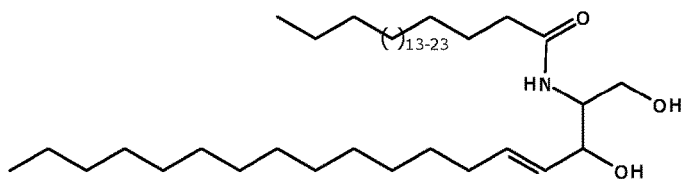
Figure 1E:
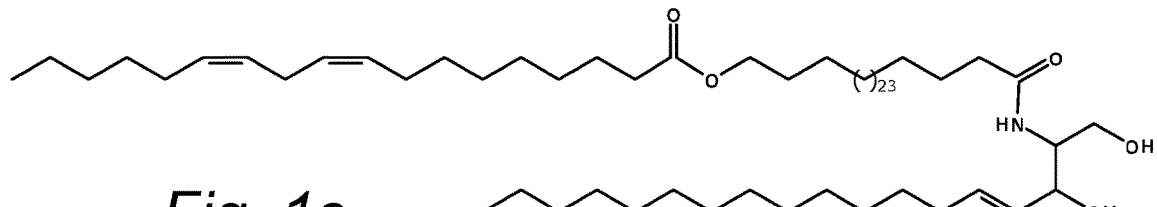

FIG. 1a illustrates a structural formula for cholesterol, FIG. 1b illustrates a structural formula for free fatty acid, FIG. 1c illustrates a structural formula for ceramide NP, FIG. 1d illustrates a structural formula for ceramide NS, and FIG. 1e illustrates a structural formula for ceramide EOS. Figure if illustrates the ceramide NP head group and the atoms are numbered for reference to Tables 1-6, showing what CHARMM36 parameters were added or modified in order to run simulations with ceramide NP.

TABLE 1

Figure 1F:
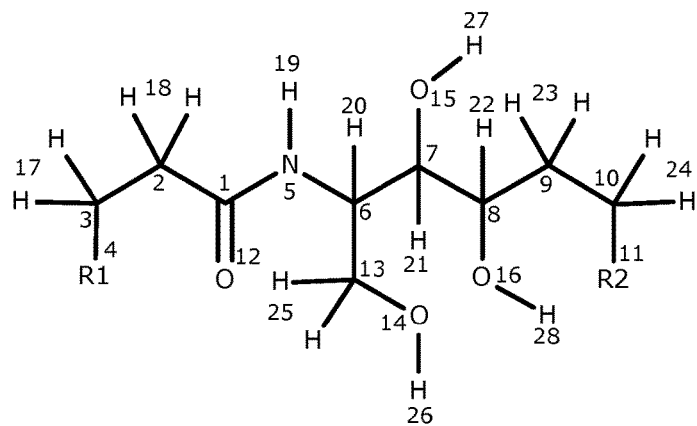
Figure 2A:
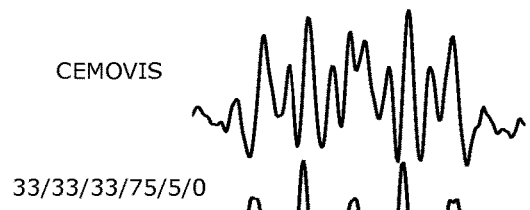
FIGS. 2a-g illustrate experimental CEMOVIS intensity profiles and intensity profiles calculated in accordance with a method of the present disclosure, using a model with varying number of water molecules per ceramide.
Figure 2B:
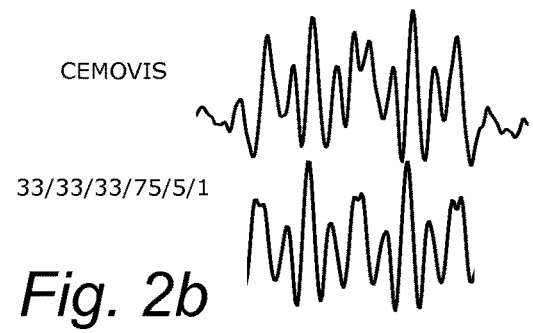
Figure 2C:
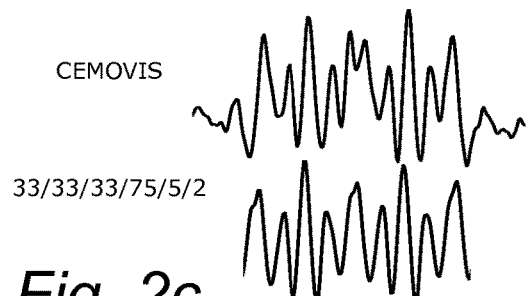
Figure 2D:
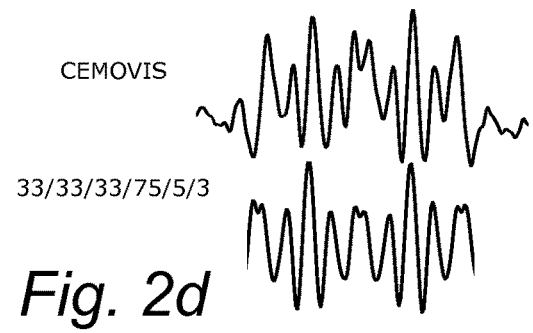
Figure 2E:
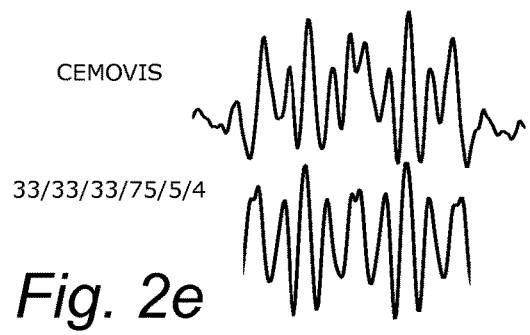
Figure 2F:
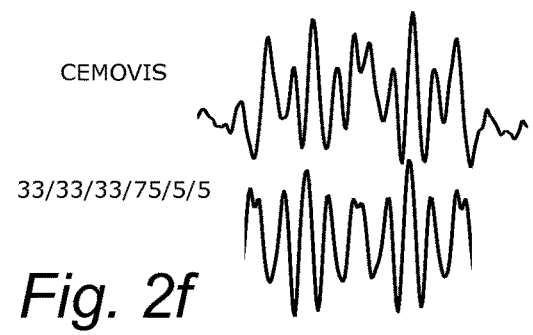
Figure 2G:
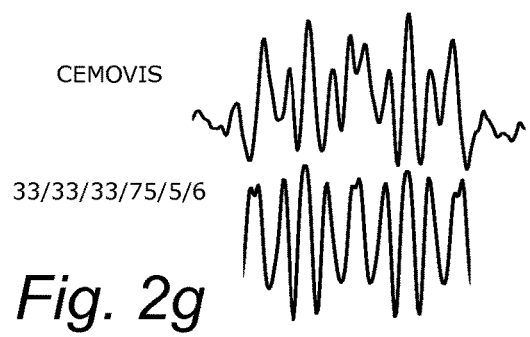
Figure 3A:
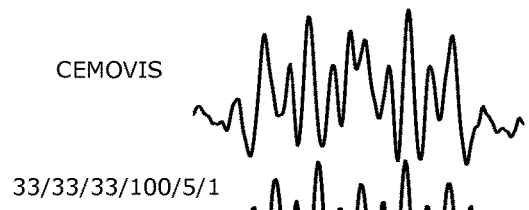
FIGS. 3a-h illustrate experimental CEMOVIS intensity profiles and intensity profiles calculated in accordance with a method of the present disclosure, using a model with varying amount of cholesterol associated with the ceramide sphingoid chains.
Figure 3B:
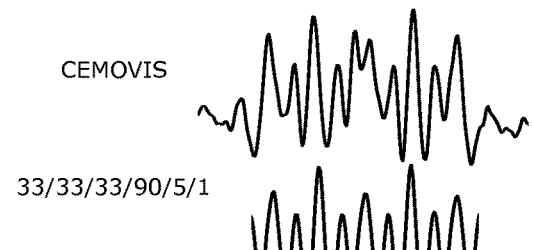
Figure 3C:
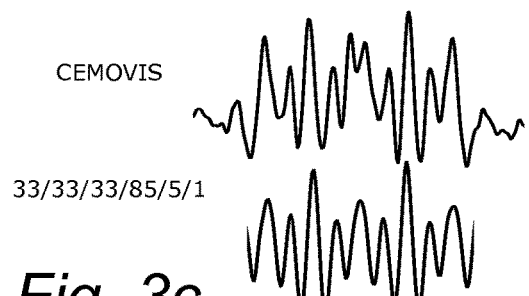
Figure 3D:
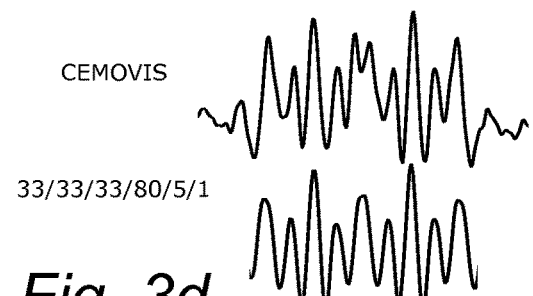
Figure 3E:
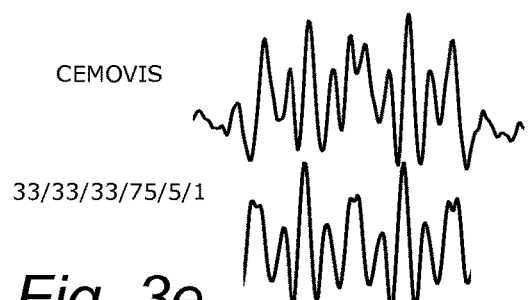
Figure 3F:
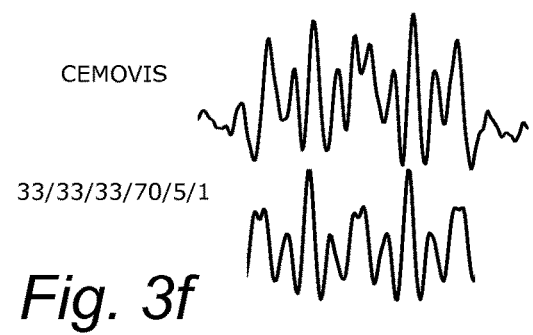
Figure 3G:
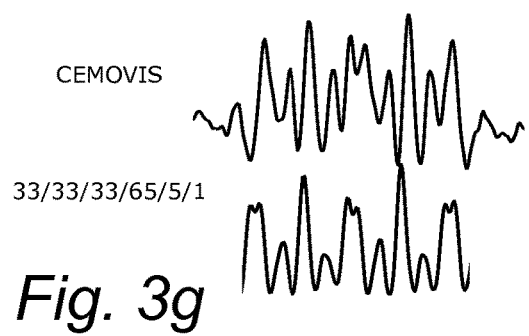
Figure 3H:
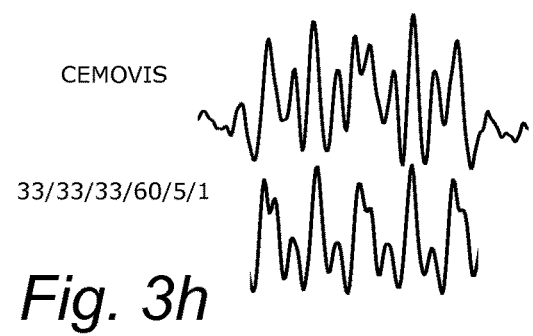

Modified CHARMM36 atom pair interaction parameters for ceramide NP. Atom numbers correspond to the atom numbers in FIG. 1f and the CHARMM36 atom types are given in parentheses.

| Atom 1 | Atom 2 | σ (nm) | ξ (kJ/mol) |
| --- | --- | --- | --- |
| 12 (O) | 17, 18, 25, 23, 24 (HAL2) | 0.22500 | 0.47500 |
| 14, 15, 16 (OHL) | 17, 18, 25, 23, 24 (HAL2) | 0.22500 | 0.47500 |
| 14, 15, 16 (OHL) | 26, 27, 28 (OHL) | 0.132726 | 0.1108657 |

TABLE 2

Modified CHARMM36 bond parameters for ceramide NP. Atom numbers correspond to the atom numbers in FIG. 1f and the CHARMM36 atom types are given in parentheses.

| Atom 1 | Atom 2 | $b_0$ (nm) | $k_b$ (kJ/mol/nm$^2$) |
| --- | --- | --- | --- |
| 7 (CTO1) | 8 (CTO1) | 0.15000 | 1.86188e+05 |

TABLE 3

Modified CHARMM36 angle parameters for ceramide NP.
Atom numbers correspond to the atom numbers in FIG. 1f and
the CHARMM36 atom types are given in parentheses.

| Atom 1 | Atom 2 | Atom 3 | $\theta_0$ (deg) | $k_\theta$ (kJ/mol/rad$^2$) | $r_{13}$ (nm) | $k_{UB}$ (kJ/mol/nm$^2$) |
|---|---|---|---|---|---|---|
| 1 (C) | 2 (CTL2) | 3 (CTL2) | 115.00 | 435.1360 | 0.0000 | 0.0000 |
| 1 (C) | 5 (NHL) | 6 (CTL1) | 121.00 | 500.0000 | 0.0000 | 0.0000 |
| 1 (C) | 5 (NHL) | 19 (H) | 121.00 | 284.5120 | 0.0000 | 0.0000 |
| 5 (NHL) | 6 (CTL1) | 13 (CTO2) | 111.08 | 585.7600 | 0.0000 | 0.0000 |
| 7 (CTO1) | 6 (CTL1) | 13 (CTO2) | 114.88 | 488.2728 | 0.2561 | 9.33869e+03 |
| 6 (CTL1) | 7 (CTO1) | 8 (OHL) | 114.88 | 435.1360 | 0.0000 | 0.0000 |
| 6 (CTL1) | 7 (CTO1) | 15 (OHL) | 111.09 | 585.7600 | 0.0000 | 0.0000 |
| 8 (CTO1) | 7 (CTO1) | 15 (OHL) | 110.10 | 520.0000 | 0.0000 | 0.0000 |
| 8 (CTO1) | 7 (CTO1) | 21 (HAL1) | 110.10 | 288.6960 | 0.2179 | 1.88531e+04 |
| 7 (CTO1) | 8 (CTO1) | 9 (CTL2) | 113.50 | 488.2728 | 0.2561 | 9.33869e+03 |
| 7 (CTO1) | 8 (CTO1) | 16 (OHL) | 110.10 | 520.0000 | 0.0000 | 0.0000 |
| 9 (CTL2) | 8 (CTO1) | 16 (OHL) | 110.10 | 633.4576 | 0.0000 | 0.0000 |
| 9 (CTL2) | 8 (CTO1) | 22 (HAL1) | 110.10 | 288.6960 | 0.2179 | 1.88531e+04 |
| 8 (CTO1) | 9 (CTL2) | 10 (CTL2) | 113.50 | 488.2728 | 0.2561 | 9.33869e+03 |
| 8 (CTO1) | 9 (CTL2) | 23 (HAL2) | 110.10 | 221.7520 | 0.2179 | 1.88531e+04 |
| 6 (CTL1) | 13 (CTO2) | 14 (OHL) | 113.50 | 633.4576 | 0.0000 | 0.0000 |

TABLE 4

Modified CHARMM36 proper torsion parameters for ceramide NP.
Atom numbers correspond to the atom numbers in FIG. 1f and
the CHARMM36 atom types are given in parentheses.

| Atom 1 | Atom 2 | Atom 3 | Atom 4 | $\Phi_s$ (deg) | $k_\Phi$ (kJ/mol) | Multiplicity |
|---|---|---|---|---|---|---|
| 5 (NHL) | 1 (C) | 2 (CTL2) | 3 (CTL2) | 0.000 | 1.400 | 1 |
| 5 (NHL) | 1 (C) | 2 (CTL2) | 3 (CTL2) | 180.0 | 0.400 | 2 |
| 5 (NHL) | 1 (C) | 2 (CTL2) | 3 (CTL2) | 0.000 | 0.550 | 3 |
| 5 (NHL) | 1 (C) | 2 (CTL2) | 3 (CTL2) | 180.0 | 0.350 | 6 |
| 12 (O) | 1 (C) | 2 (CTL2) | 3 (CTL2) | 180.0 | 1.000 | 1 |
| 12 (O) | 1 (C) | 2 (CTL2) | 3 (CTL2) | 0.000 | 0.500 | 3 |
| 18 (HAL2) | 2 (CTL2) | 3 (CTL2) | 17 (HAL2) | 0.000 | 0.000 | 3 |
| 1 (C) | 5 (NHL) | 6 (CTL1) | 7 (CTO1) | 0.000 | 13.00 | 1 |
| 1 (C) | 5 (NHL) | 6 (CTL1) | 7 (CTO1) | 180.0 | 9.000 | 2 |
| 1 (C) | 5 (NHL) | 6 (CTL1) | 7 (CTO1) | 180.0 | 6.500 | 3 |
| 1 (C) | 5 (NHL) | 6 (CTL1) | 13 (CTO2) | 0.000 | 12.00 | 1 |
| 1 (C) | 5 (NHL) | 6 (CTL1) | 13 (CTO2) | 180.0 | 5.500 | 2 |
| 1 (C) | 5 (NHL) | 6 (CTL1) | 13 (CTO2) | 180.0 | 4.000 | 3 |
| 5 (NHL) | 6 (CTL1) | 7 (CTO1) | 15 (OHL) | 180.0 | 15.50 | 2 |
| 5 (NHL) | 6 (CTL1) | 7 (CTO1) | 15 (OHL) | 0.000 | 6.000 | 3 |
| 5 (NHL) | 6 (CTL1) | 7 (CTO1) | 8 (CTO1) | 180.0 | 5.500 | 2 |
| 5 (NHL) | 6 (CTL1) | 7 (CTO1) | 8 (CTO1) | 0.000 | 7.500 | 3 |
| 5 (NHL) | 6 (CTL1) | 13 (CTO2) | 14 (OHL) | 0.000 | 7.000 | 1 |
| 5 (NHL) | 6 (CTL1) | 13 (CTO2) | 14 (OHL) | 180.0 | 8.500 | 2 |
| 5 (NHL) | 6 (CTL1) | 13 (CTO2) | 14 (OHL) | 0.000 | 5.500 | 3 |
| 15 (OHL) | 7 (CTO1) | 8 (CTO1) | 16 (OHL) | 180.0 | 8.000 | 1 |
| 15 (OHL) | 7 (CTO1) | 8 (CTO1) | 16 (OHL) | 0.000 | 3.000 | 3 |
| 15 (OHL) | 7 (CTO1) | 8 (CTO1) | 9 (CTL2) | 0.000 | 8.000 | 1 |
| 15 (OHL) | 7 (CTO1) | 8 (CTO1) | 9 (CTL2) | 0.000 | 0.900 | 3 |
| 7 (CTO1) | 8 (CTO1) | 9 (CTL2) | 10 (CTL2) | 180.0 | 0.800 | 1 |
| 7 (CTO1) | 8 (CTO1) | 9 (CTL2) | 10 (CTL2) | 180.0 | 3.200 | 2 |
| 7 (CTO1) | 8 (CTO1) | 9 (CTL2) | 10 (CTL2) | 0.000 | 1.000 | 3 |
| 16 (OHL) | 8 (CTO1) | 9 (CTL2) | 10 (CTL2) | 0.000 | 0.000 | 3 |
| 22 (HAL2) | 8 (CTO1) | 9 (CTL2) | 10 (CTL2) | 0.000 | 0.000 | 3 |
| 22 (HAL2) | 8 (CTO1) | 9 (CTL2) | 23 (HAL2) | 0.000 | 0.000 | 3 |
| 7 (CTO1) | 8 (CTO1) | 16 (OHL) | 28 (HOL) | 0.000 | 0.000 | 3 |
| 9 (CTL2) | 8 (CTO1) | 16 (OHL) | 28 (HOL) | 0.000 | 0.000 | 3 |

TABLE 5

Modified CHARMM36 improper torsion parameters for ceramide NP.
Atom numbers correspond to the atom numbers in FIG. 1f and
the CHARMM36 atom types are given in parentheses.

| Atom 1 | Atom 2 | Atom 3 | Atom 4 | $\xi_0$ (deg) | k$\xi$ (kJ/mol/rad$^2$) |
|---|---|---|---|---|---|
| 5 (NHL) | 1 (C) | 6 (CTL1) | 19 (H) | 0.000 | 40.00 |
| 1 (C) | 2 (CTL2) | 5 (NHL) | 12 (O) | 0.000 | 40.00 |

TABLE 6

Modified CHARMM36 exclusion parameters for ceramide NP.
Atom numbers correspond to the atom numbers in FIG. 1f and
the CHARMM36 atom types are given in parentheses.
Non-bonded Interactions between atom 1 and
the listed exclusion atoms are ignored.

| Atom 1 | Exclusion atoms |
|---|---|
| 21 (HAL1) | 22 (HAL1) |
| 15 (OHL) | 28 (HOL) |
| 27 (HOL) | 16 (OHL), 28 (HOL) |
| 18 (HAL2) | 19 (H) |
| 12 (O) | 15 (OHL), 27 (HOL) |

In addition, atom coordinates of the membrane components in an outstretched conformation may be required for building the lipid matrix model starting structure. The molecules do not have to be in an energetically favorable conformation from the start.

To generate the stratum corneum lipid matrix model, the following steps may be performed:

1) Generation of an empty matrix with two layers. The size of the empty matrix may e.g. be 10×10 (X-times Y-dimension, with the Z-dimension perpendicular to the matrix), and the matrix may be filled with ceramides, cholesterol and free fatty acids according to their respective concentrations. Each layer of the matrix may be divided into two regions or parts, where one part (referred to as the ceramide fatty acid region) may contain the ceramide fatty acid moieties, free fatty acids and cholesterol, and the other part (referred to as the ceramide sphingoid region) may contain the ceramide sphingoid moieties and cholesterol. The next layer may be built in a similar way, with the ceramide fatty acid region interfacing with the ceramide fatty acid region in the first layer. An example of the filling of the matrix is illustrated in FIGS. 8a-d and FIGS. 9a-d. FIGS. 8 a-d illustrate top views of the matrix filled with ceramides, cholesterol, free fatty acids and water, respectively. FIGS. 9a-d illustrate corresponding side views of the matrix;

2) Generation of a periodic box around the system with a minimum distance to atoms that is large enough to avoid atoms colliding over the periodic box boundary, and 3) Addition of water to the system. The water may be placed close to the head group (0.3-0.5 nm) but preferably no closer than 0.06 nm to the periodic box edge.

MD simulations of the lipid matrix model may be run, using for example GROMACS (Pronk et al., 2013; Abraham et al., 2015), and may include the following steps:

1) Energy minimization with long-range interaction settings appropriate for the chosen force field. Simulations may for example be run using a steepest-descent integrator for 5000 steps and a tolerance of 10.0 kJ/mol/nm;

2) Equilibration starting with an NVT-ensemble followed by an NPT-ensemble, starting with restraints that may be lowered and thereafter removed in steps during the equilibration stages. Equilibration may proceed for at least 250 ns, and 3) A final step, referred to as production (also in the NPT-ensemble) may be run, during which e.g. the size of the system may be measured. This step may be run e.g. for an additional 100 ns.

To calculate the permeability of the lipid matrix model to a generic organic compound, the following steps may be performed:

1) Calculation of the hydration free energy (solvation free energy in water) of the compound;

2) Calculation of the solvation free energy of the compound in the lipid matrix (the free energy of a conformation that could be considered bound in the membrane) in the interface between the ceramide sphingoid chains;

3) Insertion of two copies of the compound/molecule in the equilibrated (e.g. after the 100 ns production phase) lipid matrix model, one in the interface between the ceramide sphingoid chains and one in the interface between the ceramide fatty acid chains. The copies of the compound/molecule may be inserted at random positions in the X/Y plane;

4) Equilibration of the system with the inserted copies of the compound/molecule for, e.g., 1 ns;

5) From the equilibrated system, run of two simulations pulling both copies of the compound/molecule in the same direction in positive and negative Z-direction, respectively (referred to as forward and reverse pulling);

6) Repetition of steps 3-5 to achieve enough total simulation time; and

7) Calculation of the potential of mean force (PMF, using the difference in free energy of the compound in the lipid matrix and the hydration free energy as a zero point) and local diffusion coefficient throughout the system (in the Z-direction), and, from that, calculation of the permeability of the stratum corneum lipid matrix to the compound/molecule. This may be done e.g. by a Python script using a weighted version of the Crooks fluctuation theorem (Crooks, 1999; Crooks, 2000; Kosztin et al, 2006; Forney et al., 2008; Chen, 2008; and Park and Schulten, 2004). The average, or Boltzmann weighted average, from e.g. 3 separate hydration free energy calculations as in 1) may be used when calculating the zero point for the PMF, or the insertion free energy. The average, or Boltzmann weighted average, from e.g. 4 to 6 separate solvation free energy calculations as in 2) may be used when calculating the zero point for the PMF.

Permeability may also be calculated in different ways, in addition to the above described non-equilibrium MD simulations, such as by umbrella sampling, analyzed using WHAM (Kumar, 1992) or MBAR (Shirts and Chodera, 2008), or the accelerated weight histogram (AWH) method (Lindahl et al., 2014).

If using umbrella sampling, the first step of may be to generate starting conformations over the reaction coordinate (e.g. along the normal of the lipid matrix), e.g. by pulling a permeant, using e.g. a moving umbrella potential, through at a constant rate and writing coordinates, used as starting positions in the next step, at regular intervals. In the next step a simulation may be started from each of the starting positions (outputs from the previous step) and an umbrella potential may be restraining the position of the permeant and the required force to keep it in place may be used to calculate the PMF and the local diffusion coefficient.

The AWH method (Lindahl et al., 2014) is an extended ensemble technique that applies an adaptive bias to explore a reaction coordinate (the positions of the permeant along the normal of the lipid matrix).

It is also envisaged that flux (J) may be used as an alternative measure of permeability, and given by $J=PC_{donor}$ where $C_{donor}$ is the concentration of the compound in the donor compartment and where P is the permeability coefficient. The concentration $C_{donor}$ may preferably be kept at, or close to, the solubility of the compound.

To simulate how a permeation modifying agent (PMA), or a combination of multiple such agents, affects the stratum corneum lipid matrix, the following steps may be performed:

1) Starting from the equilibrated lipid matrix system (e.g. the output structure after the 100 ns production phase), insertion of the wanted concentration of the PMA, e.g. 0.25-8 PMA molecules per ceramide molecule, and 2) Energy minimization and equilibration of the system, for example according to steps 1 to 3 as described above for running the MD simulations.

To calculate the permeability of the stratum corneum lipid matrix with a PMA to a generic organic compound/molecule, the steps 2 to 7 as described above for calculating the permeability of the stratum corneum lipid matrix to a generic organic compound/molecule may be followed, but with using the equilibrated system with the PMA inserted in the stratum corneum lipid matrix as input in step 3.

To suggest if a specific PMA may be used to modify the permeability of the stratum corneum lipid matrix to a specific compound, the PMF along the normal of the stacked lipid bi-layer, and the local diffusion coefficient of a permeant through the stratum corneum lipid matrix, may be calculated. The highest peak in the PMF may show where, across the lipid system, the permeation limiting part of the system is, making it possible to decide if a PMA that mainly interacts with the head group or the lipid tails would be most useful for modifying the permeability of the lipid matrix to the specific compound.

Example I

System Setup

A model of the stratum corneum lipid matrix was generated using a Python script. The system was generated as two layers, each of which was divided into a 10×10 matrix. The number of molecules of each type was calculated to get as close to the wanted distribution of ceramides (including ceramide EOS), free fatty acids and cholesterol as possible. If requested percentages of all molecules could not be exactly distributed, molecules were randomly added and/or removed to still be as close to the wanted ratio as possible. The molecules used for building the system were in a straight extended configuration (i.e., ceramides in a hair pin configuration were not used). Each point in the matrix, representing one of the lipid layers, could be filled by either a ceramides type molecule, expanding through the length of the whole layer of the matrix, or by a shorter molecule, fatty acid or cholesterol placed in the fatty acid chain region (closer to the membrane center of the built model) and/or a cholesterol in the sphingoid chain region. The next layer was filled by trying to match molecules with long chains in the fatty acid region with molecules with short chains to start from a system with as small gaps between molecules as possible. The distance between the two layers was set to avoid any collisions.

Water molecules were added by a script iteratively running the gmx solvate command, and after that, removing water molecules far from the head group and close to the periodic box edges. The iteration was run with increasing distance from the head group until the wanted number of water molecules had been added. If more water molecules were added than had been requested then random water molecules were removed.

Simulations

Models of the stratum corneum lipid matrix were evaluated using MD simulations, employing GROMACS and the CHARMM36 lipid force field. The parameters of ceramides NP were based on ceramides NS 24:0 and CHARMM36 atom types and bonded parameters and then optimized to reproduce quantum mechanical torsion scans and a published crystal structure of ceramides NP 24:18 (Dahlén and Pascher, 1979).

A Verlet cutoff scheme were used updating the pair list every 20 steps (automatically changed to 40 steps) with a cutoff distance of 1.2 nm. Van der Waals interactions were cutoff at 1.2 nm with a smooth force-switch from 1.0 nm to 1.2 nm. If possible, most simulations were run without a dispersion correction for energy and pressure to compensate for interactions outside the cutoff. Coulomb interactions were calculated using PME (Essmann et al., 1995) with a radius of 1.2 nm. Hydrogen bonds were constrained using the P-LINCS algorithm (Hess et al., 1997; Miyamoto et al., 1992). TIP3P (Jorgensen et al., 1983) parameters were used for water molecules.

Energy minimizations were run using a steepest descent integrator without constrained bonds for 5000 steps and a tolerance of 10.0 kJ/mol/nm. Heavy atoms were restrained to their original positions by a 100 kJ/mol/nm$^2$ force.

Equilibrations were run in five different stages, the first of which in the NVT ensemble and the following in the NPT ensemble with 1 bar semiisotropic pressure coupling using a Berendsen barostat (Berendsen et al, 1984) with a coupling constant of 5 ps and a compressibility of $4.5\ e^{-5}\ bar^{-1}$. The temperature was set to 303.15 K using a velocity rescaling thermostat (Bussi et al., 2007) with a coupling constant of 1 ps. In the first equilibration stage, the heavy atoms were still restrained to their starting positions by a 100 kJ/mol/nm$^2$ force. In the following stages, the restraints were not applied to the head group atoms (hetero atoms or carbon atoms binding hetero atoms) of the ceramides and the restraint forces on the ceramides were lowered to 10 and 2 kJ/mol/nm$^2$ in the third and fourth equilibration stages respectively, still keeping fatty acids and cholesterol restrained by a 100 kJ/mol/nm$^2$ force. In the last equilibration stage, no restraints were applied. The MD step size was chosen as 0.25 fs/step during the first equilibration stage of 5 ps. After that, the step size was chosen as 2 fs/step and the total equilibration time was approximately 270 ns, of which 250 ns were without restraints. The center of mass motion of the whole system was removed.

The production runs were the same as the last equilibration stage, except that a Parrinello-Rahman barostat (Parinello and Rahman, 1981) was employed with a coupling constant of 15 ps and the simulation length was 100 ns.

Simulations were performed for stratum corneum lipid matrices having various lipid compositions, various distributions of cholesterol over the bi-layer structure, various distributions of lipid chain lengths, various relative amounts of phytosphingosine- and sphingosine-based ceramides, and various finite numbers of water molecules associated with the lipid head groups. Herein, the different lipid matrices will be identified using the notation A/B/C/D/E/F, where A, B and C denotes the relative molar concentration, not including water, of ceramides (including both non O-acyl and O-acyl ceramides), cholesterol and free fatty acids respectively, where D denotes the relative amount of cholesterol located at/associated with the ceramide sphingoid chains, where E denotes the total molar O-acyl ceramide (e.g. ceramide EOS) concentration, not including water, and where F denotes the number of water molecules per ceramide. For example, a lipid matrix system identified with 33/33/33/75/5/1 denotes a system with an equal molar concentration (33%) of ceramides, cholesterol and free fatty acids, where 75% of the cholesterol is located at/associated with the ceramide sphingoid chains, where the total molar O-acyl ceramide (e.g. ceramide EOS) concentration, not including water, is 5% and where there is one water molecule per ceramide. One example of a lipid matrix system 33/33/33/75/5/1 is illustrated in FIGS. 8a-d and 9a-d, which show top views and side views of ceramides, cholesterol, free fatty acids and water, respectively before MD simulations.

Ceramide EOS was used as O-acyl ceramides, although it is envisaged that other O-acyl ceramides may also be used as previously disclosed herein.

Using the last frame from the above simulations, simulations of electron micrographs (EMs) were performed (Rullgård et al., 2011). Using a Python script, intensity curves were generated from the EM images where the intensity of each column in the image was recorded. A Gaussian filter with a standard deviation of 1.0 was applied to smooth the curves. The simulated EM images were then compared with experimental EM data achieved by using cryo-electron microscopy of vitreous sections (CEMOVIS) on samples of real human skin. For both the simulated EM images and the CEMOVIS data a defocus level of −1.2 µm were used.

Experimental CEMOVIS images were slightly distorted, due to curvatures in the structure, before calculating the intensity profile and the same script was used to first align each row of pixels to minimize the difference between its intensity profile and the average intensity profile of previously aligned rows.

A Python script was used to give a numerical value of the difference between two EM intensity curves, in order to have a measure of the similarity between a simulated EM image and the experimental cryo-EM image. Only the central periodic unit of the cryo-EM images was used as its image quality was higher than the edges of the image. The image was cropped by hand, based on a cryo-EM image, which had been straightened (i.e., aligned, see previous section). Intensities ranged from 0 (black in the image) to 255 (white in the image). A Gaussian filter (standard deviation 1.0) was used to smoothen both curves before comparing them. During the comparison, the intensity curves were allowed to roll (move in the x dimension), intensities were scaled (in the y dimension, with intensity value 127 as zero point) and the intensities were shifted (move in the y dimension) to reduce the difference between the curves as much as possible. The measured difference was the average absolute difference at all points in the intensity curves. Since the lower defocus levels yield images with higher resolution the results were weighted by factors 2, 1.5 and 1 for defocus levels −1, −2 and −3 µm, respectively, and the sum of the average absolute difference from the three curves are presented in the tables below.

Results

To compare the results of MD simulations using a model of the stratum corneum lipid matrix in accordance with the present disclosure, intensity curves for the various lipid matrix systems were compared with a corresponding intensity curve obtained from CEMOVIS. The results are shown in FIGS. 2-7, and in Tables 7-12 which show the various system compositions and calculated thicknesses/periodicities. The stratum corneum lipid matrix system, after MD simulation, is shown for 33/33/33/75/5/1 in FIGS. 10a-d, which illustrate side views of the organization of ceramides, cholesterol, free fatty acids and water respectively.

FIGS. 2a-g and Table 7 show intensity profiles, thicknesses/periodicities and automatic EM intensity profile comparison differences for systems having an equal relative molar concentration (33%) of ceramides, cholesterol and free fatty acids, with 75% of the cholesterol located at/associated with the ceramide sphingoid chains, with a total molar ceramide EOS concentration of 5%, and with varying numbers of water molecules per ceramide, i.e. 33/33/33/75/5/F with =0, 1, 2, 3, 4, 5, and 6. The simulation with 0 water molecules per ceramide were added for comparative purposes. Regarding the relative depths and heights of the valleys and peaks in the intensity profiles, it may be observed that especially the systems with F=1 (FIG. 2b) and with F=2 (FIG. 2c) reproduce approximately the profile of the CEMOVIS data well, although every system has a thickness/periodicity which corresponds well to experimental values of 10.5-11 nm obtained from CEMOVIS (Iwai, 2012). To obtain the automatic EM intensity profile comparison differences, sums of the average absolute difference from the EM intensity curve was weighted by factors 2, 1.5 and 1 at defocus levels −1, −2 and −3 µm. A low comparison difference means high similarity between the simulated EM image of the model lipid matrix system and the experimental cryo-EM image.

TABLE 7

Calculated thicknesses/periodicities for lipid matrices with varying numbers of water molecules per ceramide.

| Identification (A/B/C/D/E/F) | Thickness/periodicity (nm) | Automatic EM intensity profile comparison difference |
| --- | --- | --- |
| 33/33/33/75/5/0 | 10.5 | 29.3 |
| 33/33/33/75/5/1 | 10.6 | 28.3 |
| 33/33/33/75/5/2 | 10.5 | 31.2 |
| 33/33/33/75/5/3 | 10.8 | 37.2 |
| 33/33/33/75/5/4 | 10.8 | 38.5 |
| 33/33/33/75/5/5 | 10.8 | 39.8 |
| 33/33/33/75/5/6 | 10.8 | 40.9 |

FIGS. 3a-h and Table 8 show intensity profiles, thicknesses/periodicities and automatic EM intensity profile comparison differences for systems having an equal relative molar concentration (33%) of ceramides, cholesterol and free fatty acids, with a total molar ceramide EOS concentration of 5%, with one water molecule per ceramide, and with a varying amount of cholesterol located at/associated with the ceramide sphingoid chains, i.e. 33/33/33/D/5/1 where D=100, 90, 85, 80, 75, 70, 65 and 60. Regarding the thickness/periodicity, it may be observed in Table 8 that a maximum thickness/periodicity is achieved for D=70, 75 or 80 and also that the corresponding (FIG. 3f, e or d) intensity profiles reproduce approximately the profile of the CEMOVIS data well.

TABLE 8

Calculated thicknesses/periodicities for lipid matrices with varying amount of cholesterol located at/associated with ceramide sphingoid chains.

| Identification (A/B/C/D/E/F) | Thickness/periodicity (nm) | Automatic EM intensity profile comparison difference |
|---|---|---|
| 33/33/33/100/5/1 | 9.2 | 44.2 |
| 33/33/33/90/5/1 | 9.7 | 41.5 |
| 33/33/33/85/5/1 | 9.9 | 35.8 |
| 33/33/33/80/5/1 | 10.3 | 31.2 |
| 33/33/33/75/5/1 | 10.5 | 28.3 |
| 33/33/33/70/5/1 | 10.5 | 28.8 |
| 33/33/33/65/5/1 | 10.2 | 29.2 |
| 33/33/33/60/5/1 | 10.0 | 33.2 |

Figure 4A:
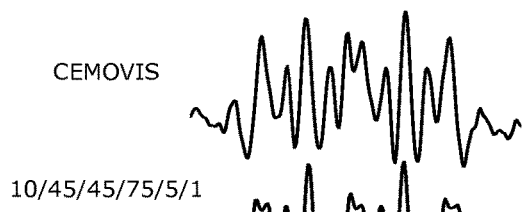
FIGS. 4a-h illustrate experimental CEMOVIS intensity profiles and intensity profiles calculated in accordance with a method of the present disclosure, using a model with varying relative concentration of ceramides.
Figure 4B:
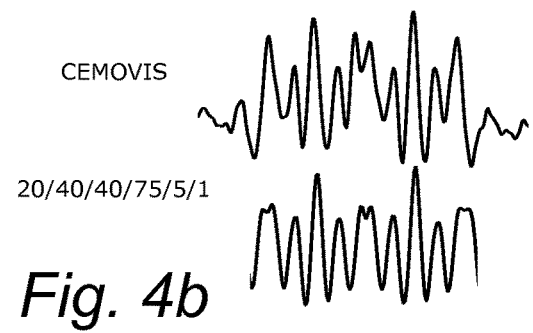
Figure 4C:
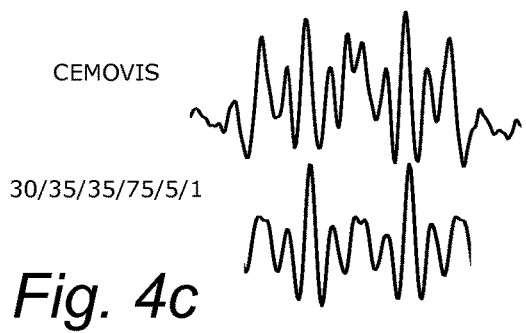
Figure 4D:
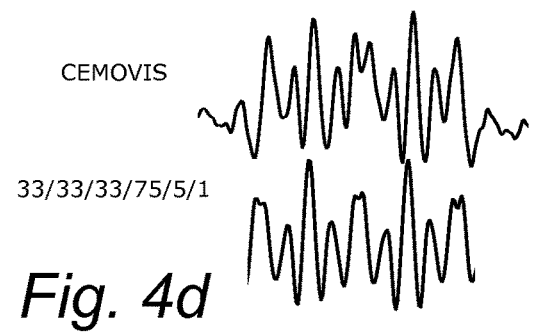
Figure 4E:
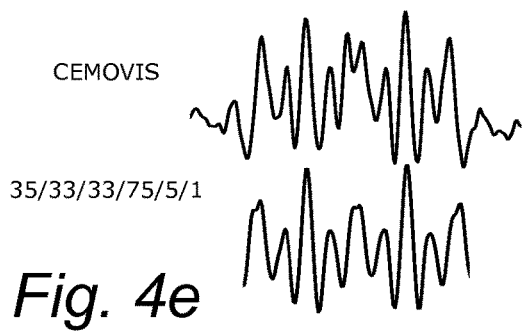
Figure 4F:
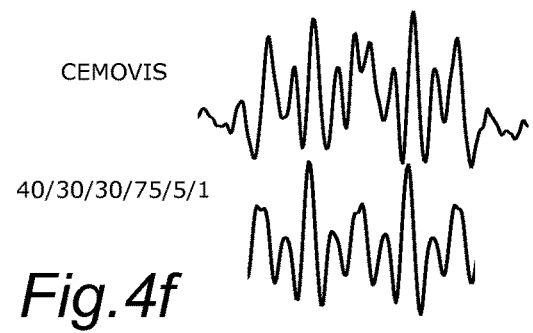
Figure 4G:
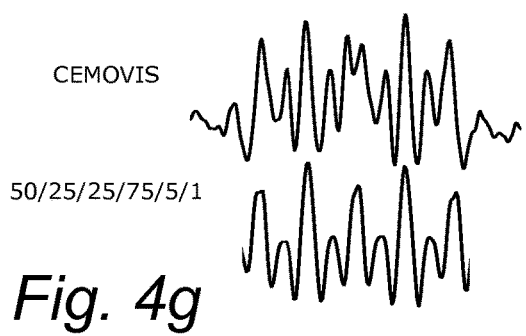
Figure 4H:
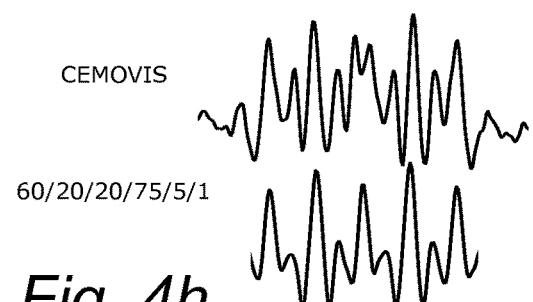
Figure 5A:
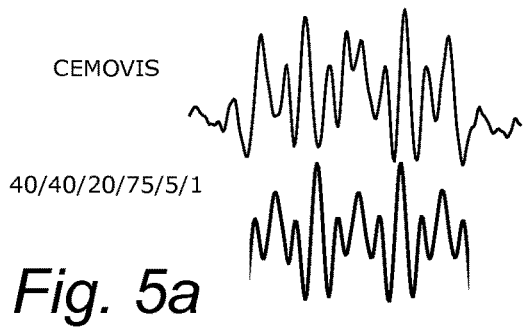
FIGS. 5a-f illustrate experimental CEMOVIS intensity profiles and intensity profiles calculated in accordance with a method of the present disclosure, using a model with varying relative concentration of free fatty acid.
Figure 5B:
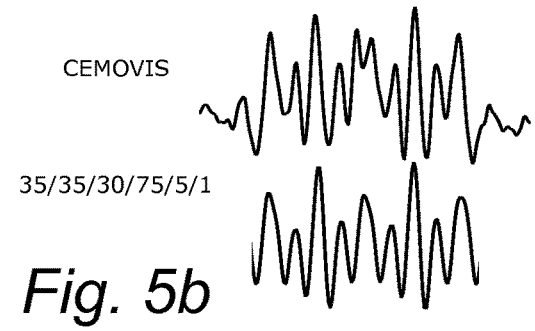
Figure 5C:
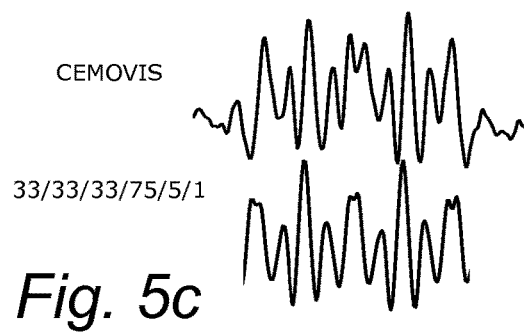
Figure 5D:
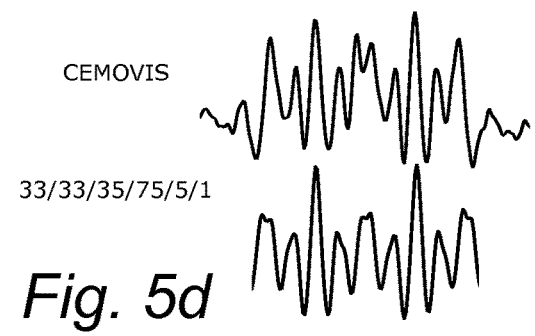
Figure 5E:
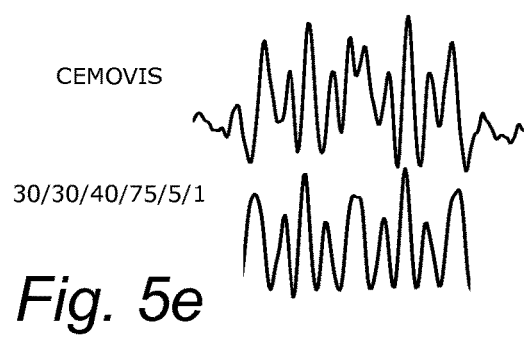
Figure 5F:
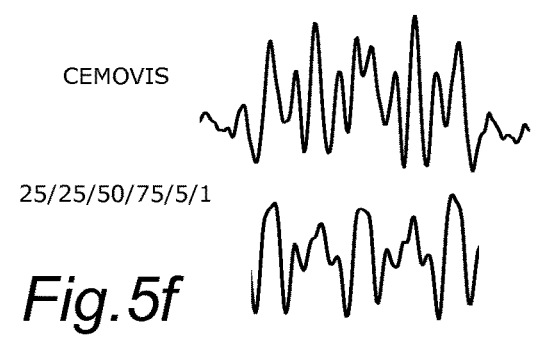
Figure 6A:
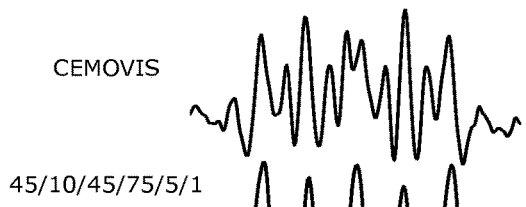
FIGS. 6a-g illustrate experimental CEMOVIS intensity profiles and intensity profiles calculated in accordance with a method of the present disclosure, using a model with varying relative concentration of cholesterol.
Figure 6B:
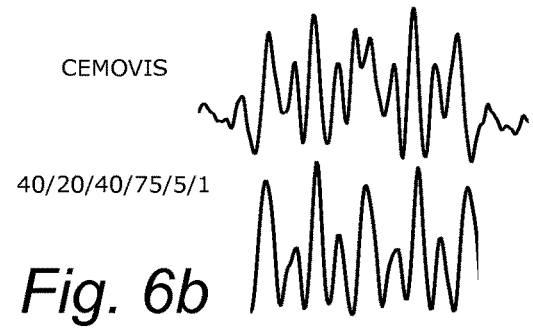
Figure 6C:
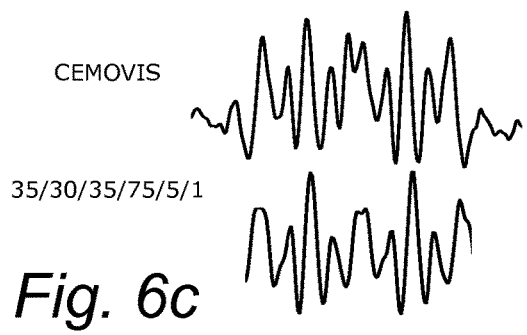
Figure 6D:
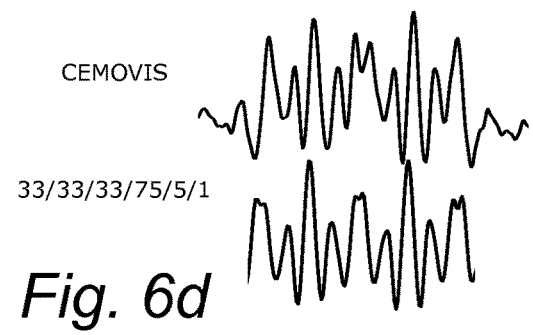
Figure 6E:
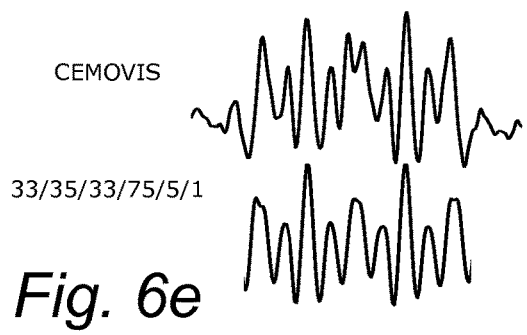
Figure 6F:
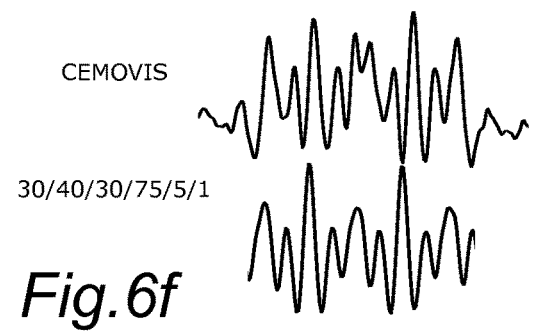
Figure 6G:
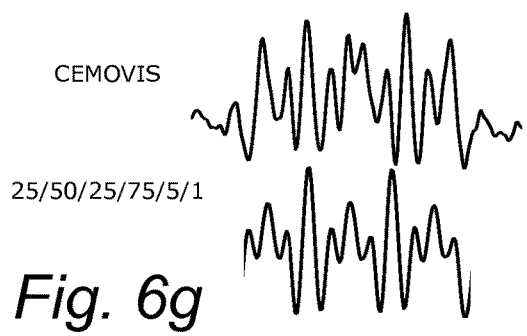
Figure 7A:
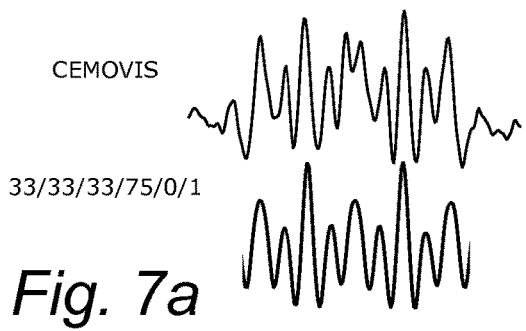
FIGS. 7a-g illustrate experimental CEMOVIS intensity profiles and intensity profiles calculated in accordance with a method of the present disclosure, using a model with varying total concentration of ceramide EOS.
Figure 7B:
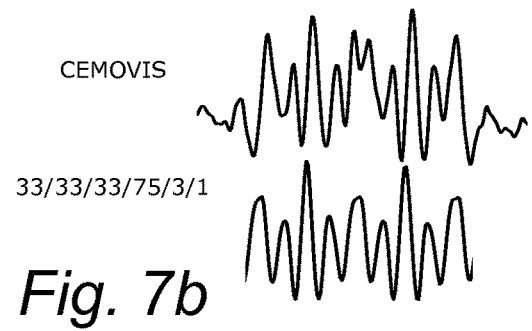
Figure 7C:
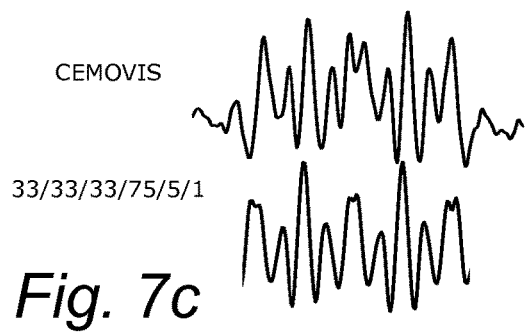
Figure 7D:
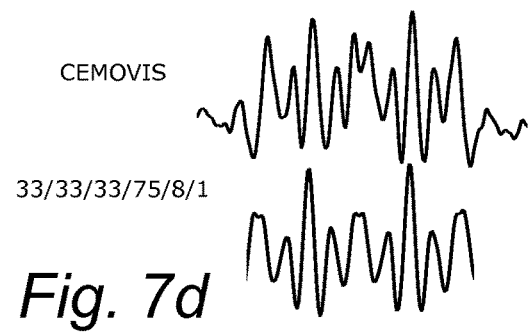
Figure 7E:
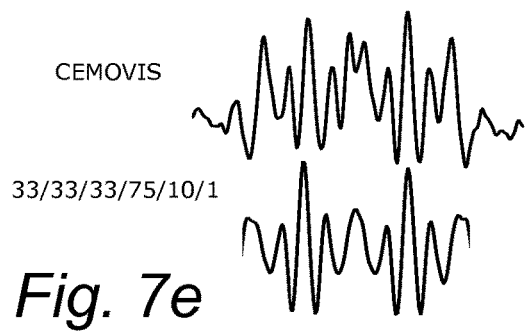
Figure 7F:
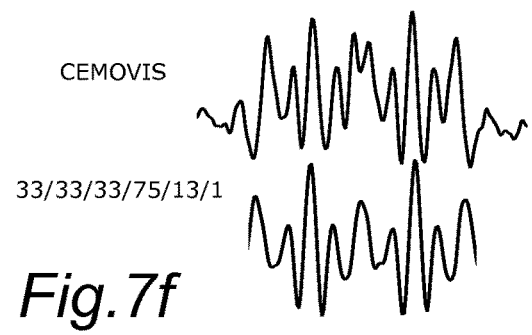
Figure 7G:
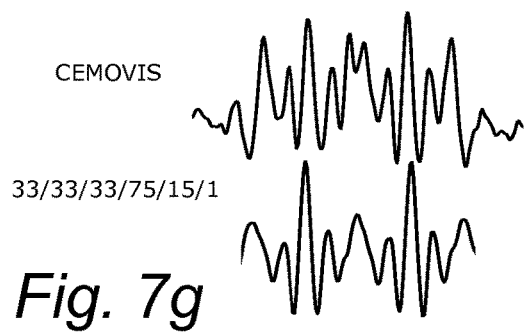

FIG. 4a- and Table 9 show intensity profiles, thicknesses/periodicities and automatic EM intensity profile comparison differences for systems having an equal relative molar concentration of cholesterol and free fatty acids, with 75% of the cholesterol located at/associated with the ceramide sphingoid chains, with a total molar ceramide EOS concentration of 5%, with one water molecule per ceramide, and with a varying relative molar concentration of ceramides, i.e. A/B/C/75/5/1 where A=10, 20, 30, 33, 35, 40, 50 and 60, and B=C=50-0.5A.

Regarding the thickness/periodicity, it may be observed from Table 9 that the greatest thickness is achieved for A=30, 33, 35, but also that e.g. A=25, A=40 and A=45 are relevant. The same applies regarding the depths and heights of the valleys and peaks of the intensity profiles, i.e. in FIGS. 4c-f.

TABLE 9

Calculated thicknesses/periodicities for lipid matrices with varying relative molar concentration of ceramides.

| Identification (A/B/C/D/E/F) | Thickness/periodicity (nm) | Automatic EM intensity profile comparison difference |
|---|---|---|
| 10/45/45/75/5/1 | 10.1 | 35.8 |
| 20/40/40/75/5/1 | 10.4 | 29.6 |
| 30/35/35/75/5/1 | 10.5 | 29.6 |
| 33/33/33/75/5/1 | 10.6 | 28.3 |
| 35/33/33/75/5/1 | 10.6 | 32.4 |
| 40/30/30/75/5/1 | 10.4 | 30.9 |
| 50/25/25/75/5/1 | 10.4 | 36.8 |
| 60/20/20/75/5/1 | 9.9 | 41.5 |

FIGS. 5a-f and Table 10 show intensity profiles, thicknesses/periodicities and automatic EM intensity profile comparison differences for systems having an equal relative molar concentration of ceramides and cholesterol, with 75% of the cholesterol located at/associated with the ceramide sphingoid chains, with a total molar ceramide EOS concentration of 5%, with one water molecule per ceramide, and with a varying relative molar concentration of free fatty acids, i.e. A/B/C/75/5/1 where C=20, 30, 33, 35, 40 and 50 and A=B=50-0.5C.

TABLE 10

Calculated thicknesses/periodicities for lipid matrices with varying relative molar concentration of free fatty acids.

| Identification (A/B/C/D/E/F) | Thickness/periodicity (nm) | Automatic EM intensity profile comparison difference |
|---|---|---|
| 40/40/20/75/5/1 | 9.3 | 48.9 |
| 35/35/30/75/5/1 | 10.1 | 33.5 |
| 33/33/33/75/5/1 | 10.6 | 28.3 |
| 33/33/35/75/5/1 | 10.6 | 33.0 |
| 30/30/40/75/5/1 | 10.6 | 35.4 |
| 25/25/50/75/5/1 | 9.7 | 38.0 |

FIGS. 6a-g and Table 11 show intensity profiles, thicknesses/periodicities and automatic EM intensity profile comparison differences for systems having an equal relative molar concentration of ceramides and free fatty acids, with 75% of the cholesterol located at/associated with the ceramide sphingoid chains, with a total molar ceramide EOS concentration of 5%, with one water molecule per ceramide, and with a varying relative molar concentration of cholesterol, i.e. A/B/C/75/5/1 where B=10, 20, 30, 33, 35, 40, 50 and A=C=50-0.5B. Regarding the thickness/periodicity, it may be observed from Table 11 that at least B=20, 30, 33 and 35 corresponds to the greatest thickness and that the corresponding intensity profiles (FIGS. 6b-e) reproduce approximately the intensity profile from CEMOVIS well.

TABLE 11

Calculated thicknesses/periodicities for lipid matrices with varying relative molar concentration of cholesterol.

| Identification (A/B/C/D/E/F) | Thickness/periodicity (nm) | Automatic EM intensity profile comparison difference |
|---|---|---|
| 45/10/45/75/5/1 | 10.1 | 42.9 |
| 40/20/40/75/5/1 | 10.7 | 37.0 |
| 35/30/35/75/5/1 | 10.8 | 35.3 |
| 33/33/33/75/5/1 | 10.6 | 28.3 |
| 33/35/33/75/5/1 | 10.4 | 29.4 |
| 30/40/30/75/5/1 | 9.8 | 33.7 |
| 25/50/25/75/5/1 | 8.8 | 43.2 |

FIGS. 7a-g and Table 12 show intensity profiles, thicknesses/periodicities and automatic EM intensity profile comparison differences for systems having an equal relative molar concentration (33%) of ceramides, cholesterol and free fatty acids, with 75% of the cholesterol located at/associated with the ceramide sphingoid chains, with one water molecule per ceramide, and with a varying total molar concentration of O-acyl ceramide (here ceramide EOS), i.e. 33/33/33/75/E/1 where E=0, 3, 5, 8, 10, 13, and 15. It may be observed from Table 12 and FIGS. 7b-e that especially E=3, 5, 8 and 10 corresponds to a thickness/periodicity comparable to experimental values and that the corresponding intensity curves reproduce approximately the CEMOVIS data well.

TABLE 12

Calculated thicknesses/periodicities for lipid matrices with varying total molar concentration of O-acyl ceramide (ceramide EOS).

| Identification (A/B/C/D/E/F) | Thickness/periodicity (nm) | Automatic EM intensity profile comparison difference |
|---|---|---|
| 33/33/33/75/0/1 | 10.0 | 34.3 |
| 33/33/33/75/3/1 | 10.4 | 29.5 |
| 33/33/33/75/5/1 | 10.6 | 28.3 |

TABLE 12-continued

Calculated thicknesses/periodicities for lipid matrices with varying total molar concentration of O-acyl ceramide (ceramide EOS).

| Identification (A/B/C/D/E/F) | Thickness/periodicity (nm) | Automatic EM intensity profile comparison difference |
|---|---|---|
| 33/33/33/75/8/1 | 10.7 | 35.2 |
| 33/33/33/75/10/1 | 11.1 | 39.0 |
| 33/33/33/75/13/1 | 11.2 | 38.6 |
| 33/33/33/75/15/1 | 11.2 | 41.0 |

Example II

System Setup and Simulations

In this example, the system was setup in accordance with Example I, but with a single lipid matrix system corresponding to 33/33/33/75/5/1.

The permeabilities of the stratum corneum lipid matrix to benzene, codeine, DMSO, ethanol, naproxen, nicotine, testosterone and water were calculated using non-equilibrium forward-reverse simulations, based on the Crooks fluctuation theorem and with the work weighted using the Brownian Dynamics Fluctuation Dissipation Theorem (BD-FDT) (Chen, 2008).

Except for water, for which TIP3P parameters were used, CgenFF (Vanommeslaeghe et al., 2010) parameters were generated using STaGE, using Open Babel and MATCH to generate GROMACS topologies.

The simulations were run using Copernicus (Pronk et al., 2015) to setup the systems and distribute the simulations to multiple workers. Two molecules were inserted in the equilibrated membrane system at random lateral positions. The first molecule was inserted in the interface between the ceramides sphingoid chain moiety, and the other molecule was inserted between the ceramides fatty acid moiety. The molecules were inserted using the gmx insert-molecules command with scale=0.275 and trying to insert it within a distance of 2.0 nm from the randomly selected position in the x and y dimensions and 0.1 nm in the z dimension. If it was not possible to fit the molecule in 30 000 attempts, a new random position was chosen. Thereafter, the molecules were grown into the system by slowly turning on the interactions with their surroundings using the decoupling options in GROMACS, starting at lambda=0.75 and linearly going to lambda=0, where lambda=1 means no Van der Waals or Coulomb interactions with the rest of the system.

After additional equilibration (1 ns), the molecules were pulled in the forward and reverse directions (increasing and decreasing z coordinates) from the same starting position. A pulling speed of 0.2 nm/ns was used to force the molecule to move through the system. The umbrella potential was 15000 kJ/mol/nm$^2$ for water, ethanol, dmso and benzene and 40000 kJ/mol/nm$^2$ for codeine, naproxen, nicotine and testosterone. The simulations were performed using a leap-frog stochastic dynamics integrator at a temperature of 303.15 K. The pressure was kept using a semiisotropic Parrinello-Rahman barostat, now with 0 compressibility in the z direction.

Each simulation was performed long enough to pull both molecules completely through the system and the simulations were repeated, at random starting positions, to give a total simulation time of 2-5 μs (20-50 pulls in the forward and reverse direction).

The reaction coordinate was divided into 200 bins to group the performed work throughout the system. The zero point of the PMF, the insertion free energy, for transport through the membrane, was set by calculating the free energy difference between the molecules being solvated in water, in a dodecahedron shaped periodic box with at least 1.4 nm between the solute and the closest box edge, compared to being embedded in the membrane in the interface between the sphingoid side chains. These calculations were performed using the free energy module of Copernicus, which runs GROMACS MD simulations, in which interactions between a molecule and its surroundings are decoupled and the free energy of decoupling is calculated using the Bennett Acceptance Ratio (BAR) method (Bennett, 1976). Copernicus automatically optimizes the lambda point distributions for decoupling of the molecule (Pronk et al., 2015; Lundborg and Lindahl, 2014) and runs the decoupling simulations in iterations (in steps of 3 ns) until the desired statistical error is reached. To ensure transferability of the free energy results in water compared to the bound state all free energy calculations were run without long-range dispersion corrections (as long-range dispersion corrections are not recommended in CHARMM36 when simulated lipid bilayers). Three calculations were run to calculate the free energy of the solvated state, running until the estimated statistical error was no more than 0.25 kJ/mol, and six calculations were run to calculate the free energy of the bound state, requiring a statistical error of no more than 0.50 kJ/mol. The Boltzmann weighted averages of the results from the calculations of the free energy of the solvated state and the results from the calculations of the free energy of the bound state, respectively, was used to calculate the energy difference between the two states, which in turn was used as zero point for the PMF in the next step.

The error of the PMF was approximated by statistical bootstrapping of the work in each bin, at p=0.32 and by including the error of the binding free energy, by standard error propagation. The resistivity profiles were made symmetric about z=0 (center of the membrane) to enhance the sampling. When making the resistivity profiles symmetric, the PMF was allowed to roll up to ⅛ of the region to find the minimum difference between the two halves, to avoid large differences in case the PMF was not perfectly centered.

The dissipative work, just like if calculating diffusion from integrated autocorrelation times as is commonly done in umbrella sampling, can have a very rough profile in case of limited sampling. Therefore, it was smoothened by applying a Hanning-window with a window length of 11, with 200 points along the curve.

Results

Experimental (log $K_{P303K}$) and calculated permeabilities (log $K_P$) in cm/h for benzene, codeine, DMSO, ethanol naproxen, nicotine, testosterone and water in cm/h are given in Table 13. The experimental permeability values shown were obtained from in vitro diffusion cells. This means that these permeability coefficients are expected to have increased by 10-fold (1 log unit) from hydration and potentially further from e.g. freezing damages, compared to native state. The calculated permeabilities are presented after 2, 3, 4 and 5 μs (20-50 pulls in each direction). The experimental permeabilities were acquired from literature at temperatures ranging from 25–37° C. To account for the difference in temperature, a correction (Abraham and Martins, 2004) were applied to correct the experimental values according to:

$$\log K_{P303K} = \log K_{Pexp} + 0.04(303 - T_{exp}),$$

where log $K_{P303K}$ is the permeability coefficient at 303 K, the temperature at which the MD simulations were run, and where log $K_{Pexp}$ is the experimental permeability coefficient at the temperature $T_{exp}$ at which the experiment was performed.

TABLE 13

Experimental and calculated permeabilities for different compounds. The presented uncertainties correspond to one standard error.

| Compound | log $K_{p303K}$ (cm/h) | log $K_p$ after 2 µs (cm/h) | log $K_p$ after 3 µs (cm/h) | log $K_p$ after 4 µs (cm/h) | log $K_p$ after 5 µs (cm/h) |
|---|---|---|---|---|---|
| Benzene | −0.8 | −2.1 ± 0.3 | −1.7 ± 0.2 | −1.4 ± 0.2 | −1.0 ± 0.2 |
| Codeine | −4.6 | −6.8 ± 0.4 | −6.4 ± 0.4 | −5.9 ± 0.3 | −6.4 ± 0.3 |
| DMSO | −3.1 | −4.1 ± 0.2 | −4.8 ± 0.2 | −4.5 ± 0.2 | −4.2 ± 0.2 |
| Ethanol | −2.8 | −2.3 ± 0.2 | −2.7 ± 0.2 | −2.9 ± 0.2 | −2.7 ± 0.2 |
| Naproxen | −3.0 | −3.2 ± 0.3 | −3.9 ± 0.2 | −4.0 ± 0.2 | −4.1 ± 0.2 |
| Nicotine | −1.8 | −2.5 ± 0.3 | −2.3 ± 0.3 | −2.5 ± 0.2 | −2.1 ± 0.2 |
| Testosterone | −2.7 | −6.3 ± 0.4 | −6.2 ± 0.3 | −5.8 ± 0.3 | −6.1 ± 0.2 |
| Water | −2.9 | −4.5 ± 0.2 | −4.5 ± 0.2 | −4.6 ± 0.1 | −4.7 ± 0.1 |
| Mean diff. | | −1.27 | −1.34 | −1.24 | −1.21 |
| Mean abs. Diff. | | 1.40 | 1.39 | 1.24 | 1.24 |
| Mean sq. diff. | | 3.00 | 2.85 | 2.26 | 2.60 |

If experimental permeabilities were found in multiple sources, the average permeability was calculated and used. The experimental values used together with references are given in Table 14.

TABLE 14

Experimental and adjusted experimental permeabilities for different compounds.

| Compound | log $K_{Pexp}$ | $T_{exp}$ (° C.) | Reference |
|---|---|---|---|
| Benzene | −0.80 | 25 | Mitragotri et al., 1995 |
| | −0.95 | 31 | Blank and McAuliffe, 1985 |
| Codeine | −4.6 | 37 | Roy and Flynn, 1989 |
| DMSO | −3.1 | n/a | Daugherty, 1997 |
| Ethanol | −3.00 | 25 | Scheuplein, 1965 |
| | −3.10 | 25 | Scheuplein and Blank, 1973 |
| Naproxen | −2.54 | 37 | Degim et al., 1998 |
| | −3.40 | 25 | Barratt, 1995 |
| Nicotine | −2.48 | 37 | Degim et al., 1998 |
| | −1.71 | 25 | Barratt, 1995 |
| Testosterone | −2.70 | 25 | Mitragorti et al., 1995 |
| | −3.40 | 26 | Scheuplein et al., 1969 |
| Water | −3.00 | 25 | Scheuplein, 1965 |
| | −3.30 | 25 | Scheuplein and Blank, 1973 |

It may be observed from Table 13 that the permeability values calculated, using the method of calculating the permeability of the stratum corneum lipid matrix to different compounds in accordance with the present disclosure, are lower than permeability coefficients found in literature. This is to be expected since in vitro experiments using diffusion cells show a higher permeability due to excessive hydration of the skin patch (Idson, 1983 and van der Merwe and Ackermann, 1987). As shown above in e.g. Table 13 and Table 14, the experimental values are approximately −2.9 at 300 K and −2.8 at 310 K. Using the method presented herein, the calculated log $K_P$ permeability of the stratum corneum lipid matrix to water is −4.9 at 300 K, −4.7 at 303 K, and −4.5 at 310 K. Permeability values calculated using the method as disclosed herein are similar to those calculated in a study (Das et al., 2009), which calculated the log $K_P$ permeability (in cm/h) of the stratum corneum lipid matrix to water to −4.9 at 300 K while a second study (Gupta et al., 2016) calculated it to −0.59 at 310 K. Importantly, recalculating the permeability coefficient (log $K_P$) from the published figures of Das et al., 2009 results in approximately log $K_P$−1.4 cm/h indicating that the value given in Das et al. is due to a calculation error. Both these studies employed simpler, regarding ceramide and fatty acid heterogeneity, model systems with ceramides in hairpin configuration and the bilayer system surrounded by water. No previous permeability coefficient calculations have been made on atomic systems of stacked bilayer system with ceramides in splayed configuration.

In the second other study (Gupta et al, 2016), permeabilities to 11 compounds, including some of the ones presented herein, were calculated. The average absolute difference between the calculated and the experimental log $K_P$ values was found to be 2.9 (corresponding to a factor 800 average difference in permeability), while the average square difference in log $K_P$ was determined to be 12.8. In Gupta et al., all permeants, except for urea, had a calculated permeability that was too high compared to experimental permeabilities, which is not consistent with the observation that in vitro data already overestimates the permeability.

Using the method for calculating the permeability of the stratum corneum lipid matrix to the compounds presented e.g. in Table 13, it may be observed the average absolute difference between the calculated and experimental log $K_P$ values is 1.24 (a factor 17 average difference in permeability) and that the average square difference in log $K_P$ is 2.60.

Example III

System Setup and Simulations

In this example, the system was setup in accordance with Example I, but with a single lipid matrix system corresponding to 33/33/33/75/5/1. In addition, different examples of permeability enhancing agents (PMAs) were inserted into the system, such as azone, DMSO, oleic acid, stearic acid and water. The PMAs were inserted one by one, and simulations were performed for one inserted PMA at a time at a concentration of 9 wt %.

Starting from the production output from MD simulations as in Example I, a PMA was inserted into the system at different concentrations using the gmx insert-molecules command in GROMACS with 1000 tries before giving up and scaling Van der Waals radii of the molecules by 0.40. If the requested number of molecules could not be inserted the scaling factor was reduced in steps of 0.05 until the requested number of molecules could be inserted. The -allpairs option was also used to avoid memory leaks.

After completing the insertion of a PMA, the system with the PMA was minimized with respect to energy, equilibrated and production stages were run. The production stages were the same as in the previous example, but with the exception that the last equilibration stage, without restraints, was divided into three parts: 50 ns at 303.15 K, 150 ns at 318.15 K and 50 ns at 303.15 K. The reason for this temperature increase was to speed up the equilibration of the system. Permeability and PMF calculations were performed as described earlier.

Results

The effect of some PMAs on the stratum corneum lipid matrix system dimensions are shown in Table 15. The effect on the system thickness (periodicity), the surface area of the system and the lateral diffusion of ceramide headgroup atom C1 of the sphingoid side chain are specified. For water, the number of added water molecules (and their concentration in the system) is in addition to the water molecules already present in the head group region. The organization of some PMAs within the lipid matrix structure/system may be seen in FIGS. 11 a-e, which show side views of the organization of azone, DMSO, oleic acid, stearic acid and water, respectively.

TABLE 15

Calculated effect of some PMAs (concentration 9 wt %) on the stratum corneum lipid matrix system dimensions.

| PMA | Number per ceramide | Periodicity (nm) | System area (nm$^2$) | $D_{CIS}$ (1e-5 cm$^2$/s) |
|---|---|---|---|---|
| None | | 10.6 | 21.9 | 6.3e-5 ± 7.5e-5 |
| Azone | 0.5 | 10.7 | 23.8 | 1.1e-4 ± 3.6e-5 |
| DMSO | 2 | 10.9 | 23.2 | 2.8e-5 ± 5.0e-5 |
| Oleic acid | 0.5 | 10.6 | 24.2 | 3.9e-5 ± 1.9e-4 |
| Water | 8 | 11.7 | 21.8 | 7.5e-4 ± 9.4e-5 |

For example, the polar groups of azone and oleic acid were mainly associated with the ceramide head group region, and with non-polar tails generally aligned with the ceramide chains and favoring the longer fatty acid region. DMSO may be seen to form pores through the lipid matrix, which may help to explain its penetration enhancing properties. This is, in essence, the same as if lipids had been extracted from the lipid matrix and replaced by DMSO. Water molecules may be seen to associate with the head group region, and also in the interfaces between the non-polar lipid chains. This may improve the general solubility of hydrophilic molecules in the lipid matrix and may enhance penetration. A method in accordance with the present disclosure may therefore advantageously allow for detailed predictions, such as if said PMA forms pores in the lipid matrix, forms vesicles or distorts the lipid chain packing in general.

The effect of some PMAs on the permeability of the stratum corneum lipid matrix system to some compounds are shown in Table 16. From the table, it may be inferred that both azone and water improve the permeability of the system to all of codeine, nicotine, testosterone and water. From Table 16 it can be seen that adding 9 wt % water as permeation enhancer, to a lipid matrix system corresponding to 33/33/33/75/5/1, increases the permeability to a value that is higher than the permeability from in vitro diffusion cell experiments. This indicates that the increased hydration in the diffusion cell lipid membrane is not quite as high as 9 wt %.

TABLE 16

Calculated permeabilities for different compounds (columns) and PMAs (rows). The presented uncertainties correspond to one standard error.

| PMA | Codeine log $K_P$ (cm/h) | Nicotine log $K_P$ (cm/h) | Testosterone log $K_P$ (cm/h) | Water log $K_P$ (cm/h) |
|---|---|---|---|---|
| Azone 9 wt % | −2.8 ± 0.4 | −1.2 ± 0.3 | 0.2 ± 0.3 | −2.4 ± 0.2 |
| Oleic acid 9 wt % | −1.4 ± 0.4 | −0.2 ± 0.3 | −1.1 ± 0.3 | −2.9 ± 0.2 |
| Stearic acid 9 wt % | −5.1 ± 0.3 | −1.1 ± 0.3 | −4.0 ± 0.4 | −3.7 ± 0.2 |
| Water 5 wt % | −3.7 ± 0.2 | −0.6 ± 0.1 | −4.5 ± 0.2 | −3.8 ± 0.1 |
| Water 9 wt % | −2.7 ± 0.3 | −0.2 ± 0.2 | −1.5 ± 0.3 | −2.2 ± 0.1 |
| None | −6.3 ± 0.4 | −2.3 ± 0.3 | −6.2 ± 0.3 | −4.5 ± 0.1 |
| Experimental | −4.6 | −1.8 | −2.7 | −2.9 |

Example IV

System Setup and Simulations

Atomistic models of previously published models (Swartzendruber et al., 1989; Bouwstra et al., 2001; Hill and Wertz, 2003; McIntosh, 2003; Schröter et al., 2009; Iwai et al., 2012; and Mojumdar et al., 2016) were created by building a representative building block (2 building blocks for the system proposed by Mojumdar et al., 2016) of molecules arranged as proposed in the original publications. The building blocks were repeated to make a periodic box of approximately 10×10×2 molecules. When repeating the building blocks they were shifted and mirrored to ensure that the generated starting structures were symmetric, but disordered.

For each system MD simulation equilibration and production runs were performed as described in Example I.

Calculations of the permeability to water were done according to Example II. The presented permeability coefficients are from a total simulation time of 3 µs (30 pulls in each direction).

Results

The calculated permeability coefficients are presented in Table 17. The calculated permeability coefficients using previous proposed models, except for using the model proposed by Iwai et al., 2012, are significantly higher than the experimental value (log $K_P$ approximately −2.9 cm/h). The Iwai model consists of only splayed ceramide NP C24, free fatty acid C24 and cholesterol, with all cholesterol associated with the ceramide sphingoid moiety. Permeability coefficients calculated from a realistic model are expected to be lower than those obtained from in vitro experiments using diffusion cells, due to the high levels of hydration (Idson, 1983 and van der Merwe and Ackermann, 1987). The permeability coefficients obtained according to the present disclosure are indeed lower than the experimentally obtained coefficients.

TABLE 17

Calculated permeability coefficients to water of previously proposed models as found in the art. The presented uncertainties correspond to one standard error.

| Reference | log $K_{P_{calc}}$ (cm/h) |
|---|---|
| Swartzendruber et al., 1989 | −0.7 ± 0.2 |
| Bouwstra et al., 2001 | 3.0 ± 0.2 |
| Hill and Wertz, 2003 | 0.7 ± 0.3 |
| McIntosh, 2003 | −0.3 ± 0.2 |
| Schröter et al., 2009 | −0.5 ± 0.3 |
| Iwai et al., 2012 | −3.8 ± 0.2 |
| Mojumdar et al., 2016 | −1.0 ± 0.2 |

Example V

System Setup and Simulations

Atomistic models of lipid matrix systems of the composition described in this disclosure, as well as a number of comparative example systems for comparison, were generated as in Example I. In general the systems are described according to the notation A/B/C/D/E/F; where A, B and C denotes the relative molar concentration, not including water, of ceramides (including both non O-acyl and O-acyl ceramides), cholesterol and free fatty acids respectively; where D denotes the relative amount of cholesterol located at/associated with the ceramide sphingoid chains; where E denotes the total molar O-acyl ceramide (e.g. ceramide EOS) concentration, not including water; and where F denotes the number of water molecules per ceramide.

However, there are a few special exceptions. The systems 33-hairpin/33/33 stacked bilayer (no water) and 33-hairpin/

33/33 bilayer (with water) only consisted of ceramide NP C24, free fatty acid C24 and cholesterol. The ceramides were all arranged in the hairpin configuration. One was ordered as a stacked bilayer without water, whereas the other had approximately 5 nm of water between the lipid bilayers. The system with water is similar to what is often used when calculating water permeability through the lipid matrix using MD simulations (Das et al., 2009; Gupta et al., 2016). The 33-np/33/33/75/5/1 and 33-ns/33/33/75/5/1 systems the non-acyl ceramides were only ceramide NP or ceramide NS. In the 33-C20-50/33/33/75/5/1 system 50% of the ceramide have a sphingoid chain of length of 18C and 50% had a sphingoid chain of length 20C. In the other systems only sphingoid chain length 20C was used. The 33/33-CHOL-SULF-10/33/80/5/1 system had 10% of the cholesterol replaced by cholesterol sulfate and the 33/33/33-charged-FFA-10/80/5/1 system had 10% of the free fatty acids replaced by charged free fatty acid (deprotonated). The system 33/33/33-noXFFA30/75/5/1 had 2.3% (of free fatty acids) free fatty acid of chain length C30, compared to 15.9% in the 33/33/33/75/5/1 system. The 33/33/33/100/0/0 is similar to what was proposed by Iwai et al., 2012, but with the ceramide and free fatty acid chain length distribution, as well as ceramide NS/NP mixture, as described in the Examples summary above.

For each system MD simulation equilibration and production runs were performed as described in Example I.

Calculations of the permeability to water were done according to Example II. The presented permeability coefficients are from a total simulation time of 3 µs (30 pulls in each direction).
Results The results from the permeability calculations are presented in Table 18. It can be observed that the hairpin models do not reproduce the experimental data, whereas e.g. 33/33/33/75/5/1 result in a permeability coefficient that is very close to experimental data. Using a mixture of ceramide NS and NP compared to only ceramide NS or NP does not affect the results significantly. Ceramide EOS increases the permeability of water through the system.

TABLE 18

Permeability coefficients for water as obtained by methods according to the present disclosure. The presented uncertainties correspond to one standard error. Systems according to the present disclosure are indicated with *. The remaining systems are comparative examples

| System | log $K_{Pcalc}$ (cm/h) |
|---|---|
| 33-hairpin/33/33 stacked bilayer (no water) | −3.1 ± 0.1 |
| 33-hairpin/33/33 bilayer (with water) | −1.4 ± 0.1 |
| 33/33/33/100/0/0 | −5.5 ± 0.1 |
| 33/33/33/100/5/1 | −4.6 ± 0.2 |
| 33/33/33/75/0/1 | −5.3 ± 0.2 |
| 33/33/33/75/5/0 | −3.6 ± 0.3 |
| 33/33/33/75/5/1* | −4.5 ± 0.2 |
| 33/33/33/75/5/2* | −4.8 ± 0.1 |
| 33/33/33/75/5/4* | −2.9 ± 0.2 |
| 33/33/33/75/5/6* | −4.0 ± 0.1 |
| 33/33/33/75/10/1* | −3.5 ± 0.2 |
| 33/33/33/70/5/1* | −3.8 ± 0.2 |
| 33/33/33/70/5/2* | −4.9 ± 0.2 |
| 33-np/33/33/75/5/1* | −4.2 ± 0.1 |
| 33-ns/33/33/75/5/1* | −4.3 ± 0.1 |
| 33-C20-50/33/33/75/5/1* | −4.5 ± 0.2 |
| 33/33/33/80/5/1* | −4.9 ± 0.2 |
| 33/33-CHOL-SULF-10/33/80/5/1* | −3.7 ± 0.1 |
| 33/33/33-charged-FFA-10/80/5/1* | −3.6 ± 0.3 |
| 33/33/33-noXFFA30/75/5/1* | −5.2 ± 0.1 |

Example VI

System Setup and Simulations

Permeabilities of the atomistic model of the system proposed by Iwai et al. (Iwai et al., 2012) to benzene, codeine, dmso, naproxen, nicotine, testosterone and water were calculated. The results were compared to the calculated permeabilities of the lipid matrix system corresponding to 33/33/33/75/5/1, according to the present disclosure, from Example II. The permeabilities of the Iwai et al. system to water were taken from Example IV.

Calculations of the permeabilities were done according to Example 2. The presented permeability coefficients are from a total simulation time of 3 µs (30 pulls in each direction).
Results The comparison between the permeability of the system proposed by Iwai et al. and the 33/33/33/75/5/1 system, according to the present disclosure, is presented in Table 19. It can be observed that the mean absolute difference is slightly larger for the Iwai system and the mean square difference is larger. Most importantly, the Iwai model overestimated the permeability for all compounds except water. Thus, the system proposed by Iwai et al. predicts a higher permeability than experimental results from diffusion cells, which already are expected to overestimate the permeability compared to in vivo skin. The overestimations are larger for nonpolar compounds, i.e. with log $P_{octanol-water}$>0, whereas water, DMSO and ethanol match better with experimental data. Most drugs suitable for administration through skin are nonpolar. Thus the inventive method for predicting the permeability of a stratum corneum lipid matrix utilizing a model as described herein outperforms the Iwai system in this comparison.

TABLE 19

Calculated permeabilities, after 3 µs of sampling, of the Iwai et al. system and the 33/33/33/75/5/1 system, to different compounds. The presented uncertainties correspond to one standard error.

| Compound | log $K_{P303K}$ (cm/h) | Iwai et al. log $K_p$ (cm/h) | 33/33/33/75/5/1 log $K_p$ (cm/h) |
|---|---|---|---|
| Benzene | −0.8 | 0.6 ± 0.1 | −1.7 ± 0.2 |
| Codeine | −4.6 | −1.5 ± 0.2 | −6.4 ± 0.4 |
| DMSO | −3.1 | −2.9 ± 0.3 | −4.8 ± 0.2 |
| Ethanol | −2.8 | −2.5 ± 0.3 | −2.7 ± 0.2 |
| Naproxen | −3.0 | −0.8 ± 0.1 | −3.9 ± 0.2 |
| Nicotine | −1.8 | 0.6 ± 0.1 | −2.3 ± 0.3 |
| Testosterone | −2.7 | −0.6 ± 0.2 | −6.2 ± 0.3 |
| Water | −2.9 | −3.8 ± 0.2 | −4.5 ± 0.2 |
| Mean diff. | | 1.49 | −1.34 |
| Mean abs. Diff. | | 1.70 | 1.39 |
| Mean sq. diff. | | 4.25 | 2.85 |

Example VII

Details of the computer program products and computer readable media are given in this Example.

FIG. 12a is a schematic and very simplified illustration of an inventive computer program product 1 comprising computer program code 1a which, when executed by a device 2 having processing capability, enables the device 2 to provide a model of the stratum corneum lipid matrix as defined herein.

FIG. 12b is a schematic and very simplified illustration of a computer readable medium 3, in the figure exemplified by a digital versatile disc, carrying computer program code 1a as defined herein. FIG. 12b shows that the computer readable medium 3 can be a non-volatile storage medium.

LIST OF REFERENCES

Abraham and Martins, 2004, *J. Pharm. Sci.* 93: 1508-1523.
Abraham et al., 2015, *SoftwareX* 1-2: 19-25.
Alder and Wainwright, 1959, *J. Chem. Phys.* 31: 459.
Barratt, 1995, *Toxic. in vitro* 9: 27-37.
Bennett, 1976, *J. Comput. Phys.* 22: 245-268.
Berendsen et al., 1984, *J. Chem. Phys.* 81: 3684-3690.
Blank and McAuliffe, 1985, *J. Invest. Dermatol.* 85: 522-526.
Bouwstra et al., 2001, *Skin Pharmacol. Appl. Skin Physiol.* 14: 52-62.
Bussi et al., 2007, *J. Chem. Phys.* 126: 014101.
Chen, 2008, *J. Chem. Phys.* 129: 144113.
Crooks, 1999, *Phys. Rev. E*, 60: 2721-2726.
Crooks, 2000, *Phys. Rev. E*, 61: 2361-2366.
Dahlén and Pascher, 1979, *Chem. Phys. Lipids* 24: 119-133.
Das et al., 2009, *Soft Matter* 5: 4549-4555.
Daugherty, 1997, *Assessment of Chemical Exposures: Calculation Methods for Environmental Professionals* (CRC Press), 309.
Degim et al., 1998, *Int. J. Pharm.* 170: 129-133.
Essmann et al., 1995, *J. Chem. Phys.* 103: 8577-8593.
Forney et al., 2008, *Phys. Rev. E* 78: 051913.
Gupta et al., 2016, *J. Phys. Chem. B* DOI: 10.1021/acs.jpcb.6b05451.
Hill and Wertz, 2003, *Biochim. Biophys. Acta* 1616: 121-126.
Hess et al., 1997, *J. Comput. Chem.* 18: 1463-1472.
Idson, 1983, *Drug Metabol. Rev.* 14: 207-222.
Iwai et al., 2012, *J. Invest. Dermatol.* 132: 2215-2225.
Jorgensen et al., 1983, *J. Chem. Phys.* 79: 926-935.
Klauda et al., 2010, *J. Phys. Chem. B* 114: 7830-7843.
Kosztin et al., 2006, *J. Chem. Phys.* 124: 064106.
Kumar et al. 1992, *J. Comput. Chem.* 13:1011-1021.
Lindahl et al., 2014, *J. Chem. Phys.* 141: 044110.
Lundborg and Lindahl, 2014, *J. Phys. Chem. B* 119: 810-823.
McIntosh, 2003, *Biophys. J.* 85: 1675-1681.
Mitragoti et al., 1995, *J. Pharm. Sci.* 84: 697-706.
Miyamoto et al., 1992, *J. Comput. Chem.* 13: 952-962.
Mojumdar et al., 2016, *Biochim. Biophys. Acta* 1858: 1926-1934.
O'Boyle et al., 2011, *J. Cheminf.* 3: 33.
Park and Schulten, 2004, *J. Chem. Phys.* 120: 5946-5961.
Parrinello and Rahman, 1981, *J. Appl. Phys.* 52: 7182.
Pronk et al., 2013, *Bioinformatics* 29: 845-854.
Pronk et al., 2015, *J. Chem. Theory Comput.* 11: 2600-2608.
Roy and Flynn, 1989, *Pharm. Res.* 6: 825-832.
Rullgård et al., 2011, *J. Microscopy* 243: 234-256.
Scheuplein et al., 1965, *J. Invest. Dermatol.* 52: 63-70.
Scheuplein and Blank, 1973, *J. Invest. Dermatol.* 60: 286-296.
Scheuplein et al., 1969, *J. Invest. Dermatol.* 52: 63-70.
Schröter et al., 2009, *Biophys. J.* 97: 1104-1114.
Shirts and Chodera, 2008, *J. Chem. Phys.* 129: 124105-124110.
Swartzendruber et al., 1989, *J. Invest. Dermatol.* 92: 251-257.
Van der Merwe and Ackermann, 1987, *Int. J. Cosmet. Sci.* 9: 237-247.
Vanommeslaeghe et al., 2010, *J. Comput. Chem.* 31: 671-690.
Venable et al., 2014, *Biophys. J.* 107:134-145.
Yesselman et al., 2012, *J. Comput. Chem.* 33: 189-202.

ITEMIZED LIST OF EMBODIMENTS

1. Method for predicting the permeability of a stratum corneum lipid matrix to a compound, comprising the steps of:
    a) providing a model of the stratum corneum lipid matrix representing at least one repeating unit and comprising ceramides, free fatty acids, cholesterol and water, which model comprises the following:
        i) 25-45% total ceramides based on the molar concentration of all components except water, of which more than 90% are in extended configuration and wherein 0-30%, such as 1-30%, of said total ceramides are O-acyl ceramides and 100-70%, such as 99-70%, of said total ceramides are non-O-acyl ceramides;
        ii) 25-45% free fatty acid, based on the molar concentration of all components except water, wherein no more than, such as less than, 10% of the free fatty acids are negatively charged;
        iii) 25-40% cholesterol, based on the molar concentration of all components except water, wherein 1-40% of said cholesterol is located by the fatty acid moiety of said ceramides and wherein no more than, such as less than, 10% of the cholesterol molecules are replaced by cholesterol sulfate molecules; and
        iv) 0.2-6 water molecules per ceramide molecule;
    b) providing the molecular designators of a compound to which the permeability of the stratum corneum lipid matrix is to be predicted, and
    c) calculating, via means of computer simulation, the predicted permeability of the stratum corneum lipid matrix to said compound using said model and the molecular designators of the compound.
2. Method for predicting the permeability according to item 1, wherein the model in step 1 comprises the following:
    i) 25-45% total ceramides based on the molar concentration of all components except water, of which more than 90% are in extended configuration and wherein 1-30% of said total ceramides are O-acyl ceramides and 99-70% of said total ceramides are non-O-acyl ceramides;
        wherein the sphingoid moiety of said non-O-acyl ceramides has a length of 18-20 carbons and the fatty acid moiety of said non-O-acyl ceramides has a chain length distribution according to the following:
            0-15% of non-O-acyl ceramides have a fatty acid chain length of 20 carbons or less;
            0-15% of non-O-acyl ceramides have a fatty acid chain length of 21-22 carbons;
            25-50% of non-O-acyl ceramides have a fatty acid chain length of 23-24 carbons;
            20-50% of non-O-acyl ceramides have a fatty acid chain length of 25-26 carbons;
            0-15% of non-O-acyl ceramides have a fatty acid chain length of 27-28 carbons;
            0-20% of non-O-acyl ceramides have a fatty acid chain length of 29 carbons or more;
    ii) 25-45% free fatty acid, based on the molar concentration of all components except water, wherein said free fatty acids have a chain length distribution according to the following:

0-15% of the free fatty acids have a fatty acid chain length of 20 carbons or less;
0-15% of the free fatty acids have a fatty acid chain length of 21-22 carbons;
25-50% of the free fatty acids have a fatty acid chain length of 23-24 carbons;
20-50% of the free fatty acids have a fatty acid chain length of 25-26 carbons;
0-15% of the free fatty acids have a fatty acid chain length of 27-28 carbons; and
0-55% of the free fatty acids have a fatty acid chain length of 29 carbons or more, and wherein no more than, such as less than, 10% of the free fatty acids are negatively charged;
iii) 25-40% cholesterol, based on the molar concentration of all components except water, wherein 1-40% of said cholesterol is located by the fatty acid moiety of said ceramides and 99-60 of said cholesterol is located by the sphingoid moiety of the ceramides and wherein no more than, such as less than, 10% of the cholesterol molecules are replaced by cholesterol sulfate molecules; and
iv) 0.2-6 water molecules per ceramide molecule.

3. Method for predicting the permeability according to any one of items 1-2, wherein said repeating unit comprises two layers of extended ceramides arranged with their fatty acid side chains interfacing with each other and with their sphingoid side chains interfacing with each other.

4. Method for predicting the permeability according to any one of items 1-3, wherein said at least one repeating unit extends approximately 10-12 nm, such as 10.5-11 nm, such as 10.6 nm in the direction perpendicular to the membrane surface.

5. Method for predicting the permeability according to any one of items 1-4, wherein the distance between the ceramide head groups via the fatty acid side chain region is approximately 6.5 nm and the distance between the ceramide head groups via the sphingoid side chain region is approximately 4.5 nm in the direction perpendicular to the membrane surface.

6. Method for predicting the permeability according to any one of items 1-5, wherein 1-3 water molecules per ceramide molecule, such as 1-2 water molecules per ceramide molecule, such as 1 water molecule per ceramide molecule, are/is present in said model of the stratum corneum lipid matrix.

7. Method for predicting the permeability according to any one of items 1-6, wherein said model of the stratum corneum lipid matrix comprises approximately 1-10% O-acyl ceramides, such as approximately 3-8% O-acyl ceramides, such as approximately 5% O-acyl ceramides, based on the molar concentration of all components except water.

8. Method for predicting the permeability according to any one of items 1-7, wherein approximately 1-30% of the total ceramides, such as approximately 5-20% of the total ceramides, such as approximately 13-17% of the total ceramides are O-acyl ceramides in said model of the stratum corneum lipid matrix.

9. Method for predicting the permeability according to any one of items 1-8, wherein in said model of the stratum corneum lipid matrix approximately 90-100%, such as approximately 95-100%, such as approximately 98-100%, such as approximately 99-100%, such as approximately 100%, of the total ceramides are in extended configuration.

10. Method for predicting the permeability according to any one of items 1-9, wherein the molar concentration of total ceramides in said model of the stratum corneum lipid matrix is approximately 30-35% based on the molar concentration of all components except water, such as 33-34% based on the molar concentration of all components except water, and wherein 10-20% of said ceramides are O-acyl ceramides, such as 13-17% of said ceramides are O-acyl ceramides.

11. Method for predicting the permeability according to any one of items 1-10, wherein said non O-acyl ceramide is selected from the group consisting of ceramide NP, ceramide NS, ceramide AP and ceramide AS, such as the group consisting of ceramide NP and ceramide NS or the group consisting of ceramide AP and ceramide AS.

12. Method for predicting the permeability according to any one of items 1-11, wherein said non O-acyl ceramides have an approximate chain length distribution of the fatty acid moiety according to the following:
0-15% of non O-acyl ceramides are ceramide NP, NS, AP and/or AS which have a fatty acid chain length of 20 carbons;
0-15% of non O-acyl ceramides are ceramide NP, NS, AP and/or AS which have a fatty acid chain length of 22 carbons;
25-50% of non O-acyl ceramides are ceramide NP, NS, AP and/or AS which have a fatty acid chain length of 24 carbons;
20-50% of non O-acyl ceramides are ceramide NP, NS, AP and/or AS which have a fatty acid chain length of 26 carbons;
0-15% of non O-acyl ceramides are ceramide NP, NS, AP and/or AS which have a fatty acid chain length of 28 carbons;
0-10% of non O-acyl ceramides are ceramide NP, NS, AP and/or AS which have a fatty acid chain length of 30 carbons.

13. Method for predicting the permeability according to any one of items 1-12, wherein said non O-acyl ceramides are ceramides NP and ceramides NS.

14. Method for predicting the permeability according to any one of items 1-12, wherein said non O-acyl ceramides are ceramides AP and ceramides AS.

15. Method for predicting the permeability according to any one of items 1-14, wherein said O-acyl ceramide is ceramide EOS, EOP and/or EOH, such as ceramide EOS and/or EOP.

16. Method for predicting the permeability according to any one of items 1-15, wherein the molar concentration of free fatty acids in said model of the stratum corneum lipid matrix is approximately 30-35% based on the molar concentration of all components except water, such as 33-34 based on the molar concentration of all components except water.

17. Method for predicting the permeability according to any one of items 1-16, wherein said free fatty acids have an approximate chain length distribution according to the following:
4-6% of the fatty acids have a fatty acid chain length of 20 carbons;
8-10% of the fatty acids have a fatty acid chain length of 22 carbons;
32-36% of the fatty acids have a fatty acid chain length of 24 carbons;
25-29% of the fatty acids have a fatty acid chain length of 26 carbons;

8-10% of the fatty acids have a fatty acid chain length of 28 carbons; and 15-17% of the fatty acids have a fatty acid chain length of 30 carbons;

18. Method for predicting the permeability according to any one of items 1-17, wherein said free fatty acids have an approximate chain length distribution according to the following:

4.5% of the fatty acids have a fatty acid chain length of 20 carbons;

9.1% of the fatty acids have a fatty acid chain length of 22 carbons;

34.1% of the fatty acids have a fatty acid chain length of 24 carbons;

27.3% of the fatty acids have a fatty acid chain length of 26 carbons;

9.1% of the fatty acids have a fatty acid chain length of 28 carbons; and 15.9% of the fatty acids have a fatty acid chain length of 30 carbons.

19. Method for predicting the permeability according to any one of items 1-18, wherein 0-10%, such as 0-9% such as 0-5%, such as 0-2%, such as 0% of the free fatty acids are negatively charged.

20. Method for predicting the permeability according to any one of items 1-19, wherein the molar concentration of cholesterol in said model of the stratum corneum lipid matrix is approximately 30-35% based on the molar concentration of all components except water, such as 33-34% based on the molar concentration of all components except water.

21. Method for predicting the permeability according to any one of items 1-20, wherein approximately 15-35% of said cholesterol is located by the fatty acid moiety of said ceramides and approximately 65-85% of said cholesterol is located by the ceramide sphingoid moiety, such as 25% of the cholesterol located by the ceramide fatty moiety and 75% of the cholesterol located by the ceramide sphingoid moiety.

22. Method for predicting the permeability according to any one of items 1-21, wherein 0-10%, such as 0-9%, such as 0-5%, such as 0-2%, such as 0% of the cholesterol molecules are replaced by cholesterol sulfate molecules.

23. Method for predicting the permeability according to any one of items 1-22, wherein ratio of the molar concentration of ceramides:fatty acids:cholesterol in said model of the stratum corneum lipid matrix is approximately 1:1:1 based on the molar concentration of all components except water.

24. Method for predicting the permeability according to any one of items 1-23, wherein said model of the stratum corneum lipid matrix comprises the following:

i) 33-34% total ceramides based on the molar concentration of all components except water, of which 95-100% are in extended configuration, and wherein 13% of said total ceramides are ceramide EOS and 87% of said total ceramides are non O-acyl ceramides and wherein the sphingoid moiety of said non O-acyl ceramides has a length of 18 carbons and the fatty acid moiety of said non O-acyl ceramides has a chain length distribution approximately according to the following:

5.1% of non O-acyl ceramides are ceramide NP which have a fatty acid chain length of 20 carbons;

10.3% of non O-acyl ceramides are ceramide NP which have a fatty acid chain length of 22 carbons;

20.5% of non O-acyl ceramides are ceramide NP which have a fatty acid chain length of 24 carbons;

20.5% of non O-acyl ceramides are ceramide NS which have a fatty acid chain length of 24 carbons;

30.8% of non O-acyl ceramides are ceramide NP which have a fatty acid chain length of 26 carbons;

10.3% of non O-acyl ceramides are ceramide NP which have a fatty acid chain length of 28 carbons; and 2.5% of non O-acyl ceramides are ceramide NP which have a fatty acid chain length of 30 carbons, and ii) 33-34% fatty acid, based on the molar concentration of all components except water, wherein the fatty acid chain length distribution is approximately according to the following:

4.5% of the fatty acids have a fatty acid chain length of 20 carbons;

9.1% of the fatty acids have a fatty acid chain length of 22 carbons;

34.1% of the fatty acids have a fatty acid chain length of 24 carbons;

27.3% of the fatty acids have a fatty acid chain length of 26 carbons;

9.1% of the fatty acids have a fatty acid chain length of 28 carbons; and 15.9% of the fatty acids have a fatty acid chain length of 30 carbons;

iii) 33-34% cholesterol, based on the molar concentration of all components except water, wherein approximately 25% of said cholesterol is located by the ceramide fatty acid moiety of said ceramides and approximately 75% of said cholesterol is located by the ceramide sphingoid moiety; and iv) 1 water molecule per ceramide molecule.

25. Method for predicting the permeability according to any one of items 1-24, wherein said cholesterol located by the fatty acid moiety of said ceramides is arranged such that its hydroxyl group can form hydrogen bonds with the polar ceramide head groups and its tail is arranged in the general orientation of the ceramide sphingoid side chains or in the general orientation of the ceramide fatty acid side chains, depending on which of the ceramide head group said cholesterol is located.

26. Method for predicting the permeability according to any one of items 1-25, wherein said molecular designators are atomic coordinates.

27. Method for predicting the permeability according to any one of items 1-26, wherein said molecular designators are atomic coordinates and force field parameters.

28. Method for predicting the permeability according to item 27, wherein said force field parameters are at least one force field parameter selected from the group consisting of non-bonded interactions and bonded interactions.

29. Method for predicting the permeability according to item 28, wherein said non-bonded interactions are selected from the group consisting of van der Waals and electrostatic interactions.

30. Method for predicting the permeability according to item 28, wherein said bonded interactions are selected from the group consisting of bonds, angles and dihedral angles of a compound.
31. Method for predicting the permeability according to any one of items 1-30, wherein the method further comprises the steps of:
   d) providing the molecular designators of a second compound to which the permeability of the stratum corneum lipid matrix is to be predicted;
   e) calculating, via means of computer simulation, the predicted permeability of the stratum corneum lipid matrix to said second compound using said model and the molecular designators of the said second compound; and
   f) comparing the obtained predicted permeability to said first compound calculated in step c) and to said second compound calculated in step d) and predicting the effect of a structural difference between a first compound and a second compound on the permeability of the stratum corneum lipid matrix to said compounds.
32. Method for predicting the permeability according to any one of item 1-30, wherein the step a) further comprises the steps of:
   a1) providing the molecular designators as defined herein for at least one chemical permeability modifying agent (PMA);
   a2) providing, via means of computer simulation using the model according to a) and the molecular designators of the at least one PMA according to a1), a modified model of the stratum corneum lipid matrix with the at least one PMA;
   wherein said modified model according to a2) is used for predicting the permeability of a stratum corneum lipid matrix with at least one PMA to the compound in step c).
33. Method for predicting the permeability according to item 32, further comprises the steps of:
   d) calculating the predicted permeability of the stratum corneum lipid matrix to said compound from step b) via means of computer simulation using the model from step a); and
   e) comparing the obtained predicted permeability to said compound calculated in step c) and step d), whereby obtaining a prediction of the effect of at least one PMA on the permeability of a stratum corneum lipid matrix to a compound.
34. Method of predicting the effect of a structural difference between a first compound and a second compound on the permeability of the stratum corneum lipid matrix to said compounds, comprising the steps of
   a) providing a model of the stratum corneum lipid matrix as defined in any one of items 1-25;
   b) providing molecular designators as defined in any one of items 26-30 for the first compound;
   c) providing molecular designators as defined in any one of items 26-30 for the second compound;
   d) calculating the permeability of the stratum corneum lipid matrix to the first compound via means of computer simulation using the model of step a) and the molecular designators of step b);
   e) calculating the permeability of the stratum corneum lipid matrix to the second compound via means of computer simulation using the model of step a) and the molecular designators of step c); and
   f) comparing the obtained predicted permeability to said first compound calculated in step d) and to said second compound calculated in step e).
35. Method for predicting the effect of a structural difference between a first compound and a second compound on the permeability of the stratum corneum lipid matrix to said compounds according to item 34, wherein the second compound is a modification of the first compound.
36. Method for predicting the permeability of a stratum corneum lipid matrix with at least one chemical permeability modifying agent (PMA) to a compound, comprising the steps of:
   a) providing a model of the stratum corneum lipid matrix as defined in any one of items 1-25;
   b) providing the molecular designators as defined in any one of items 26-30 of said at least one PMA;
   c) providing, via means of computer simulation using the model and the molecular designators of the at least one PMA, a modified model of the stratum corneum lipid matrix with the at least one PMA;
   d) providing the molecular designators as defined in any one of items 26-30 for said compound; and
   e) calculating the predicted permeability to said compound from step d) of the stratum corneum lipid matrix and the at least one PMA via means of computer simulation using the modified model of step c).
37. Method for predicting the effect of at least one chemical permeability modifying agent (PMA) on the permeability of a stratum corneum lipid matrix to a compound, comprising the steps of:
   a) providing a model of the stratum corneum lipid matrix as defined in any one of items 1-25;
   b) providing the molecular designators as defined in any one of items 26-30 of said at least one PMA;
   c) providing, via means of computer simulation using the model and the molecular designators of the at least one PMA, a modified model of the stratum corneum lipid matrix with the at least one PMA;
   d) providing the molecular designators as defined in any one of items 26-30 for said compound;
   e) calculating the predicted permeability of the stratum corneum lipid matrix to said compound from step d) via means of computer simulation using the model from step a);
   f) calculating the predicted permeability to said compound from step d) of the stratum corneum lipid matrix and the at least one PMA via means of computer simulation using the modified model of step c); and
   g) comparing the obtained predicted permeability to said compound calculated in step e) and step f).
38. Method for predicting the effect of at least one PMA on the permeability to a compound of a stratum corneum lipid matrix according to item 37, wherein the calculations in step e) and f) are performed in parallel or in sequence.
39. Method for predicting the effect of at least one PMA on the permeability to a compound of a stratum corneum lipid matrix according to any one of items 37-38 or, wherein said at least one PMA is two, three, four or more PMAs.
40. Method for predicting the effect of at least one PMA on the permeability to a compound of a stratum corneum lipid matrix according to item 39, wherein in step c) the modified model of the stratum corneum lipid matrix is formed by addition of said at least two, three, four or more PMAs to the model followed by equilibration.

41. Method for predicting the effect of at least one PMA on the organization of a stratum corneum lipid matrix, comprising the steps of:
    a) providing a model of the stratum corneum lipid matrix as defined in any one of items 1-25;
    b) providing the molecular designators as defined in any one of items 26-30 for said PMA; and
    c) predicting, via means of computer simulation using the model of step a) and the molecular designators of step b), if said PMA mainly interacts with the head groups of the ceramides, with the sphingoid moieties or with the fatty acid moieties of the ceramides of said model of the stratum corneum lipid matrix.

42. Method of identifying a PMA for a compound which has a desired effect on the permeability of a stratum corneum lipid matrix to said compound, comprising the steps of
    a) providing a model of the stratum corneum lipid matrix as defined in any one of items 1-25;
    b) providing the molecular designators as defined in any one of items 26-30 of each candidate PMA;
    c) providing, via means of computer simulation using the model of step a) and the molecular designators of a candidate PMA of step b), a modified model of the stratum corneum lipid matrix with the candidate PMA;
    d) providing the molecular designators as defined in any one of items 26-30 for said compound;
    e) calculating the predicted permeability to said compound from step d) of the stratum corneum lipid matrix via means of computer simulation using the model of step a) and the molecular designators of step d);
    f) calculating the predicted permeability to said compound from step d) of the stratum corneum lipid matrix with the candidate PMA from step b) via means of computer simulation using the modified model of step c) and the molecular designators of step d);
    g) comparing the obtained predicted permeability to said compound calculated in step e) and f); and
    h) repeating at least steps c, f and g) for said compound and each candidate PMA to be tested until the desired effect is predicted.

43. Method of identifying a PMA for a compound, comprising the steps of
    a) providing a model of the stratum corneum lipid matrix as defined in any one of items 1-25;
    b) providing the molecular designators as defined in any one of items 26-30 of at least one candidate PMA;
    c) providing, via means of computer simulation using the model of step a) and the molecular designators of the at least one candidate PMA of step b), a modified model of the stratum corneum lipid matrix with the at least one candidate PMA;
    d) providing the molecular designators as defined in any one of items 26-30 for said compound;
    e) calculating the predicted permeability to said compound from step d) of the stratum corneum lipid matrix via means of computer simulation using the model of step a);
    f) calculating the predicted permeability to said compound from step b) of the stratum corneum lipid matrix with said at least one candidate PMA from step c) via means of computer simulation using the modified model of step c) and the molecular designators of step d), and
    g) comparing the obtained predicted permeability to said compound in step e) and to said compound and said at least one candidate PMA in step f).

44. Method for predicting the permeability to a compound of the stratum corneum lipid matrix according to any one of items 1-33; method of predicting the effect of a structural difference between a first compound and a second compound according to item 34 or 35, method for predicting the permeability of a stratum corneum lipid matrix with at least one chemical PMA to a compound according to item 36; method for predicting the effect of at least one PMA on the permeability of a stratum corneum lipid matrix to a compound according to any one of items 37-40; method for predicting the effect of at least one PMA on the organization of a stratum corneum lipid matrix according to item 41; method of identifying a PMA for a compound which has a desired effect on the permeability of a stratum corneum lipid matrix to said compound and method of identifying a PMA according to item 42; or method of identifying a PMA for a compound according to item 43, wherein said computer simulation comprises Molecular Dynamics simulations.

45. Method for predicting the permeability of a stratum corneum lipid matrix with at least one chemical PMA to a compound according to item 36; method for predicting the effect of at least one PMA on the permeability of a stratum corneum lipid matrix to a compound according to any one of items 37-40; method for predicting the effect of at least one PMA on the organization of a stratum corneum lipid matrix according to item 41; method of identifying a PMA for a compound which has a desired effect on the permeability of a stratum corneum lipid matrix to said compound and method of identifying a PMA according to item 42; or method of identifying a PMA for a compound according to item 43, wherein said PMA is a permeability enhancing agent or a permeability decreasing agent.

46. Method according to item 45, wherein said PMA is a chemical permeability enhancing agent.

47. Method according to any one of items 45-46, wherein said PMA is selected from the group consisting of water; sulfoxides and related compounds, such as dimethylsulphoxide (DMSO) and dimethylformamide (DMF); azone and derivatives thereof; pyrrolidones, such as N-methyl-2-pyrrolidone (NMP) and 2-pyrrolidone (2P); fatty acids, such as oleic acid; alcohols and glycols, such as ethanol; urea analogues, such as cyclic urea; essential oils, terpenes and terpenoids, such as eucalyptus oil, I-menthol and d-limonene; sesquiterpene, free fatty acids and ceramides.

48. Method according to any one of items 45-46, wherein said PMA is selected from the group consisting of azone, DMSO, ethanol, and water.

49. Use of a model as defined in any one of items 1-30 for predicting the permeability of a stratum corneum lipid matrix to a compound, use of the model for predicting the permeability of a stratum corneum lipid matrix with at least one chemical permeability modifying agent (PMA) to a compound, use of the model for predicting the effect of at least one PMA on the permeability of a stratum corneum lipid matrix to a compound, use of the model for predicting the effect of at least one PMA on the organization of a stratum corneum lipid matrix, use of the model for identifying a PMA for a compound which has a desired effect on the permeability of a stratum corneum lipid matrix, or use of the model for identifying a PMA for a compound.

50. A computer program product comprising a computer-readable storage medium with instructions adapted to carry out the method as defined in any one of items 1-49 when executed by a device having processing capability.

51. A computer program product comprising computer program code which, when executed by a device having processing capability, enables the device to provide a model of the stratum corneum lipid matrix as defined in any one of items 1-49.

52. A computer readable medium carrying computer program code according to item 51.

53. A computer readable medium according to item 52, where the computer readable medium is a non-volatile storage medium.

The invention claimed is:

1. A computer-implemented method for analyzing the permeability of a stratum corneum lipid matrix to a compound, comprising the steps of:
   a) providing a model of the stratum corneum lipid matrix representing at least one repeating unit and comprising ceramides, free fatty acids, cholesterol and water, which model comprises the following:
      i) 25-45% total ceramides based on the molar concentration of all components except water, of which more than 90% are in extended configuration and wherein 0-30% of said total ceramides are O-acyl ceramides and 100-70% of said total ceramides are non-O-acyl ceramides;
      ii) 25-45% free fatty acid, based on the molar concentration of all components except water, wherein no more than 10% of the free fatty acids are negatively charged;
      iii) 25-40% cholesterol, based on the molar concentration of all components except water, wherein 1-40% of said cholesterol is located by the fatty acid moiety of said ceramides and wherein no more than 10% of the cholesterol molecules are replaced by cholesterol sulfate molecules; and
      iv) 0.2-6 water molecules per ceramide molecule;
   b) providing the molecular designators of a compound to which the permeability of the stratum corneum lipid matrix is to be predicted, and
   c) calculating, via means of computer simulation, the predicted permeability of the stratum corneum lipid matrix to said compound using said model and the molecular designators of the compound.

2. The method for analyzing the permeability according to claim 1, wherein the model in step a comprises the following:
   i) 25-45% total ceramides based on the molar concentration of all components except water, of which more than 90% are in extended configuration and wherein 1-30% of said total ceramides are O-acyl ceramides and 99-70% of said total ceramides are non-O-acyl ceramides;
      wherein the sphingoid moiety of said non-O-acyl ceramides has a length of 18-20 carbons and the fatty acid moiety of said non-O-acyl ceramides has a chain length distribution according to the following:
         0-15% of non-O-acyl ceramides have a fatty acid chain length of 20 carbons or less;
         0-15% of non-O-acyl ceramides have a fatty acid chain length of 21-22 carbons;
         25-50% of non-O-acyl ceramides have a fatty acid chain length of 23-24 carbons;
         20-50% of non-O-acyl ceramides have a fatty acid chain length of 25-26 carbons;
         0-15% of non-O-acyl ceramides have a fatty acid chain length of 27-28 carbons;
         0-20% of non-O-acyl ceramides have a fatty acid chain length of 29 carbons or more;
   ii) 25-45% free fatty acid, based on the molar concentration of all components except water, wherein said free fatty acids have a chain length distribution according to the following:
         0-15% of the free fatty acids have a fatty acid chain length of 20 carbons or less;
         0-15% of the free fatty acids have a fatty acid chain length of 21-22 carbons;
         25-50% of the free fatty acids have a fatty acid chain length of 23-24 carbons;
         20-50% of the free fatty acids have a fatty acid chain length of 25-26 carbons;
         0-15% of the free fatty acids have a fatty acid chain length of 27-28 carbons; and
         0-55% of the free fatty acids have a fatty acid chain length of 29 carbons or more and wherein no more than, such as less than, 10% of the free fatty acids are negatively charged;
   iii) 25-40% cholesterol, based on the molar concentration of all components except water, wherein 1-40% of said cholesterol is located by the fatty acid moiety of said ceramides and 99-60% of said cholesterol is located by the sphingoid moiety of the ceramides and wherein no more than 10% of the cholesterol molecules are replaced by cholesterol sulfate molecules; and
   iv) 0.2-6 water molecules per ceramide molecule.

3. The method for analyzing the permeability according to claim 1, wherein 1-3 water molecules per ceramide molecule are present in said model of the stratum corneum lipid matrix.

4. The method for analyzing the permeability according to claim 1, wherein said model of the stratum corneum lipid matrix comprises approximately 1-10% O-acyl ceramides based on the molar concentration of all components except water.

5. The method for analyzing the permeability according to claim 1, wherein approximately 1-30% of the total ceramides are O-acyl ceramides in said model of the stratum corneum lipid matrix.

6. The method for analyzing the permeability according to claim 1, wherein in said model of the stratum corneum lipid matrix approximately 90-100% of the total ceramides are in extended configuration.

7. The method for analyzing the permeability according to claim 1, wherein the molar concentration of total ceramides in said model of the stratum corneum lipid matrix is approximately 30-35% based on the molar concentration of all components except water, and wherein 10-20% of said ceramides are O-acyl ceramides.

8. The method for analyzing the permeability according to claim 1, wherein ratio of the molar concentration of ceramides:fatty acids:cholesterol in said model of the stratum corneum lipid matrix is approximately 1:1:1 based on the molar concentration of all components except water.

9. The method for analyzing the permeability according to claim 1, wherein said model of the stratum corneum lipid matrix comprises the following:
- i) 33-34% total ceramides based on the molar concentration of all components except water, of which 95-100% are in extended configuration, and
   wherein 13% of said total ceramides are ceramide EOS and 87% of said total ceramides are non O-acyl ceramides and wherein the sphingoid moiety of said non O-acyl ceramides has a length of 18 carbons and the fatty acid moiety of said non O-acyl ceramides has a chain length distribution approximately according to the following:
     - 5.1% of non O-acyl ceramides are ceramide NP which have a fatty acid chain length of 20 carbons;
     - 10.3% of non O-acyl ceramides are ceramide NP which have a fatty acid chain length of 22 carbons;
     - 20.5% of non O-acyl ceramides are ceramide NP which have a fatty acid chain length of 24 carbons;
     - 20.5% of non O-acyl ceramides are ceramide NS which have a fatty acid chain length of 24 carbons;
     - 30.8% of non O-acyl ceramides are ceramide NP which have a fatty acid chain length of 26 carbons;
     - 10.3% of non O-acyl ceramides are ceramide NP which have a fatty acid chain length of 28 carbons; and
     - 2.6% of non O-acyl ceramides are ceramide NP which have a fatty acid chain length of 30 carbons, and
- ii) 33-34% fatty acid, based on the molar concentration of all components except water, wherein the fatty acid chain length distribution is approximately according to the following:
    - 4.5% of the fatty acids have a fatty acid chain length of 20 carbons;
    - 9.1% of the fatty acids have a fatty acid chain length of 22 carbons;
    - 34.1% of the fatty acids have a fatty acid chain length of 24 carbons;
    - 27.3% of the fatty acids have a fatty acid chain length of 26 carbons;
    - 9.1% of the fatty acids have a fatty acid chain length of 28 carbons; and
    - 15.9% of the fatty acids have a fatty acid chain length of 30 carbons;
- iii) 33-34% cholesterol, based on the molar concentration of all components except water, wherein approximately 25% of said cholesterol is located by the ceramide fatty acid moiety of said ceramides and approximately 75% of said cholesterol is located by the ceramide sphingoid moiety; and
- iv) 1 water molecule per ceramide molecule.

10. The method for analyzing the permeability according to claim 1, wherein the method further comprises the steps of:
- d) providing the molecular designators of a second compound to which the permeability of the stratum corneum lipid matrix is to be predicted;
- e) calculating, via means of computer simulation, the predicted permeability of the stratum corneum lipid matrix to said second compound using said model and the molecular designators of the said second compound; and
- f) comparing the obtained predicted permeability to said first compound calculated in step c) and to said second compound calculated in step d) and predicting the effect of a structural difference between a first compound and a second compound on the permeability of the stratum corneum lipid matrix to said compounds.

11. The method for analyzing the permeability according to claim 1, wherein the step a) further comprises the steps of:
- a1) providing the molecular designators as defined herein for at least one chemical permeability modifying agent (PMA);
- a2) providing, via means of computer simulation using the model according to a) and the molecular designators of the at least one PMA according to a1), a modified model of the stratum corneum lipid matrix with the at least one PMA;
- wherein said modified model according to a2) is used for predicting the permeability of a stratum corneum lipid matrix with at least one PMA to the compound in step c).

12. The method for analyzing the permeability according to claim 11, further comprising the steps of:
- d) calculating the predicted permeability of the stratum corneum lipid matrix to said compound from step b) via means of computer simulation using the model from step a); and
- e) comparing the obtained predicted permeability to said compound calculated in step c) and step d),
- whereby obtaining a prediction of the effect of at least one PMA on the permeability of a stratum corneum lipid matrix to a compound.

13. The method for analyzing the effect of at least one PMA on the organization of a stratum corneum lipid matrix, comprising the steps of:
- a) providing a model of the stratum corneum lipid matrix as defined in claim 1;
- b) providing molecular designators for said at least one PMA; and
- c) predicting, via means of computer simulation using the model of step a) and the molecular designators of step b), if said at least one PMA mainly interacts with the head groups of the ceramides, with the sphingoid moieties or with the fatty acid moieties of the ceramides of said model of the stratum corneum lipid matrix.

14. Use of a model as defined in claim 1 for analyzing the permeability of a stratum corneum lipid matrix to a compound, for predicting the permeability of a stratum corneum lipid matrix with at least one chemical permeability modifying agent (PMA) to a compound, for predicting the effect of at least one PMA on the permeability of a stratum corneum lipid matrix to a compound, or for predicting the effect of at least one PMA on the organization of a stratum corneum lipid matrix.

15. A computer program product comprising computer program code which, when executed by a device having processing capability, enables said device to provide a model of the stratum corneum lipid matrix as defined in claim 1.

16. A computer readable medium carrying computer program code according to claim 15.

17. A computer readable medium according to claim 16, where said computer readable medium is a non-volatile storage medium.

* * * * *